United States Patent [19]
Kozlik et al.

[11] Patent Number: 5,519,034
[45] Date of Patent: May 21, 1996

[54] TETRAISOQUINOLINE COMPOUNDS WHICH HAVE USEFUL PHARMACEUTICAL UTILITY

[75] Inventors: Antonin Kozlik; Bruce J. Sargent; Patricia L. Needham, all of Nottinghamshire, United Kingdom

[73] Assignee: The Boots Company PLC, Nottingham, United Kingdom

[21] Appl. No.: 244,368

[22] PCT Filed: Dec. 12, 1992

[86] PCT No.: PCT/EP92/02900

§ 371 Date: Aug. 18, 1994

§ 102(e) Date: Aug. 18, 1994

[87] PCT Pub. No.: WO93/13073

PCT Pub. Date: Jul. 8, 1993

[30] Foreign Application Priority Data

Dec. 23, 1991 [GB] United Kingdom .................. 9127306

[51] Int. Cl.$^6$ ...................... C07D 217/04; A61K 31/47
[52] U.S. Cl. .................. 514/307; 546/145; 546/146; 546/147; 546/148; 546/149; 546/150
[58] Field of Search ................. 546/146, 148, 546/145, 147, 149, 150; 514/307

[56] References Cited

U.S. PATENT DOCUMENTS

| | | | |
|---|---|---|---|
| 3,571,638 | 7/1973 | Inariba et al. | 310/155 |
| 3,717,639 | 2/1973 | Neumeyer et al. | 546/140 |
| 3,755,330 | 8/1973 | Houllhan et al. | 260/283 |
| 3,777,026 | 12/1973 | Anderson et al. | 546/146 |
| 3,852,448 | 12/1974 | Anderson | 546/146 |
| 3,872,130 | 3/1975 | Kreighbaum et al. | 260/289 |
| 4,013,664 | 3/1977 | Kupchan et al. | 200/288 |
| 4,018,927 | 4/1977 | Vorhees | 424/260 |
| 4,115,389 | 9/1978 | Monkovic | 289/260 |
| 4,126,615 | 11/1978 | Turcsan et al. | 542/440 |
| 4,194,044 | 3/1980 | Mohacse | 546/146 |
| 4,235,906 | 1/1979 | Savarese et al. | 424/258 |
| 4,491,665 | 1/1985 | El-Sayad et al. | 546/140 |
| 4,514,569 | 4/1985 | Hendrickson et al. | 546/146 |
| 4,678,853 | 7/1987 | Ivanov et al. | 546/146 |
| 4,737,504 | 4/1988 | Miller et al. | 514/307 |
| 5,071,859 | 12/1991 | Knudsen et al. | 514/326 |

FOREIGN PATENT DOCUMENTS

| | | |
|---|---|---|
| 191542A | 8/1986 | European Pat. Off. . |
| 419247A | 3/1991 | European Pat. Off. . |
| 868733 | 1/1942 | France . |
| 082252 | 8/1972 | Japan . |
| 018765 | 7/1974 | United Kingdom . |

OTHER PUBLICATIONS

Thoen. Physcans Guide to Rare Diseases, 1992, pp. 345–346.

International Search Report of PCT/EP/92/02900.

Iwasawa et al. "Studies on Tetrahydroisoquinolines (THI) (I) Bronchodilator Activity and Structure–Activity Relationship." *Jap. J. Pharmacol* vol. 17 (1967) pp. 143–152.

Shams et al. "Pharmacological Evaluation of the beta–Adrenoceptor Agonist Properties of N–Benzyl Substituted Trimetoquinol Analogs." *Eur. J. Pharmacol* vol. 184 (1990) pp. 51–256. Abstract.

Riggs et al. "Specific Dopamine D–1 and $DA_1$ Properties of 4–(Mono– and –dihydroxyphenyl)–1,2,3,4–tetrahydroisoquinoline and its Tetrahydrothieno[2,3–c]pyridine Analogue." *J. Med. Chem.* vol. 30 (1987) pp. 1454–1458.

Charifson. "Pharmacological Effects of Tetrahydroisoquinoline Derivatives." *Drugs of the Future* vol. 14 (1989) pp. 1179–1185.

Charifson et al. "Synthesis and Pharmacological Characterization of 1–Phenyl–,4–Phenyl–, and 1–Benzyl–1,2,3,4–tetrahydroisoquinolines as Dopamine Receptor Ligands." *J. Med. Chem.* vol. 31 (1988) pp. 1941–1946.

Charifson et al. "Conformational Analysis and Molecular Modeling of 1–phenyl–,4–Phenyl–, and 1–Benzyl–1,2,3,4–tetrahydroisoquinolines as $D_1$ Dopamine Receptor Ligands." *J. Med. Chem.* vol. 32 (1989) pp. 2050–2058.

Kerkman et al. "A–69024; a Non–Benzazepine Antagonist with Selectivity for the Dopamine $D_1$ Receptor," *Eur. J. Pharmacol.* vol. 166 (1989) pp. 481–491.

Riddall et al. "A Comparison of the Selectivities of SCH23390 and BW737C for $D_1$, $D_2$ and $5HT_2$ Binding Sites Both in vitro and in vivo." 17th Collegium Internationale Neuro–Psychopharmacologicum, Kyoto, Japan (1990) poster presentation P–13–5–5.

*Primary Examiner*—C. Warren Ivy
*Assistant Examiner*—Zinna N. Davis
*Attorney, Agent, or Firm*—Nikaido, Marmelstein, Murray & Oram

[57] ABSTRACT

Tetrahydroisoquinoline compounds of formula I

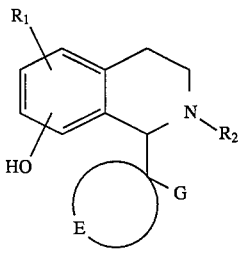

and pharmaceutically acceptable salts and lipophilic ester thereof have utility as analgesics and in the treatment of psychoses, Parinson's disease, Lesch-Nyan syndrome, attention deficit disorder or cognitive impairment or in the relief of drug dependence or tardive dyskinesia.

18 Claims, No Drawings

TETRAHYDROISOQUINOLINE COMPOUNDS WHICH HAVE USEFUL PHARMACEUTICAL UTILITY

This application is filed under 35 U.S.C. 371 as national stage entry of PCT/EP92/02900, filed 12 Dec. 1992.

The present invention relates to novel tetrahydroisoquinoline compounds, to pharmaceutical compositions containing the compounds, methods of preparing the compounds and the use of the compounds in analgesia and in the treatment of psychoses (for example schizophrenia), Parkinsons's disease, Lesch-Nyan syndrome, attention deficit disorder or cognitive impairment or in the relief of drug dependence or tardive dyskinesia.

The present invention provides tetrahydroisoquinoline compounds of formula I

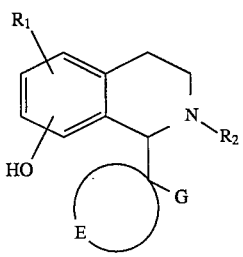

and pharmaceutically acceptable salts thereof, in which:

$R_1$ represents one or more substituents selected from H, halo, hydroxy, alkyl of 1 to 3 carbon atoms (optionally substituted by hydroxy), alkoxy of 1 to 3 carbon atoms, alkylthio of 1 to 3 carbon atoms, alkylsulphinyl of 1 to 3 carbon atoms, alkylsulphonyl of 1 to 3 carbon atoms, nitro, cyano, polyhaloalkyl of 1 to 3 carbon atoms, polyhaloalkoxy of 1 to 3 carbon atoms, phenyl (optionally substituted by one or more substituents selected from halo, alkyl of 1 to 3 carbon atoms or alkoxy of 1 to 3 carbon atoms), or $R_1$ is carbamoyl optionally alkylated by one or two alkyl groups each independently of 1 to 3 carbon atoms;

$R_2$ represents an aliphatic group containing 1 to 3 carbon atoms optionally substituted by hydroxy or alkoxy containing 1 to 3 carbon atoms;

E represents an alkylene chain containing 2 to 5 carbon atoms optionally substituted by one or more alkyl groups containing 1 to 3 carbon atoms, and G represents phenyl or phenyl substituted by one or more substituents which may be the same or different, and which are independently alkyl of 1 to 3 carbon atoms, alkoxy of 1 to 3 carbon atoms, halo, hydroxy, polyhaloalkyl of 1 to 3 carbon atoms, polyhaloalkoxy of 1 to 3 carbon atoms, cyano, alkylthio of 1 to 3 carbon atoms, alkylsulphinyl of 1 to 3 carbon atoms, alkylsulphonyl of 1 to 3 carbon atoms, phenyl (optionally substituted by one or more substituents selected from halo, alkyl of 1 to 3 carbon atoms or alkoxy of 1 to 3 carbon atoms), carbamoyl optionally alkylated by one or two alkyl groups each independently of 1 to 3 carbon atoms, or G represents a phenyl ring having fused thereto a heterocyclic or aromatic carbocyclic ring;

and O-acylated derivatives thereof.

In preferred compounds of formula I, the hydroxy group is in the 7-position. Accordingly one group of preferred compounds of the invention is represented by formula II

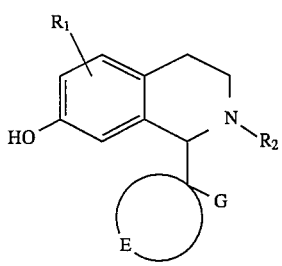

and pharmaceutically acceptable salts thereof, in which $R_1$, $R_2$, E and G are as defined above and O-acylated derivatives thereof.

A preferred group of O-acylated derivatives of compounds of formula I is represented by compounds of formula III

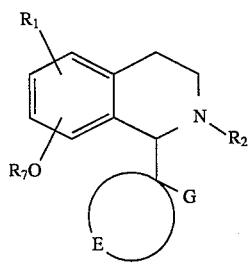

and pharmaceutically acceptable salts thereof, in which $R_1$, $R_2$, E and G are as defined above and $R_7$ represents an acyl group derived from a carboxylic acid having 6 to 20 carbon atoms preferably 7 to 18 carbon atoms. In more preferred compounds of formula III, $R_7$ represents heptanoyl, decanoyl, dodecanoyl, hexadecanoyl or octadecanoyl. In most preferred compounds of formula III, the group $OR_7$ is in the 7-position.

In preferred compounds of formula I, II or III, $R_1$ represents H, halo, hydroxy, alkyl of 1 to 3 carbon atoms, alkoxy of 1 to 3 carbon atoms, alkylthio of 1 to 3 carbon atoms, nitro, polyfluoroalkyl of 1 to 3 carbon atoms, polyfluoroalkoxy of 1 to 3 carbon atoms or phenyl optionally substituted by fluoro, chloro, bromo, methyl or methoxy. In more preferred compounds of formula I, II or III, $R_1$ represents H, fluoro, chloro, bromo, hydroxy, methyl, methoxy, phenyl or nitro. In particularly preferred compounds of formula II, $R_1$ represents one substituent in the 6-position which is H, fluoro, chloro, bromo, hydroxy, methyl, methoxy or phenyl.

In preferred compounds of formula I, II or III, $R_2$ represents an alkyl group containing 1 to 3 carbon atoms (for example methyl or ethyl) optionally substituted by hydroxy (for example $R_2$ is 2-hydroxyethyl) or by methoxy (for example $R_2$ is 2-methoxyethyl) or $R_2$ represents an alkenyl group of 2 or 3 carbon atoms (for example allyl).

In preferred compounds of formula I, II or III, the group E represents —(CH$_2$)$_2$—, —(CH$_2$)$_3$—, —(CH$_2$)$_4$—, —(CH$_2$)$_5$— or —CH$_2$CMe$_2$CH$_2$—. In particularly preferred compounds of formula I or II, E represents —(CH$_2$)$_2$— or —(CH$_2$)$_3$—.

In preferred compounds of formula I, II or III, G represents phenyl or phenyl substituted by one or more substituents which are independently alkyl of 1 to 3 carbon atoms, alkoxy of 1 to 3 carbon atoms, halo, hydroxy, polyfluoroalkyl of 1 to 3 carbon atoms, polyfluoroalkoxy of 1 to 3 carbon atoms or phenyl optionally substituted by fluoro, chloro, bromo, methyl or methoxy or G represents naphthyl or dihydrobenzofuran-7-yl.

In more preferred compounds of formula I, II or III, G represents phenyl or phenyl optionally substituted by methyl, hydroxy, methoxy, methylthio, fluoro, chloro, bromo, trifluoromethyl, cyano or trifluoromethoxy or G represents a naphthyl or dihydrobenzo[b]furan-7-yl group. In particularly preferred compounds of formula I, II or III, G represents phenyl, 2-chlorophenyl, 4-chlorophenyl, 2,4-dichlorophenyl, 3,4-dichlorophenyl, 4-fluorophenyl, 2-bromophenyl, 2-methylphenyl, 2-methylthiophenyl, 2-methoxyphenyl, 3-methoxyphenyl, 4-methoxyphenyl, 4-hydroxyphenyl, 3-trifluoromethylphenyl, 4-trifluoromethoxyphenyl, 2-cyanophenyl, 2-bromo-4,5 -dimethoxyphenyl, 1-naphthyl, 2-naphthyl or 2,3-dihydrobenzo[ b]furan-7-yl.

Specific compounds of formula I are:

6,7-dihydroxy-2-methyl-1-(1-phenylcyclopropyl)-1,2,3,4-tetrahydroisoquinoline.

6,7-dihydroxy-2-methyl-1-(1-phenylcyclobutyl)-1,2,3,4-tetrahydroisoquinoline.

6,7-dihydroxy-2-methyl-1-(3,3-dimethyl-1-phenylcyclobutyl)- 1,2,3,4-tetrahydroisoquinoline.

6,7-dihydroxy-2-methyl-1-(1-phenylcyclopentyl)-1,2,3,4-tetrahydroisoquinoline.

6,7-dihydroxy-2-methyl-1-(1-phenylcyclohexyl)-1,2,3,4-tetrahydroisoquinoline.

1-[1-(4-chlorophenyl)cyclopropyl]-6,7-dihydroxy-2 -methyl-1,2,3,4-tetrahydroisoquinoline.

1-[1-(4-chlorophenyl)cyclobutyl]-6,7-dihydroxy-2-methyl- 1,2,3,4-tetrahydroisoquinoline.

1-[1-(4-chlorophenyl)cyclopentyl]-6,7-dihydroxy-2 -methyl-1,2,3,4-tetrahydroisoquinoline.

1-[1-(4 -chlorophenyl)cyclohexyl]-6,7-dihydroxy-2-methyl- 1,2,3,4-tetrahydroisoquinoline.

1-[1-(4-chlorophenyl)cyclobutyl]-2-ethyl-6,7-dihydroxy-1,2,3,4-tetrahydroisoquinoline.

2-allyl-1-[1-(4-chlorophenyl)cyclobutyl]-6,7-dihydroxy-1,2,3,4-tetrahydroisoquinoline.

1-[1-(2-chlorophenyl)cyclobutyl]-6,7-dihydroxy-2-methyl- 1,2,3,4-tetrahydroisoquinoline.

1-[1-(3-chlorophenyl)cyclobutyl]-6,7-dihydroxy-2-methyl- 1,2,3,4-tetrahydroisoquinoline.

1-[1-(3,4-dichlorophenyl)cyclobutyl]-6,7-dihydroxy-2 -methyl-1,2,3,4-tetrahydroisoquinoline.

1-[1-(2,4-dichlorophenyl)cyclobutyl]-6,7-dihydroxy-2 -methyl-1,2,3,4-tetrahydroisoquinoline.

1-[1-(4-bromophenyl)cyclobutyl]-6,7-dihydroxy-2-methyl- 1,2,3,4-tetrahydroisoquinoline.

1-[1-(2-bromophenyl)cyclobutyl]-6,7-dihydroxy-2-methyl- 1,2,3,4-tetrahydroisoquinoline.

1-[1-(4-fluorophenyl)cyclobutyl]-6,7-dihydroxy-2-methyl- 1,2,3,4-tetrahydroisoquinoline.

1-[1-(2-fluorophenyl)cyclobutyl]-6,7-dihydroxy-2-methyl- 1,2,3,4-tetrahydroisoquinoline.

6,7-dihydroxy-2-methyl-1-[1-(2-methylthiophenyl)cyclobutyl] -1,2,3,4-tetrahydroisoquinoline.

6,7-dihydroxy-2 -methyl-1-[1-(2-trifluoromethylphenyl)cyclobutyl] -1,2,3,4-tetrahydroisoquinoline.

6,7-dihydroxy-2-methyl-1-[1-(3-trifluoromethylphenyl)cyclobutyl] -1,2,3,4-tetrahydroisoquinoline.

6,7-dihydroxy-2-methyl-1-[1-(o-tolyl)cyclobutyl]- 1,2,3,4-tetrahydroisoquinoline.

6,7-dihydroxy-2-methyl-1-[1-(4 -biphenylyl)cyclobutyl]- 1,2,3,4-tetrahydroisoquinoline.

6,7-dihydroxy-1-[1-(4-methoxyphenyl)cyclobutyl]-2 -methyl-1,2,3,4-tetrahydroisoquinoline.

6,7-dihydroxy-1-[1-(4-hydroxyphenyl)cyclopentyl]-2 -methyl-1,2,3,4-tetrahydroisoquinoline.

1-[1-(2-cyanophenyl)cyclobutyl]-6,7-dihydroxy-2-methyl- 1,2,3,4-tetrahydroisoquinoline.

6,7-dihydroxy-2-methyl-1-[1-(2-naphthyl)cyclobutyl]-1,2,3,4-tetrahydroisoquinoline.

7-hydroxy-6-methoxy-2-methyl-1-(1-phenylcyclobutyl)-1,2,3,4-tetrahydroisoquinoline.

7-hydroxy-6-methoxy-2-methyl-1-(1-phenylcyclopentyl)- 1,2,3,4-tetrahydroisoquinoline.

7-hydroxy-6-methoxy-2-methyl-1-(1-phenylcyclohexyl)-1,2,3,4-tetrahydroisoquinoline.

1-[1-(2-bromophenyl)cyclobutyl]-7-hydroxy-6-methoxy-2 -methyl-1,2,3,4-tetrahydroisoquinoline.

1-[1-(4-chlorophenyl)cyclobutyl]-7-hydroxy-6-methoxy-2 -methyl-1,2,3,4-tetrahydroisoquinoline.

1-[1-(2-chlorophenyl)cyclopropyl]-7-hydroxy-6-methoxy-2 -methyl-1,2,3,4-tetrahydroisoquinoline.

1-[1-(2-chlorophenyl)cyclobutyl]-7-hydroxy-6-methoxy-2 -methyl-1,2,3,4-tetrahydroisoquinoline.

1-[1-(2-chlorophenyl)-3,3-dimethylcyclobutyl]-7-hydroxy-6-methoxy- 2-methyl-1,2,3,4-tetrahydroisoquinoline.

1-[1-(2-chlorophenyl)cyclopentyl]-7-hydroxy-6-methoxy-2 -methyl-1,2,3,4-tetrahydroisoquinoline.

1-[1-(2,4-dichlorophenyl)cyclobutyl]-7-hydroxy-6 -methoxy-2-methyl-1,2,3,4-tetrahydroisoquinoline.

7-hydroxy-6-methoxy-1-[1-(2-methoxyphenyl)cyclopropyl]-2 -methyl-1,2,3,4-tetrahydroisoquinoline.

1-[1-(2-chlorophenyl)cyclopropyl]-7-hydroxy-6-methoxy-2 -(2-hydroxyethyl)-1,2,3,4-tetrahydroisoquinoline.

1-[1-(2-chlorophenyl)cyclopropyl]-7-hydroxy-6-methoxy-2-( 2-methoxyethyl)-1,2,3,4-tetrahydroisoquinoline.

7-hydroxy-6-methoxy-1-[1-(2-methoxyphenyl)cyclobutyl]-2 -methyl-1,2,3,4-tetrahydroisoquinoline.

7-hydroxy-6-methoxy-1-[1-(3-methoxyphenyl)cyclobutyl]-2 -methyl-1,2,3,4-tetrahydroisoquinoline.

7-hydroxy-6-methoxy-2-methyl-1-[1-(4 -trifluoromethoxyphenyl)cyclobutyl]-1,2,3,4-tetrahydroisoquinoline.

1-[1-(2,3-dihydrobenzo[b]furan-7-yl)cyclopropyl]-7-hydroxy -6-methoxy -2-methyl-1,2,3,4-tetrahydroisoquinoline.

7-hydroxy-6-methoxy-2-methyl-1-[1-(1-naphthyl)cyclopropyl] -1,2,3,4-tetrahydroisoquinoline.

1-[1-(2-bromo-4,5-dimethoxyphenyl)cyclobutyl]-7-hydroxy- 6-methoxy-2-methyl-1,2,3,4-tetrahydroisoquinoline.

1-[1-(2-chlorophenyl)cyclobutyl]-7-hydroxy-2-methyl-6 -phenyl-1,2,3,4-tetrahydroisoquinoline.

6-fluoro-7-hydroxy-2-methyl-1-(1-phenylcyclobutyl)-1,2,3,4-tetrahydroisoquinoline.

1-[1-(4-chlorophenyl)cyclobutyl]-6-fluoro-7-hydroxy-2 -methyl-1,2,3,4-tetrahydroisoquinoline.

1-[1-(2-chlorophenyl)cyclobutyl]-6-fluoro-7-hydroxy-2 -methyl-1,2,3,4-tetrahydroisoquinoline.

1-[1-(2-chlorophenyl)cyclopropyl]-6-fluoro-7-hydroxy-2 -methyl-1,2,3,4-tetrahydroisoquinoline.

1-[1-(2,4-dichlorophenyl)cyclobutyl]-6-fluoro-7-hydroxy- 2-methyl-1,2,3,4-tetrahydroisoquinoline.

1-[1-(2,4-dichlorophenyl)cyclopropyl]-6-fluoro-7 -hydroxy-2-methyl-1,2,3,4-tetrahydroisoquinoline.

1-[1-(4-bromophenyl)cyclobutyl]-6-fluoro-7-hydroxy-2 -methyl-1,2,3,4-tetrahydroisoquinoline.

1-[1-(2-bromophenyl)cyclobutyl]-6-fluoro-7-hydroxy-2 -methyl-1,2,3,4-tetrahydroisoquinoline.

6-chloro-7-hydroxy-2-methyl-1-(1-phenylcyclobutyl)-1,2,3,4-tetrahydroisoquinoline.

2-allyl-6-chloro-7-hydroxy-1-(1-phenylcyclobutyl)- 1,2, 3,4-tetrahydroisoquinoline.

6-chloro-7-hydroxy-2-methyl-1-(3,3-dimethyl-1 -phenylcyclobutyl)-1,2,3,4-tetrahydroisoquinoline.

6-chloro-1-[1-(4-chlorophenyl)cyclobutyl]-7-hydroxy-2 -methyl-1,2,3,4-tetrahydroisoquinoline.

6-chloro-1-[1-(2-chlorophenyl)cyclobutyl]-7-hydroxy-2-methyl-1,2,3,4-tetrahydroisoquinoline.

1-[1-(2-bromophenyl)cyclobutyl]-6-chloro-7-hydroxy-2-methyl-1,2,3,4-tetrahydroisoquinoline.

7-chloro-6-hydroxy-2-methyl-1-(1-phenylcyclobutyl)-1,2,3,4-tetrahydroisoquinoline.

5-chloro-8-hydroxy-2-methyl-1-(1-phenylcyclobutyl)-1,2,3,4-tetrahydroisoquinoline.

5-chloro-6,7-dihydroxy-2-methyl-1-(1-phenylcyclobutyl)- 1,2,3,4-tetrahydroisoquinoline.

6,8-dichloro-7-hydroxy-2-methyl-1-(1-phenylcyclobutyl)- 1,2,3,4-tetrahydroisoquinoline.

7-hydroxy-2-methyl-6-nitro-1-(1-phenylcyclobutyl)- 1,2,3,4-tetrahydroisoquinoline.

6-bromo-7-hydroxy-2-methyl-1-(1-phenylcyclobutyl)-1,2,3,4-tetrahydrosoqunoline.

1-[1-(2-chlorophenyl)cyclopropyl]-7-hydroxy-2-methyl-1,2,3,4-tetrahydroisoquinoline.

7-hydroxy-2-methyl-1-(1-phenylcyclobutyl)-1,2,3,4-tetrahydroisoquinoline.

1-[1-(4-chlorophenyl)cyclobutyl]-7-hydroxy-2-methyl-1,2,3,4-tetrahydroisoquinoline.

1-[1-(2-chlorophenyl)cyclobutyl]-7-hydroxy-2-methyl-1,2,3,4-tetrahydroisoquinoline.

1-[1-(2-chlorophenyl)cyclopropyl]-7-hydroxy-2,6-dimethyl-1,2,3,4-tetrahydroisoquinoline.

1-[1-(2-chlorophenyl)cyclobutyl]-7-hydroxy-2,6-dimethyl- 1,2,3,4-tetrahydroisoquinoline.

1-[1-(4-chlorophenyl)cyclobutyl]-5-hydroxy-2-methyl-1,2,3,4-tetrahydroisoquinoline.

and pharmaceutically acceptable salts thereof in the form of individual enantiomers, racemates or other mixtures of enantiomers.

Compounds of formula I, II and III may exist as salts with pharmaceutically acceptable acids. Examples of such salts include hydrochlorides, hydrobromides, hydriodides, sulphates, nitrates, maleares, acetates, citrates, fumarates, tartrates, succinates, benzoates, pamoates, methylsulphates, dodecanoates and salts with acidic amino acids such as glutamic acid. Compounds of formula I, II and III and their salts may exist in the form of solyates (for example hydrates).

Compounds of formula III have high lipid solubility, and are therefore suitable for use in the so-called depot formulations which provide a source of active compound which is located within the body (eg by intramuscular injection). These compounds may be formulated in a pharmaceutically acceptable oil.

Specific compounds of formula III are:

1-[1-(2-chlorophenyl)cyclopropyl]-7-heptanoyloxy-6-methoxy-2-methyl-1,2,3,4-tetrahydroisoquinoline 1-[1-(2-chlorophenyl)cyclopropyl]-7-decanoyloxy-6-methoxy-2-methyl-1,2,3,4-tetrahydroisoquinoline 1-[1-(2-chlorophenyl)cyclopropyl]-7-dodecanoyloxy-6-methoxy-2-methyl-1,2,3,4-tetrahydroisoquinoline 1-[1-(2-chlorophenyl)cyclopropyl]-7-hexadecanoyloxy-6-methoxy-2-methyl-1,2,3,4-tetrahydroisoquinoline 1-[1-(2-chlorophenyl)cyclopropyl]-7-octadecanoyloxy-6-methoxy-2-methyl-1,2,3,4-tetrahydroisoquinoline 1-[1-(2-chlorophenyl)cyclopropyl]-7-decanoyloxy-6-fluoro-2-methyl-1,2,3,4-tetrahydroisoquinoline 1-[1-(2-chlorophenyl)cyclobutyl]-7-decanoyloxy-6-fluoro- 2-methyl-1,2,3,4-tetrahydroisoquinoline and pharmaceutically acceptable salts thereof in the form of individual enantiomers, racemates or other mixtures of enantiomers.

It will be appreciated by those skilled in the art that compounds of formula I, II and III contain a chiral centre. When a compound of formula I, II and III contains a single chiral centre it exists in two enantiomeric forms. The present invention includes the individual enantiomers and mixtures of those enantiomers. The enantiomers may be obtained by methods known to those skilled in the art. Such methods typically include resolution via formation of diastereoisomeric salts which may be separated, for example, by crystallisation; via formation of diastereoisomeric derivatives or complexes which may be separated, for example, by crystallisation, gas-liquid or liquid chromatography; selective reaction of one enantiomer with an enantiomer-specific reagent, for example enzymatic esterification, oxidation or reduction; or gas-liquid or liquid chromatography in a chiral environment, for example on a chiral support such as silica with a bound chiral ligand or in the presence of a chiral solvent. It will be appreciated that where the desired enantiomer is converted into another chemical entity by one of the separation processes described above, a further step will subsequently be required to liberate the desired enantiomeric form. Alternatively, specific enantiomers may be synthesised by asymmetric synthesis using optically active reagents, substrates, catalysts or solvents, or by converting one enantiomer into the other by asymmetric transformation.

Specific enantiomeric forms of compounds of formula I are:

(−)-6-chloro-7-hydroxy-2-methyl-1-(1-phenylcyclobutyl)- 1,2,3,4-tetrahydroisoquinoline (+)-1-[1-(2-bromophenyl)cyclobutyl]-6,7-dihydroxy-2-methyl-1,2,3,4-tetrahydroisoquinoline hydrobromide (+)-1-[1-(2-chlorophenyl)cyclobutyl]-6-fluoro-7-hydroxy- 2-methyl-1,2,3,4-tetrahydroisoquinoline hydrobromide (+)-1-[1-(2-chlorophenyl)cyclopropyl]-6-fluoro-7 -hydroxy-2-methyl-1,2,3,4-tetrahydroisoquinoline hydrobromide (+)-1-[1-(2-chlorophenyl)cyclopropyl]-7-hydroxy-6-methoxy-2-methyl-1,2,3,4-tetrahydroisoquinoline hydrobromide (+)-1-[1-(2-chlorophenyl)cyclopropyl]-7-hydroxy-2,6-dimethyl-1,2,3,4-tetrahydroisoquinoline hydrobromide (+)-1-[1-(2-chlorophenyl)cyclopropyl]-7-heptanoyloxy-1,2,3,4-tetrahydroisoquinoline (+)-1-[1-(2-chlorophenyl)cyclopropyl]-7-decanoyloxy-6-methoxy-2-methyl-1,2,3,4-tetrahydroisoquinoline (+)-1-[1-(2-chlorophenyl)cyclopropyl]-7-dodecanoyloxy-6-methoxy-2-methyl-1,2,3,4-tetrahydroisoquinoline (+)-1-[1-(2-chlorophenyl)cyclopropyl]-7-hexadecanoyloxy- 6-methoxy-2-methyl-1,2,3,4-tetrahydroisoquinoline (+)-1-[1-(2-chlorophenyl)cyclopropyl]-7-octadecanoyloxy- 6-methoxy-2-methyl-1,2,3,4-tetrahydroisoquinoline (−)-1-[1-(2-chlorophenyl)cyclobutyl]-7-decanoyloxy-6-fluoro-2-methyl-1,2,3,4-tetrahydroisoquinoline (+)-1-[1-(2-chlorophenyl)cyclopropyl]-7-decanoyloxy-6-fluoro-2-methyl-1,2,3,4-tetrahydroisoquinoline.

When a compound of formula I, II or III contains more than one chiral centre it may exist in diastereoisomeric forms. The diastereoisomeric pairs may be separated by methods known to those skilled in the art, for example chromatography or crystallisation and the individual enantiomers within each pair may be separated as described above. The present invention includes each diastereoisomer of compounds of formula I or II and mixtures thereof.

Certain compounds of formula I, II or III may exist in more than one crystal form and the present invention includes each crystal form and mixtures thereof.

The present invention also provides pharmaceutical compositions comprising a therapeutically effective amount of a compound of formula I, II or III together with a pharmaceutically acceptable diluent or carrier. Such pharmaceutical formulations may be used in analgesia and in the treatment of psychoses (for example schizophrenia), Parkinson's disease, Lesch-Nyan syndrome, attention deficit disorder or cognitive impairment or in the relief of drug dependence or tardive dyskinesia.

In therapeutic use, the active compound may be administered orally, rectally, parenterally or topically, preferably orally. Thus the therapeutic compositions of the present invention may take the form of any of the known pharmaceutical compositions for oral, rectal, parenteral or topical administration. Pharmaceutically acceptable carriers suitable for use in such compositions are well known in the art of pharmacy. The compositions of the invention may contain 0.1–90% by weight of active compound. The compositions of the invention are generally prepared in unit dosage form.

Compositions for oral administration are the preferred compositions of the invention and these are the known pharmaceutical forms for such administration, for example tablets, capsules, granules, syrups, solutions and aqueous or oil suspensions. The excipients used in the preparation of these compositions are the excipients known in the pharmacist's art. Tablets may be prepared from a mixture of the active compound with fillers, for example calcium phosphate; disintegrating agents, for example maize starch; lubricating agents, for example magnesium stearate; binders, for example micro-crystalline cellulose or polyvinylpyrrolidone and other optional ingredients known in the art to permit tableting the mixture by known methods. The tablets may, if desired, be coated using known methods and excipients which may include enteric coating using for example hydroxypropylmethylcellulose phthalate. The tablets may be formulated in a manner known to those skilled in the art so as to give a sustained release of the compounds of the present invention. Such tablets may, if desired, be provided with enteric coatings by known methods, for example by the use of cellulose acetate phthalate. Similarly, capsules, for example hard or soft gelatin capsules, containing the active compound with or without added excipients, may be prepared by known methods and, if desired, provided with enteric coatings in a known manner. The contents of the capsule may be formulated using known methods so as to give sustained release of the active compound. The tablets and capsules may conveniently each contain 1 to 500 mg of the active compound.

Other compositions for oral administration include, for example, aqueous suspensions containing the active compound in an aqueous medium in the presence of a non-toxic suspending agent such as sodium carboxymethylcellulose, and oily suspensions containing a compound of the present invention in a suitable vegetable oil, for example arachis oil. The active compound may be formulated into granules with or without additional excipients. The granules may be ingested directly by the patient or they may be added to a suitable liquid carrier (for example, water) before ingestion. The granules may contain disintegrants, eg an effervescent couple formed from an acid and a carbonate or bicarbonate salt to facilitate dispersion in the liquid medium.

Compositions of the invention suitable for rectal administration are the known pharmaceutical forms for such administration, for example, suppositories with hard fat or polyethylene glycol bases.

Compositions of the invention suitable for parenteral administration are the known pharmaceutical forms for such administration, for example sterile suspensions or sterile solutions in a suitable solvent.

Compositions for topical administration may comprise a matrix in which the pharmacologically active compounds of the present invention are dispersed so that the compounds are held in contact with the skin in order to administer the compounds transdermally. Alternatively the active compounds may be dispersed in a pharmaceutically acceptable cream, gel or ointment base. The amount of active compound contained in a topical formulation should be such that a therapeutically effective amount of the compound is delivered during the period of time for which the topical formulation is intended to be on the skin.

The compounds of the present invention may also be administered by continuous infusion either from an external source, for example by intravenous infusion or from a source of the compound placed within the body. Internal sources include implanted reservoirs containing the compound to be infused which is continuously released for example by osmosis and implants which may be (a) liquid such as a suspension or solution in a pharmaceutically acceptable oil of the compound to be infused for example in the form of a very sparingly water-soluble derivative such as a dodecanoate salt or a compound of formula III as described above or (b) solid in the form of an implanted support, for example of a synthetic resin or waxy material, for the compound to be infused. The support may be a single body containing all the compound or a series of several bodies each containing part of the compound to be delivered. The amount of active compound present in an internal source should be such that a therapeutically effective amount of the compound is delivered over a long period of time.

In some formulations it may be beneficial to use the compounds of the present invention in the form of particles of very small size, for example as obtained by fluid energy milling.

In the compositions of the present invention the active compound may, if desired, be associated with other compatible pharmacologically active ingredients.

The pharmaceutical compositions containing a therapeutically effective amount of a compound of formula I, II or III may be used in analgesia or to treat psychoses (for example schizophrenia), Parkinson's disease, Lesch-Nyan syndrome, attention deficit disorder or cognitive impairment or in the relief of drug dependence or tardive dyskinesia. In such treatment the amount of the compound of formula I or II which will be administered orally, rectally or parenterally per day is in the range 0.1 to 5000 mg preferably 5 to 500 mg given in a single or in divided doses at one or more times during the day.

Processes for the preparation of compounds of formula I will now be described. These processes form a further aspect of the present invention.

Compounds of formula I may be prepared by the cleavage of compounds of formula IV

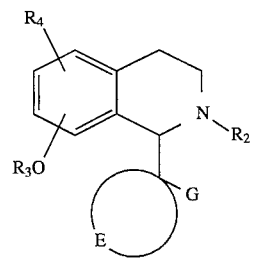

IV in which $R_3$ is an optionally substituted alkyl group (e.g. methyl or benzyl) and $R_4$ is the group $R_1$ or a group which can be converted into the group $R_1$. Demethylation may be effected by the reaction with hydrobromic acid optionally in the presence of glacial acetic acid, with boron tribromide, with pyridine hydrochloride, with sodium methanethiolate or with trimethyliodosilane. Debenzylation may be effected by hydrolysis e.g. acid hydrolysis or by hydrogenolysis, for example using a palladium/charcoal catalyst. Compounds of formula I in which $R_1$ is hydroxy may be prepared by cleavage of compounds of formula IV in which the groups $OR_3$ and $R_4$ are the same (e.g. methoxy or benzyloxy). The cleavage of the group $R_4$ will occur simultaneously with the cleavage of the group $OR_3$.

Compounds of formula I may be prepared by the alkylation or alkenylation of compounds of formula V

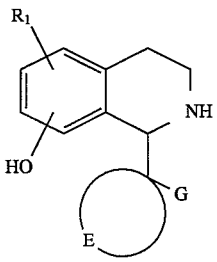

under conditions which do not result in alkylation or alkenylation of the hydroxy group. For example, compounds of formula I in which $R_2$ is methyl may be prepared by the methylation of compounds of formula V, for example, using formaldehyde and formic acid or formaldehyde and sodium cyanoborohydride.

Compounds of formula I in which $R_1$ is other than H may be prepared by substitution reactions which will be well known to those skilled in the art. For example, compounds of formula I in which $R_1$ is nitro may be prepared by the nitration of compounds of formula I in which $R_1$ is H using nitric acid and compounds of formula I in which $R_1$ represents one or more chloro atoms may be prepared from compounds of formula I in which $R_1$ is H by chlorination using, for example sodium hypochlorite and hydrochloric acid.

Compounds of formula II may be prepared by methods analogous to those described above for the preparation of compounds of formula I.

Compounds of formula III may be prepared from compounds of formula I by reaction with an acylating agent for example a carboxylic acid chloride of formula $R_7Cl$ or a carboxylic anhydride of formula $(R_7)_2O$.

Compounds of formula IV may be prepared by the alkylation or alkenylation of compounds of formula VI

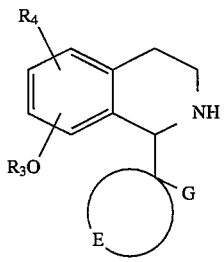

for example by reaction with an alkyl halide (e.g. methyl iodide) or an alkenyl halide (e.g. allyl iodide or bromide). Compounds of formula IV may be prepared by reductive alkylation of compounds of formula VI, for example, by reaction with an aldehyde or ketone and a reducing agent. For example, compounds of formula IV in which $R_2$ is methyl may be prepared by the methylation of compounds of formula VI, for example, using formaldehyde and formic acid, formaldehyde and sodium dihydrogen phosphite or formaldehyde and sodium cyanoborohydride.

Compounds of formula IV in which $R_2$ is methyl may be prepared by the reaction of compounds of formula VII

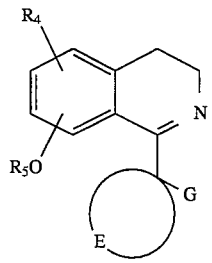

in which $R_5$ is the group $R_3$ under conditions which result in the reduction and methylation of the compound of formula VII, for example by the reaction of the compound of formula VII with formaldehyde and a reducing agent such as sodium cyanoborohydride.

Compounds of formula IV may be prepared by the reaction of compounds of formula VIII

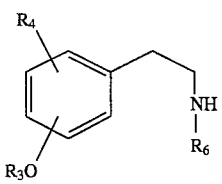

in which $R_6$ is the group $R_2$ with a compound of formula IX

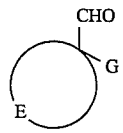

in the presence of an acid, for example hydrochloric acid.

Compounds of formula IV may be prepared by the reduction of compounds of formula X

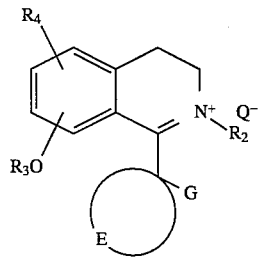

in which $Q^{\ominus}$ is a suitable anion such as iodide or methylsulphate with, for example, sodium borohydride, sodium cyanoborohydride, borane, borane-dimethylsulphide complex, lithium aluminium hydride or by catalytic hydrogenation. Chiral reducing agents such as chiral sodium triacyloxyborohydrides {for example the appropriate enantiomers of tris(N-benzyloxycarbonylprolyloxy)borohydride or tris [N-(2-methylpropyloxycarbonyl)prolyloxy] borohydride}, chiral dialkyloxyboranes, chiral oxazaborolidines may be used to give one of the enantiomers of the compound of formula IV. One of the enantiomers of compounds of formula IV may be prepared by catalytic hydrogenation using a chiral catalyst. A suitable catalyst is the complex formed by the reaction of a chiral phosphine [for example, 2,3-O-isopropylidene- 2,3-dihydroxy-1,4-bis(diphenylphosphino)butane] with a transition metal complex [for example, chloro(1,5-cyclooctadiene)rhodium (I) dimer].

Compounds of formula V may be prepared by the cleavage of compounds of formula VI in which $R_4$ is the group $R_1$ or a group which can be converted into the group $R_1$ in a similar manner to that described above in respect of compounds of formula I.

Compounds of formula V may be prepared by the reduction of compounds of formula VII in which $R_5$ is H, for example using reduction reactions similar to those described above for the reduction of compounds of formula X. Chiral reducing agents may be used to give one of the enantiomers of the compound of formula V in a similar manner to that described above for the reduction of compounds of formula X.

Compounds of formula VI may be prepared by the reduction of compounds of formula VII in which $R_5$ is the group $R_3$ in a similar manner to that described above for the preparation of compounds of formula IV and V.

Compounds of formula VI may be prepared by reduction of compounds of formula XI

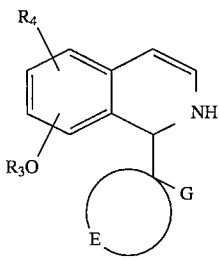

XI for example using catalytic hydrogenation.

Compounds of formula VI may be prepared by the reaction of a compound of formula VIII in which $R_6$ is H with a compound of formula IX in the presence of an acid for example hydrochloric acid.

Compounds of formula VII may be prepared by the cyclisation of compounds of formula XII

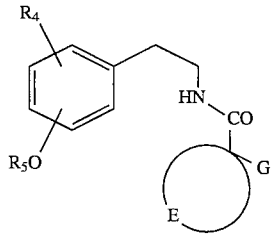

XII in which $R_5$ is H or $R_3$. The cyclisation may be effected in the presence of a condensing agent such as phosphorus oxychloride, phosphorus pentoxide, phosphorus pentachloride, polyphosphoric ester, polyphosphoric acid, zinc chloride, hydrochloric acid, thionyl chloride or sulphuric acid.

Compounds of formula VII may be prepared by the reaction of a compound of formula XIII

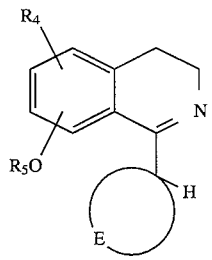

XIII with a halo-substituted group of formula X-G in which X is halo (for example fluoro) in the presence of a base such as lithium diisopropylamide.

Compounds of formula IX may be prepared by reduction of arylcycloalkanecarbonitriles of formula XIV

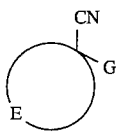

XIV by di-t-butylaluminium hydride or di-isobutyl aluminium hydride or reduction of arylcycloalkane carbonyl chlorides of formula XV

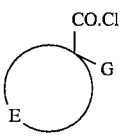

XV with tri-t-butoxy aluminohydride.

Compounds of formula X may be prepared by the reaction of a compound of formula VII in which $R_5$ is the group $R_3$ with an alkylating agent of formula $R_2Q$, for example methyl iodide or dimethylsulphate.

Compounds of formula XI may be prepared by the cyclisation of compounds of formula XVI

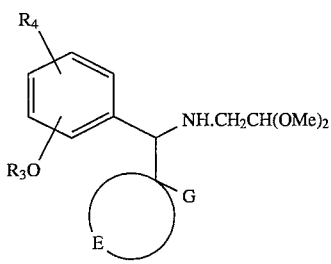

XVI

The cyclisation may be effected in the presence of an acid such as sulphuric acid.

Compounds of formula XII may be prepared by the reaction of a phenethylamine of formula XVII

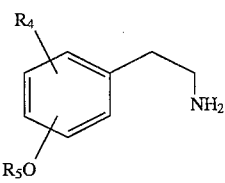

XVII in which $R_5$ is H or $R_3$ with an arylcycloalkanecarbonyl chloride of formula XV for example in the presence of an organic base such as triethylamine. Compounds of formula XII may be prepared by the condensation of a phenethylamine of formula XVII with an arylcycloalkane carboxylic acid of formula XVIII

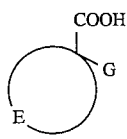

XVIII or an ester thereof, for example by fusion or by the action of a condensing agent such as carbonyldiimidazole.

Compounds of formula XIII may be prepared by cyclisation of compounds of formula XIX

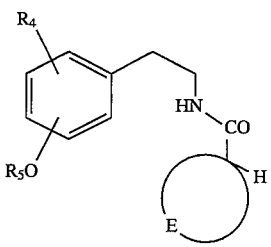
XIX under conditions similar to those described above for the cyclisation of compounds of formula XII.

Arylcycloalkanecarbonitriles of formula XIV may be prepared by the reaction of an arylacetonitrile of formula XX

G—CH$_2$—CN    XX with a dihalo compound of formula XXI

Z—E—Z'    XXI in which Z and Z', which may be the same or different, are leaving groups such as halo e.g. chloro or bromo in the presence of a base such as sodium hydride or potassium hydroxide.

Arylcycloalkanecarbonyl chlorides of formula XV may be prepared from arylcycloalkane carboxylic acids of formula XVIII by methods which are well known in the art, for example, by reaction with thionyl chloride.

Compounds of formula XVI may be prepared by the reaction of a compound of formula XXII

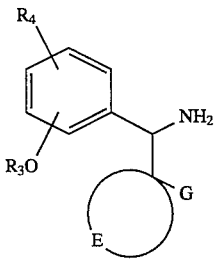
XXII with a haloacetaldehyde dimethylacetal for example chloroacetaldehyde dimethylacetal.

Arylcycloalkane carboxylic acids of formula XVIII may be prepared by the hydrolysis (e.g. basic hydrolysis) of arylcycloalkanecarbonitriles of formula XIV or by the reaction of hydrogen peroxide with arylcycloalkanecarbonitriles of formula XIV in the presence of a base followed by reaction with nitrous acid to give the required carboxylic acid.

Compounds of formula XIX may be prepared by the reaction of a phenylethylamine of formula XVII with a cycloalkane carbonyl chloride of formula XXIII

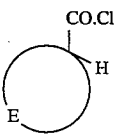
XXIII

Compounds of formula XXII may be prepared by the reaction of a compound of formula XXIV

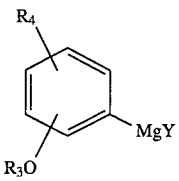
XXIV in which Y is halo (eg chloro or bromo) with an arylcycloalkanecarbonitrile of formula XIV followed by reduction with, for example, sodium borohydride.

Compounds of formula XXIV may be prepared by the reaction of magnesium with a compound of formula XXV

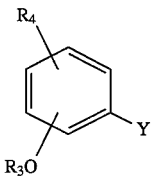
XXV in which Y is halo (eg bromo or chloro).

The ability of compounds of formula I or formula II to interact with dopamine receptors has been demonstrated by the following tests which determine the ability of the compounds to inhibit tritiated ligand binding to dopamine receptors in vitro and in particular to the D1 and D2 dopamine receptors.

Striatal samples from the brains of male Charles River CD rats weighing between 140–250 g were homogenised in ice-cold 50 mM Tris-HCl buffer (pH 7.4 when measured at 25° C. for D1 binding assays and pH 7.7 when measured at 25° C. for D2 binding assays) and centrifuged for 10 minutes (at 21,000 g when used for D1 binding assay and 40,000 g when used for D2 binding assays). The pellet was resuspended in the same buffer, again centrifuged and the final pellet stored at −80° C. Before each test the pellet was resuspended in 50 mM Tris-HCl buffer containing 120 mM NaCl, 5 mM KCl, 2 mM CaCl$_2$ and 1 mM MgCl$_2$ at pH 7.4 for the D1 binding assays and at pH 7.7 with the addition of 6 mM ascorbic acid for the D2 binding assays. Aliquots of this suspension were then added to tubes containing the ligand and either the compound under test or buffer. For the D1 binding assays the ligand was tritiated SCH 23390 and the mixture was incubated at 37° C. for 30 minutes before the incubation was terminated by rapid filtration. For the D2 binding assays the ligand was tritiated (S)-sulpiride and the mixture was incubated at 4° C. for 40 minutes before the incubation was terminated by rapid filtration. Non-specific binding was determined experimentally by the addition of saturating concentrations of chloropromazine or spiroperidol for D1 and D2 receptors respectively.

The filters were washed with ice-cold Tris-HCl buffer and dried. The filters were punched out on to vials containing scintillation fluid and were left for about 20 hours before being counted by scintillation spectrophotometry. Displacement curves were produced over a range of concentrations of the compound under test and the concentration which gave a 50% inhibition of specific binding (IC50) obtained from the curve. The inhibition coefficient Ki was then calculated using the formula $$K_i = \frac{IC50}{1 + ([\text{ligand}]/K_D)}$$

in which [ligand] is the concentration of the tritiated ligand used and $K_D$ is the equilibrium dissociation constant for the ligand.

The $K_i$ values obtained in the above tests for D1 and D2 binding for each of the final products of Examples 1 to 85 hereinafter are given in Table I below which also shows the ratio between these two values to two significant figures. In some cases $K_i$ values for D2 binding were estimated from single concentration data by the application of the Langmuir adsorption isotherm equation. These cases are indicated by an "E" in the last two columns of Table I. In other cases it was not possible to determine or estimate the $K_i$ and the $K_i$ value is given as greater than (>) that which would result from the application of the above formula to the highest concentration which displaced ≦50% of the ligand.

TABLE I

| Example | $K_i$ for D1 binding (nM) | $K_i$ for D2 binding (nM) | $\frac{K_i \text{ for D2}}{K_i \text{ for D1}}$ |
|---|---|---|---|
| 1 | 4.0 | 1000 | 250 |
| 2 | 7.2 | 12000 | 1700 |
| 3 | 22 | 6100000 | 280000 |
| 4 | 29 | 260000 | 9000 |
| 5 | 8.3 | 32000 | 3900 |
| 6 | 3 | 41000 | 14000 |
| 7 | 21 | 2900 | 140 |
| 8 | 310 | >5000 | >16 |
| 9 | 1.9 | 1800 | 950 |
| 10 | 1.6 | 2500 | 1600 |
| 11 | 150.0 | 3500 | 23 |
| 12 | 1.4 | 710 | 510 |
| 13 | 44 | 3700 | 84 |
| 14 | 120 | 4800 | 40 |
| 15 | 200 | >5000 | >25 |
| 16 | 180 | 3200 | 18 |
| 17 | 3.9 | 8900 | 2300 |
| 18 | 83 | 4400 | 53 |
| 19 | 190 | 7000E | 37E |
| 20 | 31 | >5000 | >160 |
| 21 | 200 | >5000 | >25 |
| 22 | 2.3 | 1800 | 780 |
| 23 | 18 | 15000 | 830 |
| 24 | 1.9 | 1700 | 890 |
| 25 | 19 | 5400000 | 280000 |
| 26 | 560 | 7000E | 13E |
| 27 | 190 | 5700 | 30 |
| 28 | 11 | 3600 | 330 |
| 29 | 120 | 7000E | 58E |
| 30 | 66 | >5000 | >76 |
| 31 | 540 | 11000E | 20E |
| 32 | 140 | >5000 | >36 |
| 33 | 65 | 23000 | 350 |
| 34 | 1.8 | 7800 | 4300 |
| 35 | 1.3 | 240000 | 180000 |
| 36 | 62 | 4400 | 71 |
| 37 | 0.6 | 5300 | 8800 |
| 38 | 4.1 | 3400 | 830 |
| 39 | 23 | 1900 | 83 |
| 40 | 0.4 | 18000 | 45000 |
| 41 | 79 | 13000 | 160 |
| 42 | 170 | 2500 | 15 |
| 43 | 1.4 | 860 | 610 |
| 44 | 130 | 4800 | 37 |
| 45 | 24 | >500 | >21 |
| 46 | 6.6 | 1200 | 180 |
| 47 | 9.1 | 19000 | 2100 |
| 48 | 94 | 3000E | 32E |
| 49 | 8.4 | >500 | >60 |
| 50 | 25 | 1500 | 60 |
| 51 | 13 | >500 | >38 |
| 52 | 17 | 5400 | 320 |
| 53 | 24 | 7600 | 320 |
| 54 | 32 | 3000 | 94 |
| 55 | 41 | >500 | >12 |
| 56 | 2.3 | 52000 | 23000 |
| 57 | 770 | >5000 | >6.5 |

TABLE I-continued

| Example | $K_i$ for D1 binding (nM) | $K_i$ for D2 binding (nM) | $\frac{K_i \text{ for D2}}{K_i \text{ for D1}}$ |
|---|---|---|---|
| 58 | 740 | 360000 | 490 |
| 59 | 5.2 | 3200 | 620 |
| 60 | 2.8 | 2000 | 710 |
| 61 | 0.18 | 450 | 2500 |
| 62 | 0.38 | 410 | 1100 |
| 63 | 2.0 | 1600 | 800 |
| 64 | 2.4 | 4800 | 2000 |
| 65 | 22 | 51000 | 2300 |
| 66 | 120 | >500 | >4.2 |
| 67 | 53 | 7000E | 130E |
| 68 | 2 | 1900 | 950 |
| 69 | 2.1 | 5800 | 2800 |
| 70 | 21 | 35000 | 1700 |
| 71 | 1.5 | 1800 | 1200 |
| 72 | 47 | 9500 | 200 |
| 73 | 0.9 | 5000 | 5500 |
| 74 | 1.5 | 1100 | 730 |
| 75 | 150.0 | >5000 | >33 |
| 76 | 60.0 | >5000 | >83 |
| 77 | 0.28 | 900 | 3200 |
| 78 | 94 | 550 | 5.9 |
| 79 | 1.2 | 940 | 780 |
| 80 | 0.67 | 370 | 550 |
| 81 | 1.9 | 330 | 170 |
| 82 | 1.8 | 4900 | 2700 |
| 83 | 21 | 6600E | 310E |
| 84 | 12 | 5100 | 430 |
| 85 | 0.28 | 900 | 3200 |

The invention is illustrated by the following Examples which are given by way of example only. In these Examples all temperatures are given in degrees Celsius. The final products of each of these Examples were characterised by one or more of the following procedures: elemental analyses, nuclear magnetic resonance spectroscopy and infra red spectroscopy.

EXAMPLES 1 to 11

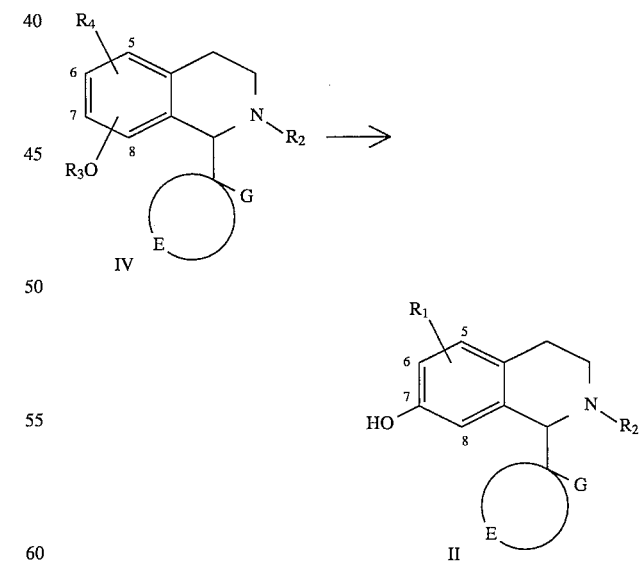

A compound of formula IV (a g, prepared as described in the Example identified in column SM) in which $R_2$ is methyl, $OR_3$ and $R_4$ are as defined in Table A and E is —$(CH_2)_3$— was heated under reflux with 48% aqueous hydrobromic acid (b ml) and glacial acetic acid (c ml) for d hours to give a compound of formula II in which $R_1$ is as defined in Table A, $R_2$ is methyl and E is —$(CH_2)_3$—. The solvent was removed by evaporation and the residue dried by repeated azeotropic distillation with propan-2-ol. The product was isolated as its hydrobromide salt (the melting point in degrees Celsius is given in the column headed "mp"). The isolation procedure and any other variations from the above procedure are identified in the column headed "Note".

NOTES TO TABLE A

A1 The product was precipitated from its concentrated solution in propan-2-ol.

A2 The residue from the azeotropic distillation was dried in vacuo at 100° C. for 2½ hours, then decolourised with charcoal in propan-2-ol, washed with ether, propan-2-ol (1–2ml) and ether and dried in vacuo.

A3 The residue from the azeotropic distillation was recrystallised from propan-2-ol to give the desired product.

A4 The residue from the azeotropic distillation gave the desired product which was used without further purification.

A5 The reaction was conducted under nitrogen. The residue from the azeotropic distillation was partitioned between ether and saturated aqueous sodium bicarbonate solution. The ether layer was dried and treated with oxalic acid. The resulting oxalate salt was collected by filtration, washed with ether and dried at 50° C. in vacuo. The melting point of the oxalate salt is given in the last column of Table A.

A6 The reaction was conducted under nitrogen. The residue after the azeotropic distillation was decolourised with charcoal in methanol and the resulting material dried by azeotropic distillation with propan-2-ol. The resulting residue was decolourised with charcoal in ethanol. The solution yielded the product on evaporation.

A7 The residue after azeotropic distillation was decolourised with charcoal in methanol. The residue was partitioned between ether and saturated aqueous sodium bicarbonate solution. The ether layer was treated with an ethereal solution of oxalic acid. The resulting solid was washed with ether and dried in vacuo. The melting point of the oxalate salt is given in the last column of Table A.

A8 The reaction was conducted under nitrogen. The residue resulting from the removal of the solvent from the reaction mixture was dissolved in industrial methylated spirit and decolourised with charcoal. The solvent was removed and the residue washed with ether, dissolved in ethanol, and decolourised with charcoal. Concentration of the solution yielded the desired product which was washed with ether.

A9 The reaction was conducted under nitrogen. The solvent was removed from the reaction mixture by distillation and the residue dissolved in methanol and decolourised with charcoal. Filtration and evaporation gave a residue which was dried by azeotropic distillation with propan-2-ol. The product was crystallised from propan-2-ol, collected by filtration, washed with ether and dried in vacuo at 80° C.

A10 The residue from the azeotropic distillation was partitioned between ether and saturated aqueous sodium bicarbonate solution. The ether layer yielded a residue which was heated under reflux with 48% aqueous hydrobromic acid (15 ml) and glacial acetic acid (15 ml) for 5 hours. The reaction mixture was neutralised with saturated aqueous sodium bicarbonate solution and extracted with ether. The ether extract was washed with 1M hydrochloric acid. The washings yielded a solid which was dried in vacuo at 70° C., basified and extracted with ether. The extract gave a residue which was dissolved in ethanol and treated with ethereal oxalic acid to Give the desired product in the form of its oxalate salt, the melting point of which is given in the last column of Table A.

A11 The reaction was conducted under nitrogen. The residue after the azeotropic distillation was decolourised with charcoal in methanol and the resulting material triturated with propan-2-ol. The solid was crystallised from ether, collected by filtration, washed with ether and dried in vacuo at 50° C.

TABLE A

| Ex | $R_1$ | G | SM | $OR_3$ | $R_4$ | a | b | c | d | Note | mp (°C.) |
|---|---|---|---|---|---|---|---|---|---|---|---|
| 1 | 6-OH | 2-bromophenyl | MF1 | 7-OMe | 6-OMe | 2.1 | 20 | 20 | 16 | A1 | 199–202 |
| 2 | 6-OH | 2-chlorophenyl | MF2 | 7-OMe | 6-OMe | 4.6 | 25 | 25 | 16 | A2 | 192 |
| 3 | 6-OH | 4-fluorophenyl | MF3 | 7-OMe | 6-OMe | 5.9 | 30 | 30 | 16 | A3 | 134 (dec) |
| 4 | 6-OH | 2-methylphenyl | MF4 | 7-OMe | 6-OMe | 4.5 | 25 | 25 | 16 | A4 | 145 (dec) |
| 5 | 6-F | 4-chlorophenyl | MI1 | 7-OMe | 6-F | 3.5 | 20 | 20 | 8 | A5 | 197–200 (dec) |
| 6 | 6-F | 4-bromophenyl | MI2 | 7-OMe | 6-F | 2.7 | 20 | 20 | 4 | A6 | 140–145 |
| 7 | 6-OH | 2-fluorophenyl | MF5 | 7-OMe | 6-OMe | 1.4 | 25 | 25 | 4 | A7 | 155–158 (dec) |
| 8 | 6-OH | 3-trifluoromethylphenyl | MI3 | 7-OMe | 6-OMe | 8.8 | 30 | 20 | 2.5 | A8 | 148–150 |
| 9 | 6-F | 2,4-dichlorophenyl | MI4 | 7-OMe | 6-F | 2.7 | 20 | 20 | 4 | A9 | 237–240 |
| 10 | 6-Me | 2-chlorophenyl | MF6 | 7-OMe | 6-Me | 3.3 | 13 | 13 | 5.5 | A10 | 203–205 (dec) |
| 11 | 6-Ph | 2-chlorophenyl | MI6 | 7-OMe | 6-Ph | 4.3 | 20 | 20 | 18 | A11 | 229–236 |

EXAMPLE 12

1-[1-(2-Chlorophenyl)cyclopropyl]-7-methoxy-2-methyl-1,2,3,4-tetrahydroisoquinoline (0.25 g, prepared as described in Example MF7) was heated on a steam bath at 100° C. in a solution of 48% hydrobromic acid (60 ml) and glacial acetic acid (60 ml) for 16 hours. The mixture was heated under reflux for 2 hours until the reaction was complete. The solvent was removed in vacuo and the residue dried by azeotropic distillation with propan-2-ol. The resulting suspension was removed by filtration and crystallised twice from ethanol to give 1-(1-(2-chlorophenyl)cyclopropyl)-7-hydroxy-2-methyl- 1,2,3,4-tetrahydroisoquinoline hydrobromide, which was characterised by elemental analysis.

EXAMPLES 13 to 34

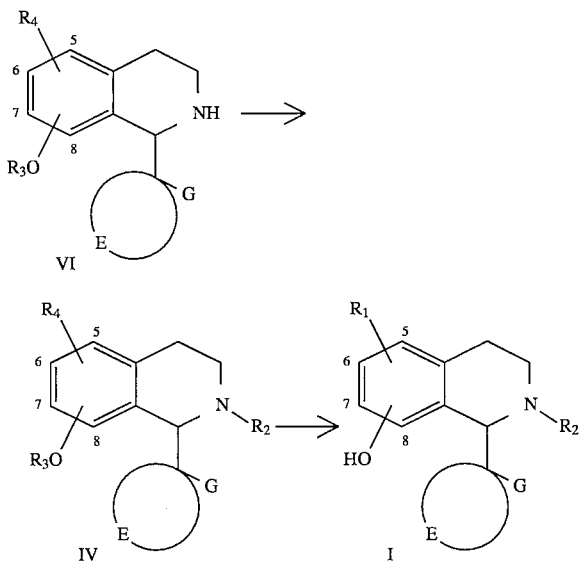

A mixture of a compound of formula VI in which $OR_3$, $R_4$, E and G are as defined in Table AA Part I (a g) anhydrous potassium carbonate (b g), methyl iodide (c g) and acetone (d ml) was stirred at ambient temperature for e hours. The reaction mixture was filtered and treated as set out in the Notes to Table AA part I to give a compound of formula IV in which $R_2$ is methyl, $OR_3$, $R_4$, E and G are as defined in Table AA Part I which was used without being characterised in the next stage of the reaction.

A mixture of a compound of formula IV prepared by the procedure in the above paragraph (f g), 48% hydrobromic acid (g ml) and glacial acetic acid (h ml) was heated under nitrogen under reflux for j hours to give a compound of formula I in which $R_1$ is as defined in Table AA Part II, $R_2$ is methyl, the position of the hydroxy substituent is indicated in the column headed POS in Table AA Part II and E and G are as defined in Table AA Part I. The desired product was isolated as described in the Notes to Table AA part II below.

NOTES TO TABLE AA

In column E of Table AA, W represents —$CH_2.CMe_2.CH_2$—

AA1 A further portion of methyl iodide (0.1 g) was added after 3 hours. The reaction mixture was filtered and the solvent removed by evaporation to give a residue which was dissolved in dichloromethane. The solution was filtered and the solvent removed by evaporation to give a solid residue which was used in the next stage.

AA2 The solvent was removed from the reaction mixture and the residue was dried by azeotropic distillation with propan-2-ol. The residue was then decolourised with charcoal in propan-2-ol to give the hydrobromide salt of the desired compound of formula I which was washed with propan-2-ol and then ether and dried in vacuo. The melting point of the salt is given in the last column of Table AA.

AA3 The desired product was obtained by filtering and removing the solvent from the reaction mixture.

AA4 The solvent was removed from the reaction mixture. The solution was decolourised with charcoal in methanol, filtered and the solvent removed to give a residue which was crystallised from propan-2-ol to give the hydrobromide salt, the melting point of which is given in the last column of Table AA.

AA5 The solvent was removed from the reaction mixture and the residue was partitioned between ether and water. The ether layer yielded the desired product.

AA6 The residue from the concentrated reaction mixture was partitioned between ether and saturated aqueous sodium bicarbonate solution. The ether layer yielded a residue which was treated with ethereal HCl to give the hydrochloride salt which was recrystallised from propan-2-ol. The melting point of this salt is given in Table AA.

AA7 The hydrobromide salt precipitated from the reaction mixture. The melting point of this salt is given in Table AA.

AA8 The residue from the reaction mixture was decolourised with charcoal in methanol, dried by azeotropic distillation with propan-2-ol and triturated with propan-2-ol and ether to give the hydrobromide salt. The melting point of the salt is given in Table AA.

AA9 The residue from evaporating the reaction mixture was decolourised with charcoal in propan-2-ol. The solvent was removed and the residue washed with ether and decolourised with charcoal in acetone. The solvent was removed to give the hydrobromide salt, the melting point of which could not be determined as the product decomposed at around 150° C.

AA10 The starting material was a compound of formula VI in which G was 4-methoxyphenyl. The methoxy group was converted into the desired hydroxy group during the second stage of the reaction. The residue from the reaction mixture was partitioned between water and dichloromethane. The organic layer yielded the desired product.

AA11 The residue from the concentrated reaction mixture was partitioned between ether and saturated aqueous sodium bicarbonate solution. The ether layer yielded a residue which was treated with ethereal HCl to give the hydrochloride salt which was recrystallised from a 10:1 mixture of ethanol and light petroleum ether (b.p. 60°–80° C.). The melting point of this salt is given in Table AA.

AA12 The residue from the evaporation of the solvent from the reaction mixture was decolourised with charcoal in propan-2-ol. The residue was washed with petroleum ether (b.p. 60°–80°) and partitioned between ethyl acetate and saturated aqueous sodium bicarbonate solution. The organic layer yielded an oil which was treated with ether to give a precipitate which was separated by filtration. The filtrate was treated with ethereal oxalic acid to give the oxalate salt of the desired product which was recrystallised from methanol. The melting point of this salt is given in Table AA.

AA13 The residue from evaporation of the solvent from the reaction mixture was treated with water, and extracted with ethyl acetate. The organic layer yielded the desired product which was used without further purification.

AA14 The residue from the evaporation of the solvent from the reaction mixture was decolourised with charcoal in methanol, dried by azeotropic distillation with propan-2-ol to give the hydrobromide salt which was recrystallised from propan-2-ol. The melting point of the salt is given in Table AA.

AA15 The residue from the evaporation of the solvent from the reaction solution was dried by azeotropic distillation with propan-2-ol, decolourised with charcoal in methanol and recrystallised from propan-2-ol to give the hydrobromide salt, the melting point of which is given in Table AA.

AA16 The residue from the evaporation of the solvent from the reaction mixture was partitioned between water and dichloromethane. The organic layer yielded the desired product.

AA17 The residue from evaporation of the solvent from the reaction mixture was partitioned between ethyl acetate and saturated aqueous sodium bicarbonate solution. The organic layer yielded a residue which was dissolved in a 10:1 mixture of ether and propan-2-ol and treated with ethereal HCl. The desired compound in the form of its hydrochloride salt precipitated on cooling and was recrystallised from a 10:1 mixture of propan-2-ol and methanol. The melting point of this salt is given in Table AA.

AA18 The residue from evaporation of the solvent from the reaction mixture was partitioned between ether and water. The organic layer was separated, decolourised with charcoal, evaporated to half volume and treated with ethereal HCl to give the desired product as a hydrochloride salt.

AA19 The residue from evaporation of the solvent from the reaction mixture was partitioned between ethyl acetate and saturated aqueous sodium bicarbonate solution. The organic phase was decolourised with charcoal and the solvent removed to give a residue which was treated with ethanolic HCl to give the desired product as a hydrochloride salt which was recrystallised from acetone. The melting point of this salt is given in Table AA.

AA20 The residue from evaporation of the solvent from the reaction mixture was partitioned between ether and water and the dried ether layer was treated with ethanolic HCl to give a gum which was treated with methanol to give the desired product as its hydrochloride salt which was used without further purification.

AA21 The residue from evaporation of the solvent from the reaction mixture was dried by azeotropic distillation with propan-2-ol, and decolourised with charcoal in methanol. The solvent was removed and the residue was treated with a mixture of propan-2-ol and ether to give a solid which was recrystallised from a 1:1 mixture of ethanol and ether to give the desired product as its hydrobromide salt, the melting point of which is given in the last column of Table AA.

AA22 The residue from evaporation of the solvent from the reaction mixture was dried by azeotropic distillation with propan-2-ol to give a residue which was crystallised from propan-2-ol to give the hydrobromide salt of the desired compound of formula I, the melting point of which is given in the last column of Table AA.

AA23 The starting material was liberated from its hydrochloride salt prior to the reaction. The solvent was removed from the reaction mixture and the residue was partitioned between ether and water. The ether layer yielded the desired product.

AA24 The residue from the reaction mixture was decolourised with charcoal in methanol and partitioned between ether and saturated aqueous sodium bicarbonate solution. The ether layer yielded a residue which was treated with ethereal HCl to give the hydrochloride salt. The melting point of this salt is given in Table AA.

AA25 The reaction mixture was cooled and poured into water. The mixture was extracted with ether. The desired product was obtained from the ether extract.

AA26 The reaction mixture was poured onto ice and basified with 5N aqueous sodium hydroxide solution and extracted with ether. The ether extract gave a residue which was dissolved in ether. Treatment with ethereal oxalic acid gave the oxalate salt of the desired product, the melting point of which is given in the last column of Table AA.

AA27 The solvent was removed from the reaction mixture and the residue partitioned between water and ether. The residue from evaporation of the extracts was treated with ethereal HCl and propan-2-ol. Removal of the solvents gave the hydrochloride salt of the desired product. The melting point of this salt is given in the last column of Table AA.

AA28 The residue from the reaction mixture was treated with saturated aqueous sodium bicarbonate colution and extracted with ethylacetate. The extracts gave a residue which was treated with a 1:10 mixture of propan-2-ol and ethereal HCl to give the hydrochloride salt of the desired product. The melting point of this salt is given in Table AA.

AA29 The solvent was removed from the reaction mixture and water added to the residue. The resulting mixture was extracted with ether. Ethereal oxalic acid was added to precipitate the oxalate salt of the product. The salt was dissolved in 1M aqueous sodium hydroxide solution and extracted with ether. The extract gave the desired product (as its free base) which was used without further purification.

AA30 The solvent was removed from the reaction mixture and the residue dried by azeotropic distillation with propan-2-ol, decolourised with charcoal in methanol and again dried by azeotropic distillation with propan-2-ol. The residue was dissolved in propan-2-ol and a solid precipitated by the addition of ether. This dissolution/precipitation cycle was repeated and the solid collected and washed with a 1:5 mixture of propan-2-ol and ether to give the desired product as its hydrobromide salt, the melting point of which is given in the last column of Table AA.

AA31 The residue from the reaction mixture was dried by azeotropic distillation with propan-2-ol to give a residue which was decolourised with charcoal in methanol, to give the hydrobromide salt. The melting point of the salt is given in Table AA.

TABLE AA

| | | | | | PART 1 | | | | | | |
|---|---|---|---|---|---|---|---|---|---|---|---|
| Ex | OR$_3$ | R$_4$ | E | G | SM | a | b | c | d | e | Note |
| 13 | 7-OMe | 6-OMe | (CH$_2$)$_2$ | 4-chlorophenyl | RB7 | 3.1 | 2.5 | 1.4 | 100 | 4 | AA1 |
| 14 | 7-OMe | 6-OMe | (CH$_2$)$_4$ | 4-chlorophenyl | RB17 | 4.9 | 3.3 | 2 | 50 | 1 | AA3 |
| 15 | 7-OMe | 6-OMe | (CH$_2$)$_4$ | phenyl | RB8 | 8.1 | 6.5 | 3.7 | 100 | 1 | AA5 |
| 16 | 7-OMe | 6-OMe | (CH$_2$)$_5$ | 4-chlorophenyl | RB9 | 9.1 | 6.5 | 3.7 | 200 | 0.75 | AA5 |
| 17 | 7-OMe | 6-OMe | (CH$_2$)$_3$ | 4-bromophenyl | RC5 | 5 | 3.4 | 1.9 | 75 | 4 | AA5 |
| 18 | 7-OMe | 6-OMe | (CH$_2$)$_3$ | 3,4-dichlorophenyl | RB13 | 3.5 | 2.5 | 1.4 | 50 | 2 | AA3 |
| 19 | 7-OMe | 6-OMe | (CH$_2$)$_4$ | 4-hydroxy- | RB12 | 7 | 5.3 | 3 | 50 | 0.5 | AA10 |

TABLE AA-continued

| Ex | POS | $R_1$ | | | Note |
|----|-----|-------|---|---|------|
| 20 | 7-OMe | 6-Br | $(CH_2)_3$ | phenyl phenyl | RB11 | 4.2 | 2.4 | 1.7 | 75 | 1.5 | AA5 |
| 21 | 7-OMe | 6-OMe | W | phenyl | RB10 | 10 | 7.9 | 4.2 | 100 | 1.5 | AA13 |
| 22 | 7-OMe | 6-Cl | $(CH_2)_3$ | 2-chlorophenyl | RC6 | 3.6 | 2.8 | 1.6 | 50 | 1.5 | AA13 |
| 23 | 7-OMe | 6-OMe | $(CH_2)_3$ | 2-trifluoromethylphenyl | RC7 | 5 | 3.5 | 2 | 100 | 2 | AA13 |
| 24 | 7-OMe | 6-F | $(CH_2)_3$ | 2-chlorophenyl | RC8 | 5 | 4 | 2.3 | 75 | 16 | AA13 |
| 25 | 7-OMe | 6-F | $(CH_2)_3$ | phenyl | RB14 | 8 | 7 | 4 | 100 | 1.5 | AA13 |
| 26 | 5-OMe | H | $(CH_2)_3$ | 4-chlorophenyl | RB15 | 4 | 3.4 | 1.9 | 75 | 3.5 | AA16 |
| 27 | 7-OMe | 6-OMe | $(CH_2)_2$ | phenyl | RB16 | 5 | 4.4 | 2.5 | 75 | 3 | AA18 |
| 28 | 7-OMe | 6-Cl | $(CH_2)_3$ | phenyl | RB18 | 5.6 | 4.9 | 2.8 | 50 | 1 | AA20 |
| 29 | 7-OMe | 6-OMe | $(CH_2)_5$ | phenyl | RB19 | 11 | 8.7 | 4.5 | 100 | 1.5 | AA13 |
| 30 | 7-OMe | 6-Cl | W | phenyl | RB21 | 2.1 | 1.6 | 0.9 | 30 | 1 | AA23 |
| 31 | 6-OMe | 7-Cl | $(CH_2)_3$ | phenyl | RB23 | 10.2 | 13.1 | 2.4 | 80 | 4 | AA25 |
| 32 | 7-OMe | 5-Cl 6-OMe | $(CH_2)_3$ | phenyl | RB24 | 7.1 | 5.4 | 3.1 | 100 | 0.5 | AA27 |
| 33 | 7-OMe | 6-OMe | $(CH_2)_3$ | 3-chlorophenyl | RC21 | 9.1 | 7.3 | 4.1 | 75 | 2 | AA29 |
| 34 | 7-OMe | 6-F | $(CH_2)_3$ | 2-bromophenyl | RC19 | 5.1 | 3.6 | 2.1 | 100 | 2.5 | AA13 |

PART II

| Ex | POS | $R_1$ | f | g | h | j | Note | mp |
|----|-----|-------|---|---|---|---|------|----|
| 13 | 7-OH | 6-OH | 2.25 | 30 | 0 | 5 | AA2 | 227–229 |
| 14 | 7-OH | 6-OH | 5 | 50 | 0 | 2 | AA4 | 228–232 |
| 15 | 7-OH | 6-OH | 5.9 | 50 | 0 | 1 | AA6 | 225–230 (dec) |
| 16 | 7-OH | 6-OH | 7.5 | 30 | 0 | 1.5 | AA7 | 231–233 (dec) |
| 17 | 7-OH | 6-OH | 4.0 | 20 | 20 | 6 | AA8 | 208–211 (dec) |
| 18 | 7-OH | 6-OH | 3.9 | 30 | 0 | 0.5 | AA9 | |
| 19 | 7-OH | 6-OH | 3 | 50 | 0 | 0.5 | AA11 | 194–196 (dec) |
| 20 | 7-OH | 6-Br | 3.6 | 20 | 20 | 3 | AA12 | 205 (dec) |
| 21 | 7-OH | 6-OH | 10 | 25 | 25 | 5 | AA4 | 200 (dec) |
| 22 | 7-OH | 6-Cl | 3.1 | 20 | 20 | 8 | AA14 | 215–218 |
| 23 | 7-OH | 7-OH | 4.4 | 20 | 20 | 6 | AA15 | 195 (dec) |
| 24 | 7-OH | 6-F | 3.9 | 25 | 25 | 2 | AA15 | 212–215 (dec) |
| 25 | 7-OH | 6-F | 6.5 | 25 | 25 | 4 | AA15 | 222–224 (dec) |
| 26 | 5-OH | H | 3.8 | 20 | 20 | 3.5 | AA17 | 165–167 |
| 27 | 7-OH | 6-OH | 2.5 | 30 | 0 | 1 | AA19 | 190–192 |
| 28 | 7-OH | 6-Cl | 5.6 | 25 | 22 | 24 | AA21 | 205–208 |
| 29 | 7-OH | 6-OH | 10.8 | 50 | 25 | 5 | AA22 | >200 (dec) |
| 30 | 7-OH | 6-Cl | 2.0 | 10 | 10 | 3 | AA24 | >240 (dec) |
| 31 | 6-OH | 7-Cl | 5.9 | 80 | 0 | 5 | AA26 | 105–109 (dec) |
| 32 | 7-OH | 5-Cl 6-OH | 7.1 | 30 | 30 | 5 | AA28 | 214–216 |
| 33 | 7-OH | 6-OH | 7.8 | 30 | 30 | 5 | AA30 | 225–230 |
| 34 | 7-OH | 6-F | 2.5 | 20 | 20 | 8 | AA31 | 248 (dec) |

EXAMPLES 35–39

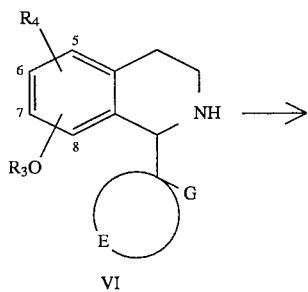

VI

-continued

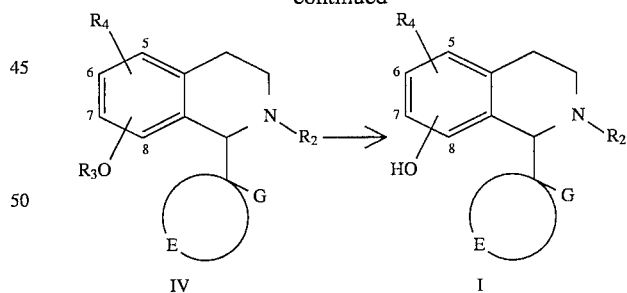

IV        I

A mixture of a compound of formula VI in which $OR_3$, $R_4$, E and G are as identified in Table AB Part I (a g), anhydrous potassium carbonate (b g), methyl iodide (c g) and acetone (d ml) was stirred at ambient temperature for e hours. The mixture was filtered and the solvent removed to give a residue which was partitioned between ether and water. The ether layer yielded a compound of formula IV in which $R_2$ is methyl and $OR_3$, $R_4$, E and G are as identified in Table AB Part I. This compound of formula IV was then heated under reflux with a solvent identified in column f of Table AB Part II (a= methanol, b=ethanol) (g ml) and concentrated hydrochloric acid (h ml) for j hours to give the desired compound of formula I in which the position of the hydroxy substituent is identified in the column headed "POS" in Table AB Part II, $R_1$ is as identified in Table AB Part II, $R_2$ is methyl and E and G are as identified in Table AB Part I. The procedure used to obtain the product is identified by the following notes to Table AB.

NOTES TO TABLE AB

The abbreviation "OBz" represents benzyloxy.

AB1 The solvent was removed from the reaction mixture and the residue partitioned between saturated aqueous sodium bicarbonate solution and ethyl acetate. The organic layer yielded a residue which was treated with ethereal oxalic acid to give the desired product as its oxalate salt, which was recrystallised from acetonitrile. The melting point of the salt is given in the last column of Table AB.

AB2 The solvent was removed from the reaction mixture and the residue basified with saturated aqueous sodium bicarbonate solution and extracted with ether. The extracts were treated with a 4:1 mixture of ethereal hydrogen chloride and propan-2-ol. Removal of the solvent gave a residue which was dried by azeotropic distillation with propan-2-ol. The residue was collected by filtration, washed with ether and dried in vacuo at 60° C. to give the desired product as its hydrochloride salt, the melting point of which is given in the last column of Table AB.

AB3 The solvent was removed from the reaction mixture. The residue was basified with saturated aqueous sodium bicarbonate solution and extracted with ethyl acetate. The extract yielded a residue which was dissolved in ether. Ethereal oxalic acid was added to give a solid which was boiled with a 9:1 mixture of ether and acetone to give the desired product as its oxalate salt, the melting point of which is given in the last column of Table AB.

AB4 The solvent was removed from the reaction mixture and the residue decolourised with charcoal in ethanol and dried by azeotropic distillation with propan-2-ol. The residue was triturated with ethyl acetate and dissolved in ethanol. The solvent was removed and the residue washed with petroleum ether (bp 60°–80° C.) and dried at 55° C. in vacuo to give the desired product as its hydrochloride salt, the melting point of which is given in the last column of Table AB.

AB5 Before heating the compound of formula IV under reflux, the compound was dissolved in a 1:1 mixture of ethyl acetate and petroleum ether (10 ml) and eluted through a flash chromatography column using the same solvent mixture as the eluant. Material having a retention factor (Rf) of 0.33 was collected and the solvent distilled off to give a solid which was dissolved in ethyl acetate and passed through a Florisil® column. Material having a retention factor (Rf) of 0.33 was collected and the solvent distilled off to yield a gum. This was dissolved in ether (60 ml), filtered and hydrogen chloride gas bubbled through the filtrate until precipitation ceased. The solid was collected by filtration, washed with ether and dried in vacuo at 50° C. for 4 hours (m.p. 173°–179° C.).

After heating the compound of formula IV under reflux, the solvent was removed from the reaction mixture and the residue dried by azeotropic distillation with propan-2-ol. The residue was triturated with a 1:3 mixture of propan-2-ol and ether and the solid collected by filtration, washed in a 1:3 mixture of propan-2-ol and ether and dried in vacuo at 50° C. for 4 hours to give the desired product as its hydrochloride salt, the melting point of which is given in the last column of Table AB.

TABLE AB

| | | | PART I | | | | | | | |
|---|---|---|---|---|---|---|---|---|---|---|
| Ex | $OR_3$ | $R_4$ | E | G | SM | a | b | c | d | e |
| 35 | 7-OBz | 6-OMe | $(CH_2)_3$ | 2-chlorophenyl | RB25 | 5 | 3.2 | 1.6 | 50 | 2 |
| 36 | 7-OBz | 6-OMe | $(CH_2)_5$ | phenyl | RB26 | 5.5 | 3.6 | 2 | 100 | 3 |
| 37 | 7-OBz | 6-OMe | $(CH_2)_3$ | 2,4-dichlorophenyl | RC13 | 3.8 | 2.2 | 1.3 | 75 | 1 |
| 38 | 7-OBz | 6-OMe | $(CH_2)_3$ | 2-methoxyphenyl | RC16 | 5.6 | 3.6 | 2 | 80 | 0.5 |
| 39 | 7-OBz | 6-OMe | $(CH_2)_3$ | 3-methoxyphenyl | RC17 | 5.4 | 4.35 | 2.15 | 70 | 3 |

| | | PART II | | | | | | |
|---|---|---|---|---|---|---|---|---|
| Ex | POS | $R_1$ | f | g | h | j | Notes | mp |
| 35 | 7-OH | 6-OMe | (a) | 25 | 25 | 3 | AB1 | 129–131 |
| 36 | 7-OH | 6-OMe | (b) | 30 | 30 | 3 | AB2 | 135–140 |
| 37 | 7-OH | 6-OMe | (a) | 20 | 20 | 2.5 | AB3 | 173–176 |
| 38 | 7-OH | 6-OMe | (a) | 25 | 25 | 5 | AB4 | 130–135 |
| 39 | 7-OH | 6-OMe | (b) | 25 | 25 | 6 | AB5 | 180–186 |

EXAMPLE 40

Formic acid (39ml) was added dropwise at 0° C. under nitrogen to a mixture of 1-[]-(2-bromophenyl)cyclobutyl]-6-chloro-7-methoxy-3,4-dihydroisoquinoline (5.5 g prepared as described in Example CA20), sodium borohydride (3.9 g) and tetrahydrofuran (50 ml). The reaction mixture was stirred at ambient temperature for 16 hours. A further portion of sodium borohydride (1 g) was added and the mixture heated at 50° C. for two hours. Water was added and the mixture basified by adding 50% aqueous sodium hydroxide. The mixture was extracted with ethyl acetate. The extract yielded a residue which was purified by flash chromatography. A mixture of the purified residue (0.7 g), glacial acetic acid (10 ml), 48% aqueous hydrobromic acid (10 ml) was heated under reflux for five hours. The solvent was then removed and the residue treated with propan-2-ol. Removal of the solvent gave 1-[1-(2-bromophenyl)cyclobutyl] -6-chloro-7-hydroxy-2-methyl-1,2,3,4-tetrahydroisoquinoline hydrobromide which was washed with ether and dried in vacuo, m.p. 165°–170° C. (dec).

EXAMPLE 41

Sodium borohydride (a total of 8 g) was added portionwise to a warm mixture of 7-methoxy-1-(1-phenyl-cyclobutyl)- 3,4-dihydroisoquinoline (15 g prepared as described in Example CT13) and industrial methylated spirits (200 ml) over a period of one hour. The mixture was added to water. The industrial methylated spirits were removed by evaporation and the residue extracted with ether. Removal of the solvent gave an oil which was dissolved in acetone (250 ml) and stirred with methyl iodide (7.57 g) and anhydrous potassium carbonate (13.4 g) for one hour at 50°–55° C. The reaction mixture was treated with charcoal and filtered. Removal of the solvent gave a residue which was digested with ether. The ether solution was filtered and the solvent removed to give an oil which was dissolved in glacial acetic acid (75 ml). 48% Hydrobromic acid (75 ml) was added and the mixture heated under reflux for 4 hours. The reaction mixture was added to a mixture of ice and aqueous ammonia solution. A semi-solid was deposited. The supernatant liquors were removed by decantation and the residue washed with water and dissolved in ethanol. Concentrated hydrochloric acid was added. The solvent was removed by evaporation to Give 7-hydroxy-2-methyl-1-( 1-phenylcyclobutyl)-1,2,3,4-tetrahydroisoquinoline hydrochloride (m.p. 236°–240° C.) which was crystallised from propan-2-ol.

EXAMPLE 42

A mixture of 6,7-dimethoxy-1-[1-(2-naphthyl)cyclobutyl] -1,2,3,4-tetrahydroisoquinoline (4.74 g prepared as described in Example RB20), 37–40% aqueous formaldehyde solution (5.1 ml), acetonitrile (120 ml) and sodium cyanoborohydride (1.3 g) was stirred at ambient temperature for 15 minutes. The mixture was neutralised by addition of glacial acetic acid and stirred for 45 minutes. The mixture was concentrated by evaporation and basified with 2N aqueous potassium hydroxide solution. The resulting mixture was extracted with ether. The extracts were washed with aqueous potassium hydroxide solution and extracted with aqueous hydrochloric acid. The acid extract was basified and extracted with ether. The ether extract yielded a residue, a portion (3.86 g) of which was mixed with 48% aqueous hydrobromic acid (40 ml) and glacial acetic acid (40 ml) and heated at 100° C. for two days. The solvent was removed by evaporation and the residue dried by azeotropic distillation with propan-2-ol. The residue was washed with ether and decolourised with charcoal in propan-2-ol. The mixture was filtered and yielded 6,7-dihydroxy-2-methyl-1-[1-(2-naphthyl)cyclobutyl]- 1,2,3,4-tetrahydroisoquinoline 1.1 hydrobromide (m.p. 150°–153° C.) which was dried in vacuo.

EXAMPLE 43

1M Sodium hydrogen phosphite [179 ml, prepared from phosphorous acid (14.7 g), water (180 ml) and sodium hydrogen carbonate (15 g)], then 37–40% aqueous formaldehyde solution (94 ml) was added to a stirred solution of 7-benzyloxy-6-methoxy-1-[1-(1-naphthyl)cyclopropyl]- 1,2,3,4-tetrahydroisoquinoline (9.3 g, prepared as described in Example RC15) in industrial methylated spirits (1 L). The mixture was stirred for 16 hours and the solvent removed in vacuo. Water (300 ml) was added to the residue, followed by excess aqueous ammonia solution. The product was extracted into ether. The extracts yielded a residue (9.1 g) which was extracted with a warm 5:4:1 mixture of petroleum ether (b.p. 40°–60° C.), ether and triethylamine. The solvents were removed from the extract by evaporation and the residue was purified by flash chromatography, using the above solvent mixture as eluant to give 7-benzyloxy-6-methoxy-2-methyl-1-[1-(1 -naphthyl)-cyclopropyl]-1,2,3,4-tetrahydroisoquinoline as a gum.

The gum was heated under reflux with ethanol (16 ml) and concentrated hydrochloric acid (16 ml) for 30 minutes, the solvent removed in vacuo and the residue digested with cold water to give 7-hydroxy-6-methoxy-2 -methyl-1-[1-(1-naphthyl)cyclopropyl]-1,2,3,4-tetrahydroisoquinoline hydrochloride (4.06 g), m.p. 196°–200° C.

EXAMPLE 44

A mixture of 5-chloro-8-methoxy-2-methyl-1-( 1-phenylcyclobutyl)-1,2,3,4-tetrahydroisoquinoline (5.5 g) prepared as described in Example MI5), 48% aqueous hydrobromic acid (50 ml) and glacial acetic acid (50 ml) was heated under reflux in a nitrogen atmosphere for 24 hours. The solvents were removed by evaporation The residue was decolourised with charcoal in methanol. The mixture was filtered and the solvent removed from the filtrate. The residue was dried by azeotropic distillation with propan-2-ol, and decolourised with charcoal in methanol. The mixture was filtered and the solvent removed from the filtrate. The residue was dried by azeotropic distillation with propan-2-ol and treated with ether to give 5-chloro-8-hydroxy-2 -methyl-1-(1-phenylcyclobutyl)-1,2,3,4-tetrahydroisoquinoline hydrobromide, m.p. 197°–200° C. (dec).

EXAMPLE 45

A solution of 1-phenylcyclobutanecarbonyl chloride (29 g) in ether (100 ml) was added to a mixture of 3,4-dimethoxyphenethylamine (28 g), triethylamine (25 ml) and ether (200 ml). The mixture was stirred for 1 hour. The reaction mixture was poured into water and the mixture extracted with ethyl acetate. The extract gave a solid (48.7 g) which was heated at 90°–95° C. for 64 hours with polyphosphate ester (200 g). The mixture was added to ice/water and the resulting mixture washed with ether, basified with excess aqueous ammonia solution and extracted with a 1:1 mixture of ether and toluene and then with ethyl acetate. Removal of the solvents from the extracts gave a solid. A sample of this solid (40 g) in methanol (500 ml) was treated portionwise with sodium borohydride (25 g in total). The mixture was heated under reflux for 16 hours and then acidified with 6N aqueous hydrochloric acid, basified with aqueous sodium hydroxide solution and extracted with ethyl acetate. The extract yielded a residue, a portion (15 g) of which was treated dropwise with formic acid (6.7 g) and then 37–40% aqueous formaldehyde solution (11 ml) was added. The mixture was heated under reflux for six hours and then cooled and basified with 5N aqueous sodium hydroxide solution. The resulting mixture was extracted with ether. The dried extract gave a residue which was dissolved in ether, filtered and treated with ethereal HCl. Evaporation yielded a residue which was recrystallised from industrial methylated spirits to give 6,7-dimethoxy-2-methyl-1-(1-phenylcyclobutyl)-1,2,3,4-tetrahydroisoquinoline hydrochloride, m.p. 130°–132° C.

The free base of the above product (9 g) was heated under reflux with 48% aqueous hydrobromic acid (200 ml) for 16 hours. On cooling a solid precipitated which was collected, washed with water and decolourised with charcoal in industrial methylated spirits and filtered. Partial evaporation of the filtrate caused crystallisation of 6,7-dihydroxy-2-methyl-1-(1-phenylcyclobutyl)- 1,2,3,4-tetrahydroisoquinoline hydrobromide, m.p. 95°–100° C.

EXAMPLE 46

A solution of methyl iodide (1.9 g) in acetone (20 ml) was added dropwise to a stirred suspension of 1-[1-(2,4-dichlorophenyl)cyclobutyl]-6,7-dimethoxy- 1,2,3,4-tetrahydroisoquinoline (4 g prepared as described in Example RC9) and anhydrous potassium carbonate (3.1 g) in acetone (70 ml). The mixture was stirred at ambient temperature for 90 minutes and the solvent removed by evaporation. Water was added and the mixture extracted with ether. The ether layer yielded 1-[1-(2,4-dichlorophenyl)cyclobutyl]-6,7-dimethoxy- 2-methyl-1,2,3,4-tetrahydroisoquinoline as an oil. A portion of this oil was characterised by conversion into its 1.5 oxalate salt, m.p. 125°–132° C.

A solution of the oil (3.2 g obtained by the procedure of the preceding paragraph) in dichloromethane (50 ml) was cooled to −50° C. under nitrogen. A 1M solution of boron tribromide in dichloromethane (24 ml) was added dropwise. The mixture was stirred at ambient temperature for 16 hours and cooled to −50° C. Methanol (20 ml) was added slowly. The solvents were removed by evaporation and the residue dried by azeotropic distillation with propan-2-ol. The residue was decolourised with charcoal in methanol and dissolved in propan-2-ol. Addition of ether caused precipitation of 1-[1-(2,4-dichlorophenyl)cyclobutyl-6,7-dihydroxy-2-methyl-1,2,3,4-tetrahydroisoquinoline hydrobromide, m.p. 205°–210° C.

EXAMPLE 47

A solution of methyl iodide (0.5 g) in acetone (10 ml) was added dropwise to a stirred suspension of 1-[1-(2-chlorophenyl)cyclobutyl]-7-methoxy-1,2,3,4-tetrahydroisoquinoline oxalate (1.4 g prepared as described in Example RC11) and anhydrous potassium carbonate (3 g) in acetone (80 ml). The mixture was stirred at ambient temperature for 3.5 hours and the solvent removed by evaporation. Water was added and the mixture extracted with ether. The ether layer yielded 1-[1-(2-chloro-phenyl)cyclobutyl]-7-methoxy-2-methyl-1,2,3,4-tetrahydroisoquinoline as an oil.

A solution of the oil (1.1 g obtained by the procedure of the preceding paragraph) in dichloromethane (50 ml) was cooled to −50° C. under nitrogen. A 1M solution of boron tribromide in dichloromethane (10 ml) was added dropwise. The mixture was stirred at ambient temperature for 16 hours and cooled to −50° C. Methanol (20 ml) was added slowly. The solvents were removed by evaporation and the residue dried by azeotropic distillation with propan-2-ol. The residue was decolourised with charcoal in methanol, dissolved in propan-2-ol and the solution warmed to 35°–40° C. Addition of ether gave a solid which was triturated with warm propan-2-ol. Ether was added to give 1-[1-(2-chlorophenyl)cyclobutyl] -7-hydroxy-2-methyl-1,2,3,4-tetrahydroisoquinoline hydrobromide, m.p. 216°–218° C.

EXAMPLE 48

A finely divided mixture of 4-hydroxy-3-methoxyphenethylamine (9.9 g) and 1-phenylcyclopentane carboxylic acid (11.9 g) was heated at 200° C. under nitrogen for two hours. The melt was cooled slightly and added to a 1:1 mixture of glacial acetic acid and water. A solid crystallised which was removed by filtration and washed with acetic acid. The filtrate was basified with excess sodium carbonate and extracted with ether. The extract was washed with 4N hydrochloric acid. The ether extract yielded a residue which was heated under reflux in a nitrogen atmosphere with acetonitrile (156 ml) and phosphorus oxychloride (18.7 ml) for one hour. The solvent was removed and water was added to the residue. The mixture was warmed and ethanol was added. The resulting solution was heated at 90°–95° C. for one hour and cooled. Ethanol was added to dissolve any solid and the solution basified with aqueous ammonia solution. Sodium borohydride (2.5 g in total) was added portionwise and the solvents removed by evaporation. The residue was partitioned between water and ethyl acetate to give a solid which was collected by filtration, washed with water and dried in air. The solid was dissolved in a mixture of 37–40% aqueous formaldehyde solution (27 ml) and formic acid (15 ml) and the solution warmed to 60° C. for two hours. Ice was added and the mixture basified with aqueous ammonia solution. The resulting mixture was extracted with ether. The extract was dried and the solvent removed to give a residue which was dissolved in ether. The extract was filtered, dried and ethereal oxalic acid was added. A solid was deposited. The ether was removed by decantation and ethyl acetate was added and the mixture heated at reflux. The solid product was triturated under the ethyl acetate, collected by filtration washed with ethyl acetate and dried in air to give 7-hydroxy-6-methoxy-2-methyl-1-(1-phenylcyclopentyl- 1,2,3,4-tetrahydroisoquinoline oxalate, m.p. 172° C. (dec).

EXAMPLE 49

A finely divided mixture of 4-hydroxy-3-methoxy phenethylamine (10.45 g) and 1-(4-chlorophenyl)cyclobutane carboxylic acid (12.17 g) was heated at 200° C. under nitrogen for two hours. The melt was cooled and added to a 1:1 mixture of glacial acetic acid and water. Addition of more water caused a precipitate to be deposited which was extracted with ether. The ether layer was washed with aqueous sodium carbonate solution and then 6N hydrochloric acid and yielded a residue which was heated under reflux in a nitrogen atmosphere with acetonitrile (227 ml) and phosphorus oxychloride (27.2 ml) for 16hours. Water (50 ml) and industrial methylated spirits were added and the mixture heated for 1 hour. After 16 hours excess aqueous ammonia solution and ice were added and the resulting solid was collected and washed with water and ether and dried at 60° C. in vacuo. The residue was digested with ethanol and the insoluble solid collected and dissolved in methanol (250 ml) and water (50 ml). Sodium borohydride (a total of 2.8 g) was added portionwise. The mixture was warmed for 30 minutes and then water and excess dilute hydrochloric acid were added. The supernatant liquor was basified with aqueous ammonia solution and the resultant precipitate extracted with ether. The ether was removed to leave a residue which was warmed with a mixture of 37–40% aqueous formaldehyde solution (45 ml) and formic acid (27 ml) for one hour. The mixture was allowed to stand for 16 hours and was then heated for a further 30 minutes and cooled. Ice and excess aqueous ammonia solution were added and the resulting mixture was extracted with ether. The solvent was removed and the residue dissolved in ether. Ethereal oxalic acid solution was added to the dried solution to give a semi-solid which was triturated with boiling ether and digested with ethyl acetate to give a gum which was digested with propan-2-ol to give 1-[1-(4-chlorophenyl)cyclobutyl] -7-hydroxy-6-methoxy-2-methyl-1,2,3,4-tetrahydroisoquinoline oxalate, m.p. 202° C. (dec).

EXAMPLE 50

A solution of 1-(4-chlorophenyl)cyclobutanecarbonyl chloride (22.9 g) in ether (200 ml) was added to a stirred mixture of 3,4-dimethoxyphenethylamine (18.1 g), triethylamine (13.9 ml) and ether (300 ml). The mixture was stirred for 1.5 hours and then water was added. The ether layer yielded a residue which was dissolved in dichloromethane (100 ml) and added to polyphosphate ester (195 g) under nitrogen. The mixture was kept at 75°–82° C. for 16 hours and then added to water (1,200 ml). The organic phase was washed with water and basified with excess aqueous ammonia solution. The basic aqueous solution was extracted with ether. The ether extract yielded an oil which was dissolved in methanol (200 ml). Twelve portions of sodium borohydride (12 g in total) were added over twenty minutes. The mixture was stirred for 16 hours and acidified by the careful addition of 5N hydrochloric acid. The mixture was allowed to stand for 16 hours and the resulting solid was separated by filtration. Water was added to the filtrate which was then basified and extracted with ethyl acetate. The extract gave a residue which was dried by azeotropic distillation with propan-2-ol to give 1-[1-(4-chlorophenyl)cyclobutyl]- 6,7-dimethoxy-1,2,3,4-tetrahydroisoquinoline, a sample (8.8 g) of which was heated at 90°–95° C. with formic acid (5 ml) and 37–40% aqueous formaldehyde solution (6.2 ml) for 16 hours. Water was added and the mixture basified with aqueous sodium hydroxide solution and extracted with ether. The extract yielded a gum which was heated under reflux with 48% aqueous hydrobromic acid (100 ml) for 3½ hours. Charcoal and industrial methylated spirits (100 ml) were added and the mixture filtered. Removal of the solvent from the filtrate gave a residue which was dried by azeotropic distillation with propan-2-ol. The residue was taken up in a 1:1 mixture of propan-2-ol and ethanol and the solvent removed by evaporation. The residue was heated under reflux with ethanol for 30 minutes and then cooled. The solid was collected by filtration and washed with a small amount of cold ethanol to give 1-[1-(4-chlorophenyl)cyclobutyl] -6,7-dihydroxy-2-methyl-1,2,3,4-tetrahydroisoquinoline hydrobromide, m.p. 220° C.

EXAMPLE 51

A solution of 1-(4-chlorophenyl)cyclobutane carbonyl chloride (30.7 g) in ether (300 ml) was added to a stirred solution of 4-methoxyphenethylamine (20.2 g) and triethylamine (20 ml) in ether (200 ml). After one hour, water (200 ml) was added and the ether layer removed by decantation. The aqueous layer was extracted with dichloromethane. The combined organic extracts gave a residue (46 g) which was mixed with polyphosphate ester (110 ml) and heated on a steam bath for 65 hours. The reaction mixture was added to a mixture of ice and concentrated aqueous ammonia solution and extracted with ether and ethyl acetate. The combined organic extracts gave a residue which was dissolved in ethanol (180 ml). Sodium borohydride (15.6 g in total) was added portionwise. The mixture was heated for one hour at 90°–95° C. Water and then dilute hydrochloric acid were added and the mixture basified with aqueous sodium hydroxide solution and extracted with ether. The extract was cooled, filtered and ethereal oxalic acid added to give a gum which was triturated with ether. The residue was basified with aqueous potassium hydroxide solution to give a residue which was purified by high performance liquid chromatography and a portion (1.6 g) of the product was heated under nitrogen for 19 hours with glacial acetic acid (35 ml) and 48% hydrobromic acid (35 ml). The mixture was cooled and added to a mixture of ice and 10% aqueous sodium carbonate solution. The insoluble material which was deposited was decolourised with charcoal in a mixture of 6N hydrochloric acid, acetic acid and methanol. The solution yielded a residue which was dried by azeotropic distillation with propan-2-ol.

A mixture of the residue (1 g), sodium formate (0.2 g), 37–40% aqueous formaldehyde solution (10 ml) and formic acid (10 ml) was heated at 90°–95° C. for 20 minutes. The mixture was allowed to stand for 16 hours and was poured onto a mixture of ice and aqueous ammonia solution which was extracted with ether. The extract yielded a residue which was purified by flash chromatography and converted into 1-[1-(4-chlorophenyl)cyclobutyl] -7-hydroxy-2-methyl-1,2,3,4-tetrahydroisoquinoline 1.35 oxalate, m.p. 192°–194° C. (dec).

EXAMPLE 52

1-Phenylcyclobutanecarbonyl chloride (20 g) in ether (100 ml) was added to a stirred mixture of 3-chloro-4-methoxyphenethylamine (19.1 g), triethylamine (14 ml) and ether (100 ml) and the resulting mixture stirred for one hour. Water was added and the mixture extracted with ethyl acetate. The extract yielded a solid (m.p. 62°–64° C.), a sample of which (14.6 g) was heated at 90° C. with polyphosphate ester (89 ml) for 48 hours. The mixture was poured into ice/water, basified with aqueous ammonia solution and extracted with ether. A portion (90% of the total) of the extract was added to a mixture of sodium borohydride (6 g) and ethanol (400 ml). The mixture was heated under reflux for 90 minutes after the ether had been allowed to escape and then the solvent was removed by evaporation to give a residue which was added to water. The resulting mixture was extracted with ether. The ether extract was added to a mixture of 1M aqueous sodium phosphite solution [prepared from phosphorous acid (20.5 g), sodium bicarbonate (21.0 g) and water (250 ml)], 37–40% aqueous formaldehyde solution (150 ml) and methanol (400 ml). The mixture was heated under reflux for 17 hours allowing the ether to evaporate. The methanol was then removed by evaporation and the residue basified with aqueous ammonia solution and extracted with ether. The extract yielded an oil which was purified by flash chromatography and then high performance liquid chromatography to give a compound (4.1 g) which was heated under reflux for five hours with glacial acetic acid (45 ml) and 48% hydrobromic acid (45 ml). The cooled reaction mixture was partitioned between ether and 50% aqueous potassium carbonate solution. The extract yielded a glass which was dissolved in ether and treated with ethereal oxalic acid to give 6-chloro-7 -hydroxy-2-methyl-1-(1-phenylcyclobutyl)-1,2,3,4-tetrahydroisoquinoline oxalate (m.p. 220°–223° C.).

EXAMPLE 53

A solution of 1-(4-chlorophenyl)cyclobutanecarbonyl chloride (20 g) in ether (50 ml) was added to a stirred mixture of 3-chloro-4-methoxyphenethylamine (16.2 g), triethylamine (13 ml) and ether (100 ml). After one hour, water (50 ml) was added and the mixture extracted with ethyl acetate. The organic layer gave a residue which was recrystallised twice from industrial methylated spirits. A portion of the product (12.6 g) was warmed with polyphosphate ester (70 ml). The resulting solution was heated at 90° C. for 48 hours, cooled and added to a mixture of ice, concentrated ammonia solution and ether. The ether layer was washed, dried and added to sodium borohydride (5 g) in ethanol (200 ml) and the mixture heated under reflux for 90 minutes. The ether evaporated during this time and then the ethanol was removed. Water (200 ml) was added and the resulting mixture extracted with ether. The extract was added to a mixture of 1M aqueous sodium phosphite solution [prepared from phosphorous acid (16.4 g), sodium bicarbonate (16.8 g) and water 200 ml)], 37–40% aqueous formaldehyde solution (130 ml) and methanol (300 ml). The ether was removed by evaporation and methanol (250 ml) added. The mixture was then heated under reflux for 16 hours and then the methanol was removed by evaporation. The residue was basified with aqueous ammonia solution and extracted with ether. The solvent was removed from the extract and the residue dried by azeotropic distillation with industrial methylated spirits and then with propan-2-ol. The dried residue was crystallised from propan-2-ol to give a solid which was further purified by high performance liquid chromatography. A sample of this purified product (1 g) was heated at 110°–115° C. under nitrogen with glacial acetic acid (10 ml) and 48% hydrobromic acid (10 ml) for 6 hours. The reaction mixture was then cooled and partitioned between ether and 50% aqueous potassium carbonate solution. The ether layer yielded 6-chloro-1-[1-(4-chlorophenyl)cyclobutyl]-7-hydroxy-2-methyl-1,2,3,4-tetrahydroisoquinoline (m.p. 168°–171° C.).

EXAMPLE 54

A solution of 1-(4-methoxyphenyl)cyclobutanecarbonyl chloride (5.83 g prepared as described in Example CL28) in dichloromethane (20 ml) was added to a solution of 3,4-dibenzyloxyphenethylamine hydrochloride (9.61 g) in dichloromethane (100 ml). Triethylamine (20 ml) was added. After 16 hours the mixture was acidified with dilute hydrochloric acid. The organic layer yielded a residue which was heated under reflux for 3 hours with phosphorus oxychloride (20 ml) and acetonitrile (200 ml). Removal of the solvent gave a residue which was digested with ethyl acetate. On cooling a solid dichlorophosphate salt precipitated. A sample (11.6 g) of this salt was added portionwise to a stirred mixture of sodium borohydride (9.5 g) in industrial methylated spirits (250 ml). The reaction mixture was heated for 3 hours at 90°–95° C. A mixture of sodium borohydride (3 g) and industrial methylated spirits (150 ml) was added and the resulting mixture gently boiled for two hours. The volume of the reaction mixture was reduced, water was added and the resulting mixture extracted with ether. The ether extract yielded a residue which was dissolved in a mixture of methanol (190 ml) and 37–40% aqueous formaldehyde solution (65 ml). The resulting solution was mixed with 1M aqueous sodium phosphite solution [prepared from phosphorous acid (9.9 g), sodium bicarbonate (10.1 g) and water (120 ml)] and methanol (300 ml) was added. The mixture was warmed and allowed to stand for 16 hours. The supernatant liquid was basified with aqueous ammonia solution and extracted with ether. The extract yielded a gum which was dissolved in a mixture of methanol (100 ml) and formic acid (20 ml) and stirred under nitrogen with 5% palladium on charcoal (4 g Type 38H ex Johnson Matthey) for 3 hours. The mixture was filtered and concentrated hydrochloric acid (1.2 ml) added to the filtrate. The solvent was removed by evaporation and the residue dried by azeotropic distillation with propan-2-ol, a mixture of propan-2-ol and toluene and then with propan-2-ol to give a solid which was triturated with ethyl acetate, collected by filtration, washed with ethyl acetate and dried in vacuo to give 6,7-dihydroxy-1-[1-(4-methoxyphenyl)cyclobutyl-2-methyl-1,2,3,4-tetrahydroisoquinoline hydrochloride, m.p. 85°–90° C.

EXAMPLE 55

Sodium borohydride (7 g in total) was added portionwise over 2.5 hours to a solution of the product of Example CT15(25 g) in industrial methylated spirits (300 ml) which was being heated under reflux. Water was added and the mixture extracted with ether. The extract yielded a solid which was mixed with a mixture of methanol (400 ml) and 37–40% aqueous formaldehyde solution (213 ml). A 1M solution of sodium phosphite [prepared from phosphorous acid (33.6 g) and sodium bicarbonate (34.4 g) and water (410 ml)] was added and the mixture heated at 90°–95° C. for 4 hours. The volume of the reaction mixture was reduced and the mixture basified with aqueous ammonia solution and extracted with ether. The extract yielded an oil which was dissolved in ethanol (270 ml) and heated under reflux in a nitrogen atmosphere for 30 minutes with concentrated hydrochloric acid (270 ml). The mixture was cooled and added to a mixture of ice and aqueous ammonia solution which was extracted with ether. The extract gave a residue which was purified by flash chromatography on silica using a 4:96 mixture of methanol and dichloromethane as eluant. The fraction containing the desired product was treated with ethereal oxalic acid solution to give a gum which was crystallised from a mixture of methanol and ethyl acetate to give -hydroxy-6-methoxy-2-methyl-1-(1-phenylcyclobutyl)- 1,2,3,4-tetrahydroisoquinoline 1.4 oxalate (m.p. 132°–133° C.).

EXAMPLE 56

A solution of 2'-bromo-4',5'-dimethoxyphenylacetonitrile (136.8 g) and 1,3-dibromopropane (58.7 ml) in dimethylsulphoxide (300 ml) was added dropwise over 2 hours to a stirred mixture of powdered potassium hydroxide hemihydrate (150 g) and 18-Crown-6(2 g) in dimethylsulphoxide (700 ml) under nitrogen at 24°–25° C. Stirring was continued for a further two hours and then a mixture of water and ice was added. The resulting mixture was extracted with dichloromethane. The extract gave a residue which was crystallised from ether. A sample of this crystallised material (67.2 g) was heated under reflux with a solution of potassium hydroxide hemihydrate (32.5 g) in propanol (600 ml) for 7 days. The solvent was removed and the residue partitioned between water and ethyl acetate. The ethyl acetate layer yielded 1-(2-bromo-4,5-dimethoxyphenyl)cyclobutane carboxamide which was heated under reflux with potassium hydroxide (30 g) and water (300 ml) for 3 days. The mixture was washed with ethyl acetate and the aqueous layer acidified and extracted with ether. The resulting acid was dissolved in ethyl acetate (80 ml) and the solution was mixed with a solution of 4-benzyloxy-3-methoxyphenethylamine (10.8 g) in ethyl acetate (320 ml). A salt precipitated which was heated under nitrogen at 195° C. for 2 hours and at 205° C. for 30 minutes. The reaction mixture was cooled and the resulting glass was heated under reflux with phosphorus oxychloride (22 ml) and acetonitrile (200 ml) for 4 hours. The reaction mixture was added to a mixture of ice and aqueous ammonia solution. The mixture was extracted with ether. The ether extract yielded a residue, a sample of which (5.9 g) was digested with ether. Addition of ethereal oxalic acid solution gave a solid which was basified with a methanolic solution of potassium hydroxide and partitioned between water and ether. The ether layer yielded a residue which was purified by flash chromatography to give a gum which was stirred with glacial acetic acid (20 ml) and methanol (10 ml) at 0° C. under nitrogen whilst sodium cyanoborohydride (0.8 g in total) was added portionwise. The mixture was then stirred at 20°–25° C. for 16 hours, added to aqueous potassium hydroxide solution and extracted with ether. The extract gave a residue (3.1 g) which was mixed with methanol (300 ml), 37–40% aqueous formaldehyde solution (26 ml) and 1M aqueous sodium phosphite solution [prepared from phosphorous acid (4.05 g), sodium bicarbonate (4.1 g) and water (50 ml)] and the mixture allowed to stand for 3 days. The solvent was removed by evaporation in vacuo at less then 50° C. and the residue added to a mixture of ice and aqueous ammonia solution and extracted with ether. The extract gave a residue which was dissolved in ethanol (35 ml) and was treated under nitrogen with concentrated hydrochloric acid (35 ml). The mixture was boiled for 30 minutes, cooled, added to a mixture of ice and aqueous ammonia solution and extracted with ethyl acetate. The extract gave a residue which was purified by flash chromatography to give 1-[1-(2-bromo-4, 5-dimethoxyphenyl)cyclobutyl] -7-hydroxy-6-methoxy-2-methyl- 1,2,3,4-tetrahydroisoquinoline, m.p. 154°–157° C.

EXAMPLE 57

The product of Example 41 (4 g) was dissolved in water at 80° C. The solution was basified with aqueous ammonia solution and extracted with ethyl acetate. The extract gave a residue which was dissolved in acetic acid (40 ml). The solution was cooled to 0° C. and acetic anhydride (20 ml) and then a mixture of 70% nitric acid (1.4 ml), acetic acid (30 ml) and acetic anhydride (20 ml) were added. The mixture was kept at 5° C. for 40 minutes and was then added to aqueous sodium bicarbonate and left for 16 hours before being extracted with ethyl acetate. The extract gave a residue which was purified by flash chromatography to give a solid which was dissolved in ethyl acetate. Addition of ethereal oxalic acid solution gave a solid which was triturated with hot ethyl acetate to give 7-hydroxy-2-methyl-6-nitro-1 -(1-phenylcyclobutyl)-1,2,3,4-tetrahydroisoquinoline oxalate, m.p. 172°–173° C. (dec).

EXAMPLE 58

Sodium hypochlorite solution (11 ml—8% available chlorine) was added at 0° C. to a mixture of the product of Example 41 in the form of its free base (2 g), glacial acetic acid (25 ml), water (20 ml) and concentrated hydrochloric acid (20 ml). Glacial acetic acid (25 ml) and concentrated hydrochloric acid (20 ml) were added followed by a further amount (8 ml) of the above sodium hypochlorite solution. The mixture was stirred for 20 minutes and excess solid sodium metabisulphite added. The mixture was basified with aqueous sodium hydroxide solution and extracted with ether. The extract gave a residue which was dissolved in ether. Addition of ethereal oxalic acid solution gave 6,8-dichloro-7-hydroxy-2-methyl-1-(1-phenylcyclobutyl)- 1,2,3,4-tetrahydroisoquinoline 1.5 oxalate, m.p. 120° C. (dec) .

EXAMPLE 59

A solution of 1-phenylcyclobutanecarbonyl chloride (19.45 g) in dichloromethane (100 ml) was added at 10°–13° C. to a solution of 3-chloro-4-methoxyphenethylamine (18.55 g) and triethylamine (30 ml) in dichloromethane (300 ml) over 20minutes. The mixture was stirred at 20°–25° C. for 3hours and stood for 3 days. Water was added and the organic layer separated and washed with 2N hydrochloric acid and then with 1N aqueous sodium hydroxide solution. The organic layer gave a gum (32.89 g) which was heated under reflux with xylene (390 ml) and phosphorus oxychloride (76.8 ml) for ten hours. The reaction mixture was added portionwise to a stirred mixture of aqueous potassium hydroxide solution and ice. The temperature was maintained below 85° C. Toluene at around 80° C. was added to dissolve deposited oil. The organic layer was separated and yielded an oil which was crystallised from propan-2-ol. The crystallised solid (10 g) was dissolved in ethanol (200 ml) and sodium borohydride (2 g) added with warming. After 40 minutes the solvent was removed and the residue treated with water and extracted with ether to give a residue which was heated under reflux with sodium borohydride (a total of 8 g) and propan-2-ol (100 ml) for a total of 7 hours. The mixture was cooled and water, then dilute hydrochloric acid and then aqueous sodium hydroxide solution were added. The mixture was extracted with ether. The ether extract gave 6-chloro-7-methoxy-1-(1-phenylcyclobutyl)-1,2,3,4-tetrahydroisoquinoline a portion of which (8.78 g) was dissolved in methanol (100 ml) and treated with a solution of dibenzoyl-L-tartaric acid (10.08 g) in methanol (50 ml). Solvent was removed at 40° C./40 mm Hg to leave 70 ml. Ether was added until a slight precipitate was seen and the mixture warmed to give a clear solution. On cooling a solid precipitated which was separated by filtration. The filtrate was basified with aqueous sodium hydroxide solution and extracted with ether. The extract gave an oil which was treated in methanol with dibenzoyl-D-tartaric acid (7.12 g) and a solid precipitated by the addition of ether. A sample of the latter solid (2.9 g) and sodium bicarbonate (0.35 g) in methanol (50 ml) was stirred and 1M sodium phosphite solution [prepared from phosphorous acid (2.55 g), sodium bicarbonate (2.61 g) and water (31 ml)] and 37–40% aqueous formaldehyde solution (16 ml) was added. Methanol (50 ml) was added and the mixture left for 16 hours, basified with aqueous ammonia solution and extracted with ether. The extract gave a residue which was dissolved in glacial acetic acid (20 ml) and 48% hydrobromic acid (20 ml) was added under nitrogen. The mixture was heated at 100° C. for 16 hours and then under reflux for 6.5 hours, cooled, added to a mixture of ice and aqueous ammonia solution and extracted with ethyl acetate. The extract gave a residue which was purified by flash chromatography to give (−)-6-chloro-7-hydroxy- 2-methyl-1-(1-phenylcyclobutyl)-1,2,3, 4-tetrahydroisoquinoline (m.p. 73°–75° C.) which had a specific optical rotation $\alpha_D$ of −139.8°.

EXAMPLE 60

1-[1-(2-Bromophenyl)cyclobutyl]-6,7-dimethoxy- 1,2,3, 4-tetrahydroquinoline (15.7 g, prepared in a similar manner to that described in Example RB1) was dissolved in ether (1100 ml) and treated with a 0.4M solution of dibenzoyl-L-tartaric acid in ether (98 ml). A solid precipitated which was collected by filtration and dried in vacuo. A portion of this solid (10.5 g)was dissolved in boiling methanol (350 ml). The solution was allowed to stand for 2days and (−)-1-[1-(2-bromophenyl)cyclobutyl] -6,7-dimethoxy-1,2,3,4-tetrahydroisoquinoline dibenzoyl-L-tartrate, was collected by filtration and recrystallised from methanol. Further samples of this salt were obtained from the mother liquors from which the solid had precipitated by removing the solvent by evaporation and recrystallising the residue from methanol. The salt (m.p. 174°–175° C. (dec)) had a specific optical rotation $\alpha_D$ of −57.6° to −61.9°.

A mixture of (−)-1-[1-(2-bromophenyl)cyclobutyl]- 6,7-dimethoxy-1,2,3,4-tetrahydroisoquinoline (1.85 g) [liberated from the dibenzoyl-(L)-tartrate salt (3.7 g)], acetonitrile (60 ml), 37–40% aqueous formaldehyde solution (1.8 ml) and sodium cyanoborohydride (0.46 g) was stirred for 15 minutes, then neutralised with glacial acetic acid and stirred for a further 45 minutes. The mixture was concentrated by evaporation and basified to pH 12 with dilute aqueous sodium hydroxide solution. The mixture was extracted with ethyl acetate, the extract yielding a gum which was purified via flash chromatography using a 1:2 mixture of ethyl acetate and petroleum ether as eluant to give (−)- 1-[1-(2-bromophenyl)cyclobutyl]-6,7-dimethoxy-2-methyl- 1,2,3,4-tetrahydroisoquinoline, which had a specific optical rotation $\alpha_D$ of −33.6°. Yield 1.6 g.

A mixture of (−)-1-[1-(2-bromophenyl)cyclobutyl]- 6,7-dimethoxy-2-methyl-1,2,3,4-tetrahydroisoquinoline (1.46 g), 48% aqueous hydrobromic acid (20 ml) and glacial acetic acid (20 ml) was heated under reflux for 5 hours. The solvent was removed by evaporation and the residue dried by repeated azeotropic distillation with propan-2-ol. The residue was dissolved in propan-2-ol and precipitated with ether. The resulting solid was dried in vacuo at 45° C. to yield (+)-1-[1-(2-bromo-phenyl)cyclobutyl] -6,7-dihydroxy-2-methyl-1,2,3,4-tetrahydroisoquinoline hydrobromide [m.p. 207°–209° C. (dec)] which had a specific optical rotation $\alpha_D$ of +38.2°.

EXAMPLE 61

A solution of 1-(2-chlorophenyl)cyclopropane carbonyl chloride (25 g) in dichloromethane (100 ml) was added dropwise to a vigorously stirred mixture of 2-(3 -fluoro-4-methoxyphenyl)ethylamine hydrochloride (23.9 g), triethylamine (70 ml) and dichloromethane (400 ml) and the mixture was then stirred for 1 hour. Excess 6N hydrochloric acid was then added. The resulting solution was washed with water, dried over potassium carbonate, and the solvent removed in vacuo to give N-[2-(3-fluoro-4-methoxyphenyl)ethyl]-1-(2-chlorophenyl)cyclopropane carboxamide which was added molten to polyphosphate ester (365 g) under nitrogen. The mixture was heated at 100° C. for 17 hours, then added to water (600 ml) and washed with ether (600 ml). 20% Aqueous ammonia solution was added to the aqueous phase to give pH 8–9.The resulting precipitate was collected by filtration, washed with water, dried in air and recrystallised from boiling acetonitrile to give 1-[1-( 2-chlorophenyl)cyclopropyl]-6-fluoro-7-methoxy-3,4-dihydroisoquinoline, m.p. 172°–176° C.

Sodium cyanoborohydride (10.7 g) was added at 0° C. to a mixture of 1-[1-(2-chlorophenyl)cyclopropyl]-6-fluoro-7-methoxy-3,4-dihydroisoquinoline (26.7 g, prepared in a similar manner to that described above), acetic acid (185 ml) and methanol (95 ml) under nitrogen. The mixture was allowed to reach ambient temperature and was stirred for 22 hours. The mixture was poured onto water, and solid sodium hydroxide (150 g) in ice-water (500 ml) was added. The product was extracted into ether and the solvent then removed in vacuo to yield 1-[ 1-(2-chlorophenyl)cyclopropyl]-6-fluoro-7-methoxy- 1,2,3,4-tetrahydroisoquinoline as a gum.

A mixture of the gum, methanol (2700 ml), 1M sodium hydrogen phosphite [690 ml, prepared from phosphorous acid (56.6 g) and sodium hydrogen carbonate (57.9 g)] and 37–40% aqueous formaldehyde solution (360 ml) was warmed to 60° C. and then stirred at ambient temperature for 64 hours. The methanol was removed in vacuo, and a solution of potassium hydroxide (50 g) in water (500 ml) and then ethyl acetate (500 ml) were added to the resulting aqueous suspension. The organic layer was dried over potassium carbonate and the solvent removed in vacuo to give a gum which was crystallised from acetonitrile to give 1-[1-(2-chlorophenyl)cyclopropyl]- 6-fluoro-7-methoxy-2-methyl-1,2,3,4-tetrahydroisoquinoline. Yield 18.15 g.

A mixture of 1-[1-(2-chlorophenyl)cyclopropyl]-6 -fluoro-7-methoxy-2-methyl-1,2,3,4-tetrahydroisoquinoline (18.0 g) in acetic acid (150 ml) and 48% aqueous hydrobromic acid (150 ml) was heated under reflux under argon for 220 minutes. The solvent was removed in vacuo, and the residue dried by azeotropic distillation with propan-2-ol and crystallised from propan-2-ol to yield 1-[1-(2-chlorophenyl)cyclopropyl]-6-fluoro-7 -hydroxy-2-methyl-1,2,3,4-tetrahydroisoquinoline hydrobromide (18.56 g), m.p. 240° C. (dec).

EXAMPLE 62

1-[1-(2-Chlorophenyl)cyclopropyl]-6-fluoro-7 -hydroxy-2-methyl-1,2,3,4-tetrahydroisoquinoline hydrobromide (18 g, prepared in a similar manner to that described in Example 61) was partitioned between aqueous ammonia solution and ethyl acetate. The ethyl acetate was removed in vacuo and the residue separated into two fractions by chiral preparative high performance liquid chromatography on a Chiralcel OD column eluted with a 97:3 mixture of hexane and ethanol. Fraction 1 was dissolved in propan-2-ol and treated with a slight excess of 48% aqueous hydrobromic acid. The resulting solid was collected by filtration and dried to give (+)-1-[1-(2-chlorophenyl)cyclopropyl]-6-fluoro-7-hydroxy-2 -methyl-1,2,3,4-tetrahydroisoquinoline hydrobromide which had a specific optical rotation $\alpha_D$ of +2.38°. Yield 7.88 g, m.p. 250° C. (dec).

EXAMPLE 63

A solution of 1-[1-(2-chlorophenyl)cyclopropyl]-6 -fluoro-7-hydroxy-2-methyl-1,2,3,4-tetrahydroisoquinoline hydrobromide (1 g, prepared in a similar manner to that described in Example 61) in ethyl acetate (30 ml) was mixed with a solution of maleic acid (0.24 g) in ethyl acetate (8 ml) and the mixture warmed to form a solution. The solution was cooled to yield 1-[1-(2-chlorophenyl)cyclopropyl] -6-fluoro-7-hydroxy-2-methyl- 1,2,3,4-tetrahydroisoquinoline maleate, m.p. 183°–184° C. Yield 0.9 g.

EXAMPLE 64

1-[1-(2-Chlorophenyl)cyclobutyl]-6-fluoro-7-hydroxy-2methyl- 1,2,3,4-tetrahydroisoquinoline (8.0 g liberated from the salt prepared as described in Example 24) was resolved by chiral preparative high performance liquid chromatography on a Chiralcel OD column eluted with an 80:20 mixture of hexane and ethanol. The residue formed by the removal of the solvent from fraction 1 was dissolved in propan-2-ol and treated with 48% aqueous hydrobromic acid to yield (+)-1-[1-(2-chlorophenyl)cyclobutyl] -6-fluoro-7- hydroxy-2-methyl-1,2,3,4 -tetrahydroisoquinoline hydrobromide which had a specific optical rotation $\alpha_D$ of +9.64°, m.p. 242°–245° C. (dec). Yield 3.63 g.

EXAMPLE 65

6-Chloro-7-methoxy-1-(1-phenylcyclobutyl)- 1,2,3,4-tetrahydroisoquinoline (1.38 g prepared in a similar manner to that described in Example 59) which was dissolved in acetone (50 ml) and stirred with anhydrous potassium carbonate (1.16 g) and allyl iodide (0.78 g) for one hour. The mixture was filtered and the filtrate concentrated and partitioned between water and ether. The ether layer yielded an oil which was taken up in dichloromethane (30 ml) and cooled to −70° C. A 1M solution of boron tribromide in dichloromethane (11 ml) was added dropwise and the mixture allowed to warm to ambient temperature. After two hours the mixture was cooled to −60° C. and methanol (30 ml) was added cautiously. The solvents were removed and the residue decolourised with charcoal in methanol. Removal of the solvent gave a residue which was recrystallised from a mixture of propan-2-ol and ether to give 2-allyl-6 -chloro-7-hydroxy-1-(1-phenylcyclobutyl)-1,2,3,4-tetrahydroisoquinoline hydrobromide, m.p. 194°–196° C.

EXAMPLE 66

A mixture of 1-[1-(4-chlorophenyl)cyclobutyl]- 6,7-dimethoxy-1,2,3,4-tetrahydroisoquinoline (7.29 g prepared as described in Example 50), ethyl iodide (1.76 ml), anhydrous potassium carbonate (5.52 g) and acetone (100 ml) was heated under reflux for 16 hours. The reaction mixture was filtered and the solvent was removed by evaporation to give a residue which was digested with a 9:1 mixture of petroleum ether and triethylamine. The solution was filtered and the solvent removed to give a residue. A sample of this residue (4 g) was heated under reflux in a nitrogen atmosphere with glacial acetic acid (40 ml) and 48% hydrobromic acid (40 ml) for 20 hours. Removal of the solvent gave a residue which was dried by azeotropic distillation with industrial methylated spirit, then with propan-2-ol and finally with a mixture of toluene and propan-2-ol to give a solid which was washed with propan-2-ol and dried in vacuo at 80° C. to give 1-[1-(4-chlorophenyl)cyclobutyl] -2-ethyl-6,7-dihydroxy-1,2,3,4-tetrahydroisoquinoline hydrobromide, m.p. 213°–215° C.

EXAMPLE 67

A mixture of 1-[1-(4-chlorophenyl)cyclobutyl]- 6,7-dimethoxy-1,2,3,4-tetrahydroisoquinoline (7.29 g prepared as described in Example 50), allyl bromide (2.66 g), anhydrous potassium carbonate (5.52 g) and acetone (100 ml) was heated under reflux for 2 hours. The reaction mixture was filtered and the solvent was removed by evaporation to give a residue which was digested with a 9:1 mixture of petroleum ether and triethylamine. The solution was decanted from a residual tar, filtered and the solvent removed to give a residue. A sample of this residue (3 g) was heated under reflux in a nitrogen atmosphere with glacial acetic acid (50 ml) and 48% hydrobromic acid (50 ml) for 7 hours. The reaction mixture was added to ice/water and excess aqueous ammonia solution added slowly under nitrogen. The resulting mixture was extracted with ethyl acetate. The organic layer was evaporated and the residue dissolved in ethyl acetate. Addition of a solution of oxalic acid in ethyl acetate gave 2-allyl-1-[1-(4-chlorophenyl)cyclobutyl]-6,7-dihydroxy- 1,2,3,4-tetrahydroisoquinoline oxalate [m.p. 85° C. (dec)] which was dried in air.

EXAMPLE 68

1-(2-Bromophenyl)cyclobutanecarbonyl chloride (9.4 g) was added to a solution of 4-benzyloxy-3-methoxy phenethylamine (8 g) and triethylamine (3.15 g) in ethyl acetate (50 ml) and tetrahydrofuran (50 ml). The mixture was stirred for two days, 2M aqueous potassium hydroxide solution (50 ml) added and the mixture stirred for 20 minutes. The aqueous layer was separated and extracted with ethyl acetate. The extract was washed with 1M hydrochloric acid and brine and yielded an oil which was dissolved in acetonitrile (180 ml). Phosphorus oxychloride (12 ml) was added and the mixture heated under reflux for 2.5 hours. The mixture was cooled and added to a mixture of concentrated aqueous ammonia solution (100 ml) and water (100 ml) and the mixture stirred for 10 minutes and extracted with ethyl acetate. The extract yielded an oil which was triturated with ether and the resulting solid recrystallised from cyclohexane to give 7-benzyloxy-1-[1-(2-bromophenyl)cyclobutyl] -6-methoxy-3,4,-dihydroisoquinoline (m.p. 115°–116° C.). A sample (3.1 g) of this material in methanol (16 ml) and acetic acid (35 ml) was treated with sodium cyanoborohydride (1 g). The mixture was stirred for 16 hours, diluted with water, basified with 50% aqueous sodium hydroxide solution and extracted with ether. The extract gave a residue which was dissolved in acetonitrile (115 ml) and then 37–40% aqueous formaldehyde solution (3.2 ml) and sodium cyanoborohydride (0.83 g) were added. The mixture was stirred for 15 minutes and then neutralised with acetic acid and stirred for 45 minutes. After concentration, 2M aqueous sodium hydroxide solution was added and the mixture extracted with ethyl acetate. The extract gave 7-benzyloxy-1-[1-(2-bromophenyl)cyclobutyl]-6-methoxy-2-methyl-1,2,3,4-tetrahydroisoquinoline, a sample of which (3 g) was mixed with ethanol (70 ml) and concentrated hydrochloric acid (70 ml) and the mixture heated under reflux for 45 minutes. The solvent was removed by evaporation and the residue dried by azeotropic distillation with propan-2-ol. The dried residue was suspended in propan-2-ol (20 ml) and the mixture filtered. The filtrate was decolourised with charcoal in methanol. The free base was liberated by basification and dissolved in ether. Removal of the ether gave 1-[1-(2-bromophenyl)cyclobutyl]-7-hydroxy-6-methoxy-2-methyl-1,2,3,4-tetrahydroisoquinoline (m.p. 48°–51° C.) which was dried in vacuo (ca 0.1 mmHg) for four hours.

EXAMPLE 69

A mixture of the hydrochloride salt of 7-benzyloxy-1-[1-(2-chlorophenyl)cyclobutyl]-6-methoxy-1,2,3,4-tetrahydroisoquinoline (2.75 g prepared in a similar manner to that described in Example RB25), methanol (50 ml) and 37–40% aqueous formaldehyde solution (3 ml) was cooled to 10° C. and sodium cyanoborohydride (1.52 g) was added. The mixture was stirred for 24 hours and the solvents removed by evaporation. The residue was partitioned between ethyl acetate and dilute aqueous sodium hydroxide solution. The organic layer yielded a gum which was dissolved in methanol (25 ml) and concentrated hydrochloric acid (25 ml) and heated under reflux for 1 hour. The solvents were removed by evaporation and the residue partitioned between ether and saturated aqueous sodium bicarbonate solution. The ether layer yielded a residue which was dissolved in propan-2-ol (100 ml) and 48% aqueous hydrobromic acid (5 ml). The solvent was removed by evaporation and the residue crystallised and then recrystallised from propan-2-ol to give 1-[1-(2-chlorophenyl)cyclobutyl]- 7-hydroxy-6-methoxy-2-methyl-1,2,3,4-tetrahydroisoquinoline hydrobromide, m.p. 148°–150° C.

EXAMPLE 70

A mixture of 7-benzyloxy-6-methoxy-[1-(2-chlorophenyl)- 3,3-dimethylcyclobutyl]-1,2,3,4-tetrahydroisoquinoline (6.1 g, prepared as described in Example RC23), methanol (50 ml) and concentrated hydrochloric acid (50 ml) was heated under reflux for 20 hours. The mixture was cooled and the volume reduced by 25%. 7 -Hydroxy-6-methoxy-[1-(2-chlorophenyl)-3,3-dimethylcyclobutyl] -1,2, 3,4-tetrahydroisoquinoline [m.p. 163°– 165° C. (dec)] crystallised and was collected by filtration.

A mixture of 7-hydroxy-6-methoxy-[1-(2-chlorophenyl)- 3,3-dimethylcyclobutyl]-1,2,3,4-tetrahydroisoquinoline (3.7 g), methanol (50 ml) and 37–40% aqueous formaldehyde solution was cooled to 5° C. Sodium cyanoborohydride (1.4 g) was added and the mixture stirred for 1.5 hours. The solvents were removed by evaporation and the residue partitioned between water and dichloromethane. The organic layer was washed with aqueous ammonia solution and then brine, dried and the solvent removed by evaporation to give a gum which was dissolved in propan-2-ol. Addition of 48% aqueous hydrobromic acid gave 7-hydroxy-6-methoxy-2-methyl-1-[1-( 2-chlorophenyl)-3,3-dimethylcyclobutyl]-1,2,3,4-tetrahydroisoquinoline hydrobromide, m.p. 202°–204° C. (dec).

EXAMPLE 71

Sodium cyanoborohydride (0.8 g) was added to a mixture of 7-benzyloxy-6-methoxy-1-[1-(2-methylthiophenyl)cyclobutyl] -3,4-dihydroisoquinoline (2.8 g, prepared as described in Example CA32), acetic acid (20 ml) and methanol (10 ml) at 0° C. and stirred for 60 hours at ambient temperature. The mixture was poured onto water (300 ml) and extracted with dichloromethane. The organic layer was washed with aqueous ammonia solution (100 ml), then brine (100 ml), and dried over magnesium sulphate. The solvent was removed by evaporation to yield a gum. The gum was dissolved in propan-2-ol and treated with excess 48% aqueous hydrobromic acid. Evaporation of the solvent yielded a solid which was triturated with petroleum ether (b.p. 60°–80° C.), then isolated by filtration to give 7 -benzyloxy-6-methoxy-1-[1-(2-methylthiophenyl)cyclobutyl]- 1,2,3,4-tetrahydroisoquinoline.

A mixture of 7-benzyloxy-6-methoxy-1-[1-(2-methylthiophenyl)cyclobutyl] -1,2,3,4-tetrahydroisoquinoline. (1.89 g), 37% aqueous formaldehyde solution (3 ml), methanol (30 ml) and sodium cyanoborohydride (0.5 g) was stirred at ambient temperature for 24 hours. The mixture was poured onto water (100 ml) and extracted with dichloromethane (300 ml). The extract was washed with dilute aqueous ammonia solution to yield a residue which was dissolved in propan-2-ol and treated with 48% aqueous hydrobromic acid. The solvent was removed by evaporation to yield 7-benzyloxy-6-methoxy-2-methyl-1-[1-(2-methylthiophenyl)cyclobutyl] -1,2,3,4-tetrahydroisoquinoline which was used without further purification.

7-Benzyloxy-6-methoxy-2-methyl-1-[1-(2-methylthiophenyl) cyclobutyl]-1,2,3,4-tetrahydroisoquinoline (1.7 g) was heated under reflux for 2 hours with 48% aqueous hydrobromic acid (15 ml) and glacial acetic acid (15 ml). The solvents were removed by evaporation in vacuo and the residue dried by azeotropic distillation with propan-2-ol. The residue was then dissolved in propan-2-ol, decolourised with charcoal and the solvent evaporated to yield 6,7-dihydroxy-2-methyl-1-[1-(2-methylthiophenyl )cyclobutyl] -1,2,3,4-tetrahydroisoquinoline hydrobromide (1.1 g).

EXAMPLE 72

A mixture of 7-benzyloxy-6-methoxy-1-[1-(4-trifluoromethoxyphenyl)cyclobutyl] -1,2,3,4-tetrahydroisoquinoline (4.1 g, prepared in a similar manner to that described in Example RC18), 37–40% aqueous formaldehyde solution (4.4 ml), acetonitrile (90 ml) and sodium cyanoborohydride (2.32 g) was stirred at 5° C. for 15 minutes, then neutralised with glacial acetic acid and stirred for a further 16 hours. The mixture was poured into dilute aqueous sodium hydroxide solution and extracted with ethyl acetate. The extracts yielded a gum which was dissolved in ether and treated with hydrogen chloride to give 7-benzyloxy-6-methoxy-2 -methyl-1-[1-(4-trifluoromethoxyphenyl)cyclobutyl]- 1,2,3,4-tetrahydroisoquinoline as the hydrochloride salt.

A mixture of 7-benzyloxy-6-methoxy-2-methyl-1-[1-(4-trifluoromethoxyphenyl)cyclobutyl] -1,2,3,4-tetrahydroisoquinoline hydrochloride (2.94 g), industrial methylated spirits (65 ml) and concentrated hydrochloric acid (65 ml) was heated under reflux for 45 minutes. The mixture was concentrated, and dried by azeotropic distillation with propan-2-ol. The residue was dissolved in ether and treated with one equivalent of oxalic acid to yield 7-hydroxy-6-methoxy-2-methyl-1-[1-( 4-trifluoromethoxyphenyl)cyclobutyl]-1,2,3, 4-tetrahydroisoquinoline oxalate which was crystallised from acetonitrile.

EXAMPLE 73

A mixture of (2-methoxyphenyl)acetonitrile (147 g and 1,2-dibromomethane (168 ml) in dimethylsulphoxide (250 ml) was added over 1 hour to a stirred suspension of powdered potassium hydroxide (250 g) and 18-Crown-6 (5 g) in dimethylsulphoxide (1200 ml) at 25° C. Stirring was continued for 20 hours. Water (1200 ml) was added and the mixture extracted with ether to give a crude oil which was purified by distillation (b.p. 102°/0.25) to give 1-(2-methoxyphenyl)cyclopropane carbonitrile.

1-(2-methoxyphenyl)cyclopropane carbonitrile (24 g) was heated under reflux for 20 hours with 10% aqueous potassium hydroxide solution (150 ml). After cooling, the solution was washed with toluene and then ether. The aqueous layer was acidified with excess hydrochloric acid to give 1-(2-methoxyphenyl)cyclopropane carboxylic acid.

1-(2-methoxyphenyl)cyclopropane carboxylic acid (19 g) and thionyl chloride (30 ml) were heated under gentle reflux for 2 hours. The solvent was evaporated to yield 1-(2-methoxyphenyl)cyclopropane carbonyl chloride.

A solution of 1-(2-methoxyphenyl)cyclopropane carbonyl chloride (16 g) in ethyl acetate (50 ml) was added to a stirred solution of 4-benzyloxy-3-methoxyphenylethylamine hydrochloride (22.3 g) in ethyl acetate (250 ml) and triethylamine (30 ml). The mixture was stirred for 3 days then water was added. The organic layer was washed with 5M-HCl, then water, then 2M aqueous sodium hydroxide solution, and dried over sodium sulphate. Evaporation yielded N-[2-(4-benzyloxy-3-methoxyphenyl)ethyl] -1-(2-methoxyphenyl)cyclopropane carboxamide.

A mixture of N-[2-(4-benzyloxy-3-methoxyphenyl)ethyl] -1-(2-methoxyphenyl)cyclopropane carboxamide (30.3 g) in acetonitrile (450 ml) and phosphoryl chloride (50 ml) was heated under reflux for 80 minutes. The solvent was evaporated in vacuo below 50° C. and the residue washed with ethyl acetate and then stirred with ethyl acetate (300 ml) and ice-cold 5% aqueous ammonia solution (200 ml) for 10 minutes. The organic layer was dried over potassium carbonate and the solvent removed by evaporation to give 7-benzyloxy-6-methoxy-1-[1-(2-methoxyphenyl)cyclopropyl] -3,4-dihydroisoquinoline.

Sodium cyanoborohydride (7.4 g) was added to a stirred mixture of 7-benzyloxy-6-methoxy-1-[1-(2-methoxyphenyl) cyclopropyl]-3,4-dihydroisoquinoline (23.3 g) , acetic acid (125 ml) and methanol (65 ml) cooled by ice/water. After 16 hours at ambient temperature the mixture was added to sodium hydroxide (110 g) and ice. The product was extracted into ether and the organic layer dried over potassium carbonate and the solvent removed by evaporation to yield a solid. The solid (16.9 g) in industrial methylated spirits (1800 ml) was stirred for 3 days with 1M aqueous sodium hydrogen phosphite [340 ml prepared from phosphorous acid (27.9 g) and sodium hydrogen carbonate (28.5 g)] and 37-40% aqueous formaldehyde solution (180 ml). The solution was concentrated in vacuo to a volume of 200 ml and basified with potassium carbonate (40 g) in water (200 ml). The mixture was extracted with ether and the solvent removed from the extract to give a gum which was purified by azeotropic distillation with industrial methylated spirits then propan-2-ol to yield 7 -benzyloxy-6-methoxy-1-[1-(2-methoxyphenyl)cyclopropyl]- 2-methyl-1,2,3,4-tetrahydroisoquinoline which was heated under reflux for 30 minutes with ethanol (200 ml) and concentrated hydrochloric acid (200 ml). The solvent was removed in vacuo to yield a solid which was dried by azeotropic distillation with propan-2-ol to produce a residue which was dissolved in acetonitrile (200 ml). Ethyl acetate (450 ml) was added, and the mixture boiled. The solution was decanted and evaporated in vacuo to give a residue which was triturated with cold ethyl acetate. The filtrate deposited further crystalline solid which was collected by filtration, washed in ethyl acetate and dried. The product yielded was 7-hydroxy-6-methoxy-1-[1-(2-methoxyphenyl)cyclopropyl] -2-methyl-1, 2,3,4-tetrahydroisoquinoline hydrochloride, m.p. 118° C.

EXAMPLE 74

A mixture of 7-benzyloxy-1-[1-(2-chlorophenyl)cyclopropyl] -6-methoxy-1,2,3,4-tetrahydroisoquinoline hydrobromide (5 g prepared as described in Example RC14), methanol (100 ml) and 37% aqueous formaldehyde solution (5 ml) was cooled to 10° C. Sodium borohyride (2.5 g) was added and the mixture stirred at ambient temperature for 2 hours. The methanol was evaporated in vacuo and the residue partitioned between dilute aqueous sodium hydroxide solution (100 ml) and ether (2×100 ml). The organic layer yielded an oil which was dissolved in methanol (25 ml) and concentrated hydrochloric acid (25 ml) and heated under reflux for 2 hours. The solvent was removed in vacuo and the residue dissolved in hot ethanol, decolorised, filtered and the solvent evaporated. The resulting solid was washed in ether, dried and then partitioned between ethyl acetate and concentrated aqueous ammonia solution. The organic layer yielded an oil which was dissolved in methanol. 48% Aqueous hydrobromic acid was added and the mixture heated under reflux for 2 hours. The solvents were removed by evaporation to yield a solid which was recrystallised from ethanol. The solid residue was washed with ether and dried in vacuo at 50° C. to give 1-[1-(2-chlorophenyl)cyclopropyl] -7-hydroxy-6 -methoxy-2-methyl-1,2,3,4-tetrahydroisoquinoline hydrobromide, m.p. 150°–153° C. Yield 2.95 g.

EXAMPLE 75

A mixture of 7-benzyloxy-1-[1-(2-chlorophenyl)cyclopropyl] -6-methoxy-1,2,3,4-tetrahydroisoquinoline (2.1 g, free base liberated from the hydrobromide salt prepared in a similar manner to that described in Example RC14), acetone (30 ml), anhydrous potassium carbonate (1.6 g) and 2-methoxyethyl bromide (2.1 g) was heated under reflux for 6 hours. After a further 16 hours at ambient temperature, potassium carbonate (3 g) and 2-methoxyethyl bromide (2.22 g) were added, and heating continued for 6 hours. The mixture was filtered, the residue washed with acetone, and solvent removed from the filtrate in vacuo to yield 7-benzyloxy-1-[1-(2-chlorophenyl)cyclopropyl] -6-methoxy-2-(2-methoxyethyl)- 1,2,3,4-tetrahydroisoquinoline as an oil.

A mixture of the oil, ethanol (25 ml) and concentrated hydrochloric acid (25 ml) was heated under reflux for 30 minutes. The solvent was removed in vacuo, and the residue dried by azeotropic distillation with ethanol. The resulting residue was triturated with ethyl acetate to give a solid which was collected by filtration, washed with ethyl acetate and dried at 40° C. in vacuo to give 1-[1-(2-chlorophenyl)cyclopropyl]-7 -hydroxy-6-methoxy-2-(2-methoxyethyl)-1,2, 3,4-tetrahydroisoquinoline (1.5 g) , m.p. 115°–120° C.

EXAMPLE 76

A mixture of 7 -benzyloxy-1-[1-(2 -chlorophenyl)cyclopropyl] -6-methoxy-1,2,3,4-tetrahydroisoquinoline (2.83 g, liberated from the hydrobromide salt prepared in a similar manner to that described in Example RC14), acetone (40 ml), anhydrous potassium carbonate (5.5 g) and 2-bromoethanol (3.6 ml) was heated under reflux for 18 hours. The mixture was filtered, the solids washed with acetone, and the filtrate solvent removed in vacuo to give 7-benzyloxy-1-[1-(2-chlorophenyl)cyclopropyl]-2-( 2-hydroxyethyl)-7-methoxy-1,2,3,4-tetrahydroisoquinoline as an oil.

A mixture of the oil, ethanol (30 ml) and concentrated hydrochloric acid (30 ml) was heated under reflux for 30 minutes. The solvent was removed in vacuo, and the residue dried by azeotropic distillation with a mixture of ethanol and toluene. The resulting gum was digested with boiling ethyl acetate and the residue dried at 45° in vacuo to give a solid which was collected by filtration and washed with ethyl acetate. The resulting solid was dissolved in warm water and the resulting solution basified by addition of a slight excess of aqueous ammonia solution to yield a solid which was dissolved in ethyl acetate. The resulting solution was dried over magnesium sulphate and the solvent removed in vacuo to yield a gum which formed a glass on cooling. The product was 1-[1-(2-chlorophenyl)cyclopropyl] -7-hydroxy-2-(2-hydroxyethyl)-6 -methoxy-1,2,3,4-tetrahydroisoquinoline (0.76 g), m.p. 65°–70° C.

EXAMPLE 77

1-[1-(2-chlorophenyl)cyclopropyl]-7-hydroxy-6 -methoxy-2-methyl-1,2,3,4-tetrahydroisoquinoline free base (prepared from the salt described in Example 74) was resolved by preparative chiral high performance liquid chromatography on a Chiracel AD column eluted with a 9:1 mixture of hexane and ethanol. The solvent was removed from fraction 1 in vacuo and the residue treated with 48% aqueous hydrobromic acid. The water was evaporated in vacuo and the residue dried by azeotropic distillation with propan-2-ol. The resulting solid was washed with petroleum ether (b.p.

60°–80° C.), collected by filtration and dried in vacuo to yield (+)- 1-[1-(2-chlorophenyl)cyclopropyl]-7-hydroxy-6-methoxy-2-methyl-1,2,3,4-tetrahydroisoquinoline hydrobromide which had a specific optical rotation $\alpha_D$ of +14.6, m.p. 154°–157° C.

EXAMPLE 78

A mixture of 6,7-dimethoxy-1-[1-(4-biphenylyl)cyclobutyl]-1,2,3,4-tetrahydroisoquinoline hydrochloride (3.5 g, prepared as described in Example RC20), methanol (50 ml), 37% aqueous formaldehyde solution (5 ml) and sodium cyanoborohydride (2.08 g) was stirred at ambient temperature for 24 hours. The solvents were removed in vacuo and the residue was partitioned between aqueous sodium hydroxide solution and ether. The ether extracts were dried over magnesium sulphate, the solution was filtered and the solvent removed in vacuo. The residue was dissolved in glacial acetic acid (30 ml). 48% Aqueous hydrobromic acid (30 ml) was added, and the mixture was heated under reflux under nitrogen for 6 hours. The solvents were removed in vacuo and the residue was recrystallised from methanol to give a solid which was partitioned between concentrated aqueous ammonia solution and ether. The ether extracts were washed with brine, dried and filtered. Dry hydrogen chloride was bubbled through the filtrate to yield 6,7-dihydroxy-2-methyl-1-[1-(4-biphenylyl)cyclobutyl]-1,2,3,4-tetrahydroisoquinoline hydrochloride (1.1 g), m.p. 131°–135° C. (dec).

EXAMPLE 79

1-[1-(2-Chlorophenyl)cyclopropyl]carbonyl chloride (16.9 g) was added dropwise at 0° C. under nitrogen to a suspension of 2-(4-methoxy-3-methylphenyl)ethylamine (13 g, prepared in a similar manner to that described in Example 10) and triethylamine (11.8 ml) in tetrahydrofuran (200 ml). The reaction mixture was stirred at ambient temperature for 16 hours, then poured onto aqueous sodium hydroxide solution and stirred for 1 hour. The product was extracted witch ethyl acetate. The extracts were dried over magnesium sulphate and the solvent was concentrated to give N-[2-(4-methoxy-3-methylphenyl)ethyl]-1-(2-chlorophenyl)cyclopropane-carboxamide which was used without further purification.

A mixture of the amide and 82% w/w solution of polyphosphate ester in chloroform (170 g) was heated gently for 16 hours, then poured into water (1200 ml) and the mixture washed with ether. The aqueous phase was basified by addition of aqueous ammonia solution and the product was extracted with ethyl acetate. The extracts were dried and concentrated to give 1-[1-(2-chlorophenyl)cyclopropyl]-7-methoxy-6-methyl-3,4-dihydroisoquinoline as a solid. Yield 14.7 g.

Sodium cyanoborohydride (5.3 g) was added portionwise to a solution of 1-[1-(2-chlorophenyl)cyclopropyl]-7-methoxy-6-methyl-3,4-dihydroisoquinoline (14 g) in methanol (70 ml) and acetic acid (140 ml). The mixture was stirred for 1 hour, concentrated, and the residue then treated with aqueous sodium hydroxide solution. The resulting mixture was extracted with ethyl acetate and the extracts were washed with brine and dried over magnesium sulphate. 1-[1-(2-Chlorophenyl)cyclopropyl]-7-methoxy-6-methyl-1,2,3,4-tetrahydroisoquinoline crystallised from the extract and was collected by filtration (6.5 g).

A mixture of 1-[1-(2-chlorophenyl)cyclopropyl]-7-methoxy-6-methyl-1,2,3,4-tetrahydroisoquinoline (6.2 g), methanol (160 ml) and 37–40% aqueous formaldehyde solution was stirred for 15 minutes. Sodium cyanoborohydride (5.13 g) was added and the mixture was stirred for a further 10 minutes. The reaction was then neutralised with acetic acid and stirred for 45 minutes. The methanol was removed in vacuo and the residue treated with aqueous sodium hydroxide solution. The product was extracted with ethyl acetate. The extracts were washed with aqueous ammonia solution, water and brine, then dried over magnesium sulphate. Concentration yielded 1-[1-(2-chlorophenyl)cyclopropyl]-7-methoxy-2,6-dimethyl-1,2,3,4-tetrahydroisoquinoline as a gum (5.02 g).

A mixture of the gum (5.02 g), 48% aqueous hydrobromic acid (120 ml) and glacial acetic acid (120 ml) was heated at 90°–95° C. for 16 hours. The reaction was neutralised by addition of aqueous sodium hydroxide solution and the product extracted with ethyl acetate. The extracts were concentrated and the residue redissolved in propan-2-ol (150 ml) containing concentrated aqueous hydrochloric acid (2 ml). The solution was concentrated and dried by azeotropic distillation with propan-2-ol to give a solid. The solid was washed with ethyl acetate and dried to give 1-[1-(2-chlorophenyl)cyclopropyl]-7-hydroxy-2,6-dimethyl-1,2,3,4-tetrahydroisoquinoline hydrochloride. Yield 4.5 g, m.p. 159°–161° C. (dec).

EXAMPLE 80

1-[1-(2-Chlorophenyl)cyclopropyl]-7-hydroxy-2,6-dimethyl-1,2,3,4-tetrahydroisoquinoline (2.0 g liberated from the salt prepared as described in Example 79) was resolved by chiral preparative high performance liquid chromatography on a Chiracel OD column eluted with a 1:19 mixture of propan-2-ol and hexane. Fraction 1 was converted into its hydrobromide salt using 48% aqueous hydrobromic acid in propan-2-ol to yield (+)-1-[1-(2-chlorophenyl)cyclopropyl]-7-hydroxy-2,6-dimethyl-1,2,3,4-tetrahydroisoquinoline hydrobromide. The salt had a specific optical rotation $\alpha_D$ of +5.6°, m.p. 170°–175° C. (dec). Yield 0.8 g.

EXAMPLE 81

Sodium cyanoborohydride (2.8 g) was added at 5° C. to a mixture of 1-[1-(2,4-dichlorophenyl)cyclopropyl]-6-fluoro-7-methoxy-1,2,3,4-tetrahydroisoquinoline hydrobromide (10 g, prepared as described in Example RC4), methanol (100 ml) and 37–40% aqueous formaldehyde solution (7.2 ml). The mixture was warmed to ambient temperature and stirred for 1.5 hours. The solvent was removed in vacuo and the residue partitioned between water and dichloromethane. The organic phase was washed with concentrated ammonia solution, then water, and dried over magnesium sulphate. The solvent was removed in vacuo to yield 1-[1-(2,4-dichlorophenyl)cyclopropyl]-6-fluoro-7-methoxy-2-methyl-1,2,3,4-tetrahydroisoquinoline as a gum which solidified on standing.

A mixture of 1-[1-(2,4-dichlorophenyl)cyclopropyl]-6-fluoro-7-methoxy-2-methyl-1,2,3,4-tetrahydroisoquinoline (8.5 g), 48% aqueous hydrobromic acid (100 ml) and glacial acetic acid (100 ml) was heated under reflux for 2 hours. The solvents were removed in vacuo and the residue dried by azeotropic distillation with propan-2-ol. The resulting solid was recrystallised from propan-2-ol to yield 1-[1-(2,4-dichlorophenyl)cyclopropyl]-6-fluoro-7-hydroxy-2-methyl-1,2,3,4-tetrahydroisoquinoline hydrobromide (7.2 g), m.p. 235°–237° C.

EXAMPLE 82

N,N,N',N'-Tetramethylethylenediamine (231.4 g) was added at ambient temperature to a solution of n-butyl lithium (2.5M, 800 ml) in hexane (2.5 l) followed by a solution of 2,3-dihydrobenzo[b]furan (102 g) in hexane (25 ml). The mixture was stirred under nitrogen at ambient temperature for 5 hours. The resulting suspension was added slowly to dry ice (300 g) and hexane (500 ml) under nitrogen. After stirring at ambient temperature for 16 hours, the mixture was diluted with water (2 l), and the layers separated. The aqueous layer was washed with hexane, acidified to pH 1 with concentrated hydrochloric acid, cooled and the precipitate collected by filtration. This was washed with water and dichloromethane and dried at 80° C. in vacuo to give 2,3-dihydrobenzo[b]furan-7-carboxylic acid (39.6 g), m.p. 164°–165° C. The hexane layer was filtered, dried over sodium sulphate and concentrated. On cooling, further product was obtained (32.7 g), m.p. 170° C.

Borane dimethyl-sulphide complex (60 ml) was added to a stirred solution of the above acid (70.2 g) and tetrahydrofuran (500 ml). The mixture was stirred for 30 minutes, then water (200 ml) was carefully added. The tetrahydrofuran was removed in vacuo. Water (200 ml) and then aqueous sodium hydroxide solution were added. The product was extracted into ether, and the extracts dried over potassium carbonate. The solvent was removed in vacuo to yield 7-hydroxymethyl-2,3-dihydrobenzo[b]furan (50 g) as an oil.

A solution of the above oil (50 g) in dichloromethane (200 ml) was treated portionwise at 20° C. with thionyl chloride (50 ml) over 10 minutes. The solution was warmed, and the solvent removed in vacuo to give 7-chloromethyl-2,3-dihydrobenzo[b]furan as an oil which was used without further purification.

A solution of sodium cyanide (45 g) in water (200 ml) was added to a mixture of the above oil in toluene (200 ml). Tetrabutylammonium bromide (2 g) was added. The mixture was heated under reflux with vigorous stirring for 3 hours. After standing for 16 hours, the mixture was decolourised by addition of charcoal. The mixture was filtered, separated, and the organic layer dried over sodium sulphate. The solvent was removed in vacuo to give an oil (40 g) which was purified by distillation at 144–160° C./4 mbar and then at 90°–112° C./0.4 mbar. The distillate was heated with dimethylsulphoxide (50 ml) and sodium cyanide (6 g) at 90°–95° C. for 8 hours with the exclusion of moisture. The mixture was then added to water and the product was extracted into ether. The extracts were dried over potassium carbonate and the solvent was removed in vacuo to yield an oil.

A mixture of the oil, toluene (60 ml), pyridine (2.2 ml) and phthalic anhydride (4 g) was heated at 90°–95° C. for 4 hours. The resulting solution was cooled, washed with 10% aqueous potassium carbonate solution, then with dilute hydrochloric acid. The solution was then dried over sodium sulphate and the solvent removed in vacuo to yield an oil. The oil was distilled, (b.p. 120° C./1 mbar) to give 2,3-dihydrobenzo[b]furan-7-ylacetonitrile which rapidly solidified (16.97 g).

The solid (16.97 g) was melted and dissolved in dimethylsulphoxide (100 ml). 1,2-Dibromoethane (18 ml) was added and the mixture was added at 1 drop/second at 20°–30° C. to a stirred mixture of solid potassium hydroxide (50 g), dimethylsulphoxide (150 ml) and 18-Crown-6 (1.5 g). The mixture was stirred for a further 16 hours. 1,2-Dibromoethane (10 ml) was added and the stirring continued for 8 hours. The mixture was allowed to stand at ambient temperature for 16 hours. 1,2-Dibromoethane (8 ml) was added, the mixture was stirred for 6 hours, then further 1,2-dibromoethane (10 ml) was added and the mixture stood for 3 days. The mixture was added to water and the product was extracted with ether. The extracts were dried over potassium carbonate, the solvent removed in vacuo, and the residue distilled (b.p. 120° C./0.25 mbar) to yield 1-[2,3-dihydrobenzo[b]-furan-7-yl]cyclopropane carbonitrile as a solid (11.2 g).

A mixture of the above solid (11.2 g), potassium hydroxide (30 g) and water (300 ml) was stirred and heated under reflux for 6 hours. The resulting solution was washed with ether and the aqueous phase acidified by addition of excess hydrochloric acid, to give a solid which was collected by filtration, washed with water and dried in air to yield 1-[2,3-dihydrobenzo[b]furan-7-yl]cyclopropane carboxylic acid.

The above carboxylic acid (7.7 g) was warmed with thionyl chloride (20 ml) then heated under reflux for 20 minutes. Excess thionyl chloride was boiled off. Distillation yielded an oil (b.p. 70° C./50 mbar) which was dissolved in ethyl acetate (50 ml). The solution was added to a stirred mixture of 2-(4-benzyloxy-3-methoxyphenyl)ethylamine hydrochloride (15.7 g), ethyl acetate (200 ml) and triethylamine (30 ml) and the mixture stirred for 64 hours. Water was added. The ethyl acetate layer was washed with water, dilute aqueous sodium hydroxide solution, dilute hydrochloric acid and water, then dried over sodium sulphate. The solvent was removed in vacuo to give a gum which was purified by flash chromatography using ether as the eluant to give N-[2-(4-benzyloxy-3-methoxyphenyl)ethyl]- 1-[2,3-dihydrobenzo[b]furan-7-yl]cyclopropane carboxamide which was dissolved in acetonitrile (200 ml). Phosphoryl chloride (20 ml) was added and the mixture heated under reflux for 80 minutes. The solvent and excess phosphoryl chloride were removed in vacuo and the residue was dissolved in ethyl acetate. Ether was added causing an oil to separate. The supernatant liquid was decanted and ether was added until no further oil separated. The oil was triturated with ether, then added to a mixture of dilute aqueous ammonia and ether. The ether layer was dried over potassium carbonate and the solvent removed in vacuo to give 7-benzyloxy-1-[1-( 2,3-dihydrobenzo[b]furan-7-yl)cyclopropyl]-6-methoxy- 3,4-dihydroisoquinoline as a gum (11.1 g).

A mixture of the above gum (11.1 g), acetic acid (60 ml) and methanol (30 ml) was stirred for 2 hours, then cooled in ice/water. Sodium cyanoborohydride in tetrahydrofuran (1M solution, 53 ml) was added and the mixture stirred for 2 hours. Water, then excess aqueous ammonia solution were added and the product was extracted with ether. The solvent was removed in vacuo to yield a gum which was used without further purification.

1M aqueous sodium hydrogen phosphite [218 ml, prepared from phosphorous acid (17.9 g) in water and sodium bicarbonate (18.3 g)] was added to a mixture of the gum and industrial methylated spirits (1.15 l). 37–40% Aqueous formaldehyde solution (115 ml) was added and the resulting solution was allowed to stand for 64 hours. The solution was concentrated in vacuo to 200 ml, filtered and decanted to remove traces of gum. The solution was diluted with water, basified by addition of excess aqueous ammonia solution, and the product was extracted into ether. The extracts were dried over sodium sulphate and the solvent removed in vacuo to yield an oil. The oil was purified by column chromatography using a 19:1 mixture of ether and triethylamine as eluant. The fractions were purified by high pressure liquid chromatography. Fractions 1 and 2 (9.46 g) were combined.

A mixture of fractions 1 and 2 (9.46 g), 98–100% formic acid (25 ml) and methanol (125 ml) under argon was treated with 10% palladium on charcoal (3 g) was added and argon bubbled through for 24 hours. 48% Aqueous hydrobromic acid (3.6 ml) was added and the mixture was filtered and the solvent removed from the filtrate in vacuo. The residue was dried by azeotropic distillation with ethanol (100%) to give a solid which was washed with ethyl acetate, dried in air and then in vacuo at 45° C.

The solid was dissolved in water, basified by addition of aqueous ammonia solution and extracted with ethyl acetate. The extract was dried over sodium sulphate and the solvent removed in vacuo to leave a small volume. Ether was added and 1-[1-(2,3-dihydrobenzo[ b]furan-7-yl)cyclopropyl]-7-hydroxy-6-methoxy-2 -methyl-1,2,3,4-tetrahydroisoquinoline (5.18 g), m.p. 156° C. was collected by filtration and washed with ether.

EXAMPLE 83

A mixture of N-[2-(3,4-dimethoxyphenyl)ethyl]cyclobutanecarboxamide (44 g, prepared in a similar manner to that described in Example E46), phosphorus oxychloride (150 ml) and acetonitrile (900 ml) was heated under reflux for 2.5 hours. The cooled solution was poured onto dilute aqueous ammonia solution and the product was extracted into ethyl acetate. The extracts were washed with brine, dried and the solvent removed in vacuo. The resulting oil solidified on standing for 16 hours. The solid was recrystallised from petroleum ether (b.p. 60°– 80° C.) to give 1-cyclobutyl-3,4-dihydro-6,7-dimethoxyisoquinoline (20 g).

n-Butyl lithium (24.5 ml, 2M solution in hexane) was added to a solution of diisopropylamine (6.85 ml) in tetrahydrofuran (50 ml) at 0° C. The resulting solution of lithium diisopropylamide was stirred at 0° C. for 20 minutes. A solution of 1-cyclobutyl-3,4-dihydro-6,7-dimethoxyisoquinoline (10 g) in tetrahydrofuran (100 ml) was added. The mixture was stirred at 0° C. for 1 hour, then cooled to −70° C. and treated dropwise with 2-fluorobenzonitrile (4.42 ml). The mixture was stirred at −70° C. for 50 minutes, then allowed to warm slowly to ambient temperature. The mixture was poured onto hydrochloric acid and washed with ether. The aqueous phase was basified with ammonia solution and the product was extracted with ethyl acetate. The resulting solid (0.6 g) was collected by filtration. The filtrate was washed with brine, dried over magnesium sulphate and the solvent removed in vacuo to give further solid. The combined solids were recrystallised from acetonitrile yielding a solid which was dried in vacuo to give 1-[1-( 2-cyanophenyl)cyclobutyl]-6,7-dimethoxy-3,4-dihydroisoquinoline (5 g).

A mixture of the dihydroisoquinoline (5 g), acetonitrile (150 ml) and methyl iodide (18 ml) was heated under gentle reflux for 64 hours. The solvent was removed in vacuo and the residue was washed with ether. The solid was collected by filtration and dried in vacuo to yield 1-[1-(2-cyanophenyl)cyclobutyl]-6,7 -dimethoxy-2-methyl-3,4-dihydroisoquinolinium iodide (6.7 g).

Sodium borohydride (0.465 G) was added portionwise to a mixture of 1-[1-(2-cyanophenyl)cyclobutyl]-6,7 -dimethoxy-2-methyl-3,4-dihydroisoquinolinium iodide (6 g) and methanol (40 ml). The mixture was stirred for 2 hours then poured onto aqueous sodium hydroxide solution and the product extracted into ether. The solvent was removed from the extracts to give a gum which was dissolved in ethyl acetate and a little propan-2-ol. A 0.4M solution of (±)-dibenzoyltartaric acid in ether (35 ml) was added and the resulting suspension was concentrated in vacuo. The residual solid was washed with ether to give 1-[1-(2-cyanophenyl)cyclobutyl] -6,7-dimethoxy-2-methyl-1,2,3,4-tetrahydroisoquinoline (±)-dibenzoyltartrate (7.2 g), m.p. 109°–112° C. (dec).

The (±)-dibenzoyltartrate salt (2 g) was neutralised with aqueous saturated sodium hydrogen carbonate solution and extracted with ethyl acetate. The extracts were dried and the solvents removed to give 1-[1-(2-cyanophenyl)cyclo-butyl] -6,7-dimethoxy-2-methyl- 1,2,3,4,-tetrahydroisoquinoline free base (1 g) which was dissolved in dichloromethane (5 ml). The solution was cooled to −70° C. and treated dropwise with a 1M solution of boron tribromide in dichloromethane (3 ml). After 30 minutes the mixture was allowed to warm to ambient temperature, and then stirred for 90 minutes. The mixture was cooled to −70 ° C. and further dichloromethane (7 ml ) and a solution of 1M boron tribromide in dichloromethane (3 ml ) were added. The mixture was warmed to room temperature and stirred for 1 hour then cooled to −40° C. and an excess of methanol was added. The mixture was warmed to ambient temperature and methanol (100 ml) was added. The solvents were distilled off in vacuo and the trimethylborate removed by azeotropic distillation with methanol.

The residue was neutralised with aqueous saturated sodium hydrogen carbonate solution and extracted with ethyl acetate. The extracts were treated with excess ethereal hydrogen chloride. The solvent was removed in vacuo to yield 1-[1-(2-cyanophenyl)cyclobutyl]-6,7 -dihydroxy-2-methyl-1,2,3,4-tetrahydroisoquinoline (0.4 g), m.p. 206°–208° C. (dec).

EXAMPLE 84

Methyl iodide (15 ml) was added to a solution of 7 -benzyloxy-1-[1-(2-chlorophenyl)cyclopentyl]-6-methoxy-3,4-dihydroisoquinoline (13 g, prepared as described in Example CA34) in acetonitrile (100 ml). The mixture was heated under reflux for 24 hours, cooled and the resulting solid collected by filtration. The solid was washed with ether and dried in air to give 7-benzyloxy- 1-[1-(2-chlorophenyl)cyclopentyl]-6-methoxy-2-methyl- 3,4-dihydroisoquinolinium iodide (10 g).

Sodium borohydride (2.6 g) was added portionwise to a mixture of 7-benzyloxy-1-[1-(2-chlorophenyl)cyclopentyl] -6-methoxy-2-methyl-3,4-dihydroisoquinolinium iodide (10 g) and methanol (250 ml). The mixture was stirred at ambient temperature for 1 hour, heated under reflux for 1 hour, then cooled to ambient temperature. Sodium borohydride (5 g) was added and the mixture stirred at ambient temperature for 30 minutes. The resulting solid was collected by filtration, washed with ether and dissolved in acetone. Insoluble particles were removed by filtration and the solvent was removed from the filtrate in vacuo to yield 7-benzyloxy-1-[1-(2-chlorophenyl)cyclopentane] -6-methoxy-2-methyl-1,2,3,4tetrahydroisoquinoline (3.8 g).

A mixture of the above tetrahydroisoquinoline (3.8 g), methanol (25 ml) and concentrated hydrochloric acid (25 ml) was heated under reflux for 3.5 hours. The solvents were removed in vacuo and the residue recrystallised from methanol. The resulting solid was washed twice with ether and dried to yield 1-[1-(2-chlorophenyl)cyclopentyl] -7-hydroxy-6-methoxy-2-methyl- 1,2,3,4-tetrahydroisoquinoline hydrochloride (2.8 g), m.p. 119°–121° C. (dec).

EXAMPLE 85

A solution of 7-benzyloxy-1-[1-(2-chlorophenyl)cyclopropyl] -6-methoxy-3,4-dihydroisoquinoline (0.5 g, prepared in a similar manner to that described in Example CA281) in dichloromethane (10 ml) was added dropwise at −40° C. to a stirred solution of sodium tris[N-(2-methylpropyloxycarbonyl)prolyloxy]borohydride (2.43 g) in dichloromethane (10 ml). The mixture was allowed to reach ambient temperature and was stirred for 49 hours. Dilute sulphuric acid (10 ml, 10% v/v) was added, and stirring continued for 1 hour. The mixture was basified by addition of saturated aqueous sodium carbonate solution. The organic layer was washed with brine, dried over magnesium sulphate and the solvent removed in vacuo to yield 7-benzyloxy-1-[1-(2-chlorophenyl)cyclopropyl] -6-methoxy-1,2,3,4-tetrahydroisoquinoline as a gum (0.42 g). This product was shown to have a 92% enantiomeric excess of one of the enantiomers.

A mixture of the enantiomerically enriched 7 -benzyloxy-1-[1-(2-chlorophenyl)cyclopropyl]-6-methoxy- 1,2,3,4-tetrahydroisoquinoline (0.41 g), anhydrous potassium carbonate (0.4 g), methyl iodide (0.152 g) and acetone (25 ml) was stirred at ambient temperature for 2 hours. The solvent was removed in vacuo and the residue dissolved in water and extracted with ether. The extracts were concentrated in vacuo. A mixture of the residue, concentrated hydrochloric acid (5 ml) and methanol (5 ml) was heated under reflux for 2 hours. The solvents were removed in vacuo and the residue partitioned between saturated aqueous sodium bicarbonate solution and ether. The ether layer was concentrated in vacuo and the residue dissolved in propan-2-ol and acidified with 48% aqueous hydrobromic acid. The solution was concentrated in vacuo to yield (+)-1-[1-(2-chlorophenyl)cyclopropyl] -7-hydroxy-6-methoxy-2-methyl- 1,2,3,4-tetrahydroisoquinoline hydrobromide (0.24 g).

EXAMPLE 86

Decanoyl chloride (0.45 g) was added to a mixture of (+)-1-[1-(2-chlorophenyl)cyclopropyl]-7-hydroxy-6 -methoxy-2-methyl-1,2,3,4-tetrahydroisoquinoline hydrobromide (1 g, prepared in a similar manner to that described in Example 77), triethylamine (0.7 g) and ether (30 ml). The mixture was stirred at ambient temperature for 24 hours, then washed with water, 10% aqueous sodium hydroxide solution, and brine. The organic layer was dried over magnesium sulphate, filtered and concentrated to yield a gum which was purified by chromatography on a silica gel column using a 1:3 mixture of ether and light petroleum as eluant. The relevant fractions were concentrated in vacuo to yield (+)-1-[1-(2-chlorophenyl)cyclopropyl]-7 -decanoyloxy-6-methoxy-2-methyl-1,2,3,4-tetrahydroisoquinoline (0.95 g) as a gum; having specific optical rotation $\alpha_D$ of +21.47°.

EXAMPLE 87

Decanoyl chloride (0.66 g) in dichloromethane (5 ml) was added to a stirring mixture of (+)-1-[1-(2-chlorophenyl)cyclobutyl] -6-fluoro-7-hydroxy-2-methyl-1,2,3,4 -tetrahydroisoquinoline hydrobromide (1.5 g, prepared in a similar manner to that described in Example 64), triethylamine (1.06 g) and dichloromethane (25 ml). The mixture was stirred at ambient temperature for 20 minutes, then water (20 ml) was added and stirring continued for 1 hour. The organic layer was washed with saturated aqueous sodium bicarbonate solution, water and brine, then dried over magnesium sulphate, filtered and concentrated in vacuo to yield (-)-1-[1-(2-chlorophenyl)cyclobutyl] -7-decanoyloxy-6-fluoro-2-methyl- 1,2,3,4-tetrahydroisoquinoline (1.31 g). This had a specific optical rotation $\alpha_D$ of −5.59°.

EXAMPLE 88

Decanoyl chloride (0.61 g) was added to a stirring suspension of (+)-1- [1-(2-chlorophenyl)cyclopropyl]-6 -fluoro-7-hydroxy-2-methyl-1,2,3,4-tetrahydroisoquinoline hydrobromide (1 g, prepared in a similar manner to that described in Example 62) and dichloromethane (25 ml). Triethylamine (1.35 ml) was added and the stirring was maintained for 1.5 hours. Water was then added, and the organic layer washed with 2N aqueous sodium hydroxide solution, then water and dried over potassium carbonate. The solvent was removed in vacuo and the residual oil was purified by liquid chromatography using petroleum ether (b.p. 40°–60° C.) as impurity eluant, then 5% ether in petroleum ether (b.p. 40°–60° C.) as product eluant. The solvent was removed in vacuo to yield (+)-1-[1-(2-chlorophenyl)cyclopropyl] -7-decanoyloxy-6-fluoro-2 -methyl-1,2,3,4-tetrahydroisoquinoline (0.85 g) which had a specific optical rotation $\alpha_D$ of +10.6°.

EXAMPLE 89

Decanoyl chloride (0.5 g) in dichloromethane, then triethylamine (0.8 g) was added to a stirring mixture of 1-[1-(2-chlorophenyl)cyclopropyl]-6-fluoro-7-hydroxy-2 -methyl-1,2,3,4-tetrahydroisoquinoline hydrobromide (0.825 g, prepared in a similar manner to that described in Example 61) in dichloromethane (20 ml). After stirring for 1 hour, water was added, and the organic phase was washed with 2N aqueous sodium hydroxide solution then water. The organic phase was then dried over magnesium sulphate and the solvent removed in vacuo to yield 1-[1-(2-chlorophenyl)cyclopropyl]-7 -decanoyl-oxy-6-fluoro-2-methyl-1,2,3,4-tetrahydroisoquinoline (0.85 g).

EXAMPLE 90

Hexadecanoyl chloride (0.83 g) in dichloromethane (5 ml) was added dropwise to a stirring solution of 1-[ 1-(2-chlorophenyl)cyclopropyl]-7-hydroxy-6-methoxy-2 -methyl-1,2,3,4-tetrahydroisoquinoline (1.04 g, prepared from the (+)-enantiomer of the hydrobromide salt, prepared in a similar manner to that described in Example 77), triethylamine (0.91 g) and dichloromethane (20 ml). The mixture was stirred at ambient temperature for 2 hours, then washed with dilute sodium hydroxide solution, water and brine. The organic phase was dried over magnesium sulphate, filtered and concentrated in vacuo. The resulting oil was dissolved in petroleum ether (b.p. 60°–80° C.) and washed repeatedly with water. The organic layer was dried over magnesium sulphate, filtered and concentrated in vacuo to yield (+)-1-[1-(2-chlorophenyl)cyclopropyl] -7-hexadecanoyloxy-6-methoxy-2 -methyl-1,2,3,4-tetrahydro-isoquinoline (1.45 g) which had a specific optical rotation $\alpha_D$ of +21.18°.

EXAMPLE 91

A solution of dodecanoyl chloride (0.737 g) in dichloromethane (5 ml) was added dropwise to a stirred solution of 1-[1-(2-chlorophenyl)cyclopropyl]-7-hydroxy- 6-methoxy-2-methyl-1,2,3,4-tetrahydroisoquinoline (1.16 g, free base liberated from the (+)-enantiomer of the hydrobromide salt prepared as described in Example 77), triethylamine (1.02 g) and dichloromethane (20 ml). The mixture was stirred at ambient temperature for 2 hours. The mixture was washed with dilute sodium hydroxide solution, water then brine. The organic layer was concentrated in vacuo and the residue partitioned between light petroleum ether and water.

The organic layer was washed with water, dried over magnesium sulphate, filtered and the solvent removed in vacuo to yield a gum. The gum was dissolved in petroleum ether and purified by flash chromatography using a 1:4 mixture of ether and petroleum ether as eluant. Removal of solvent from the eluate yielded (+)- 1-[1-(2-chlorophenyl)cyclopropyl]-7-dodecanoyloxy-6 -methoxy-2-methyl-1,2, 3,4-tetrahydroisoquinoline (0.81 g) which had a specific optical rotation $\alpha_D$ of +25.05°.

EXAMPLE 92

A solution of heptanoyl chloride (0.34 g) in dichloromethane (5 ml) was added dropwise to a stirred solution of 1-[1-(2-chlorophenyl)cyclopropyl]-7-hydroxy- 6-methoxy-2-methyl-1,2,3,4-tetrahydroisoquinoline (0.79 g, free base liberated from the (+)-enantiomer of the hydrobromide salt, prepared as described in Example 77), triethylamine (0.69 g) and dichloromethane (20 ml). The mixture was stirred at ambient temperature for 2 hours. The mixture was washed with dilute sodium hydroxide solution, water then brine. The organic layer was concentrated in vacuo and the residue partitioned between light petroleum ether and water.

The organic layer was washed with water, dried over magnesium sulphate, filtered and the solvent removed in vacuo to yield a gum. The gum was dissolved in petroleum ether and purified by flash chromatography using a 1:3 mixture of ether and petroleum ether as eluant. Removal of solvent from the eluate yielded (+)- 1-[1-(2-chlorophenyl)cyclopropyl]-7-heptanoyloxy-6 -methoxy-2-methyl-1,2,3, 4-tetrahydroisoquinoline (0.64 g) which had a specific optical rotation $\alpha_D$ of +23.04°.

EXAMPLE 93

A solution of octadecanoyl chloride (0.61 g) in dichloromethane (5 ml) was added dropwise to a stirred solution of 1-[1-(2-chlorophenyl) cyclopropyl]-7-hydroxy- 6-methoxy-2-methyl-1,2,3,4-tetrahydroisoquinoline (0.69 g, free base liberated from the (+)-enantiomer of the hydrobromide salt prepared as described in Example 77), triethylamine (0.61 g) and dichloromethane (20 ml). The mixture was stirred at ambient temperature for 2 hours. The mixture was washed with dilute sodium hydroxide solution, water then brine. The organic layer was concentrated in vacuo and the residue partitioned between light petroleum ether and water.

The organic layer was washed with water, dried over magnesium sulphate, filtered and the solvent removed in vacuo to yield a gum. The gum was dissolved in petroleum ether and purified by flash chromatography using a 1:3 mixture of ether and petroleum ether as eluant. This yielded (+)-1-[1-(2-chlorophenyl)cyclopropyl]  -6-methoxy-2-methyl-7-octadecanoyloxy-1,2,3,4-tetrahydroisoquinoline (0.41 g) which had a specific optical rotation $\alpha_D$ of +23.33°.

EXAMPLES MI

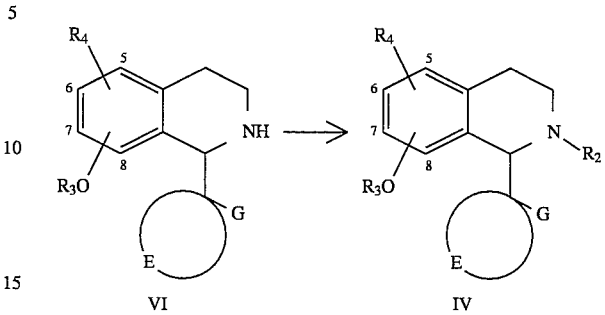

A mixture of a compound of formula VI in which $OR_3$, $R_4$ and G are as defined in Table MI and E is —$(CH_2)_3$— (a g), methyl iodide (b g), anhydrous potassium carbonate (c g) and acetone (d ml) was stirred at ambient temperature for e hours. The mixture was filtered and the solvent removed by evaporation. The residue was partitioned between ethyl acetate and water. The ethyl acetate layer yielded a residue which was treated as set out in the Notes below to give the desired compound of formula IV in which $OR_3$, $R_4$ and G are as defined in Table MI, $R_2$ is methyl and E is —$(CH_2)_3$—.

NOTES TO TABLE MI

ND indicates that the melting point was not determined.

MI1 The final residue was triturated with a 5:1 mixture of light petroleum ether (b.p. 60°–80° C.) and ether. The product was characterised by recrystallising a small sample from light petroleum ether. It is the melting point of this recrystallised sample which is given in Table MI.

MI2 The residue from the initial reaction was partitioned between ether and water. Evaporation of the ether layer yielded the product which was characterised by recrystallising a small sample from light petroleum ether. It is the melting point of this recrystallised sample which is given in Table MI.

MI3 The product was characterised by converting a small sample into its hydrochloride salt. The melting point of this salt is given in the last column of Table MI.

MI4 The product was characterised by recrystallising a small sample from petroleum ether (bp 60°–80° C.). It is the melting point of this recrystallised sample which is given in Table MI.

MI5 The product was characterised by converting a small sample into its oxalate salt, the melting point of this salt is given in the last column of Table MI.

MI6 The residue from the initial reaction was partitioned between ether and aqueous ammonia solution. Evaporation of the ether layer yielded a solid which was dissolved in propan- 2-ol (50 ml) and 48% aqueous hydrobromic acid solution (20 ml). Evaporation yielded a residue which was dried by azeotropic distillation with propan-2-ol, then dissolved in methanol, treated with charcoal and the resulting solid was triturated with propan-2 -ol and crystallised from ether. The product in the form of a hydrobromide salt was used without further purification.

TABLE MI

| Ex | OR₃ | R₄ | G | SM | a | b | c | d | e | Note | mp |
|---|---|---|---|---|---|---|---|---|---|---|---|
| MI1 | 7-OMe | 6-F | 4-chlorophenyl | RC1 | 5.8 | 2.6 | 4.6 | 50 | 2 | MI1 | 96–97 |
| MI2 | 7-OMe | 6-F | 4-bromophenyl | RC2 | 4.2 | 1.9 | 3 | 100 | 1 | MI2 | 97–98 |
| MI3 | 7-OMe | 6-OMe | 3-trifluoro-methylphenyl | RB6 | 11 | 4 | 7.1 | 100 | 16 | MI3 | 156–158 |
| MI4 | 7-OMe | 6-F | 2,4-dichloro-phenyl | RC3 | 3 | 1.2 | 2.2 | 50 | 2 | MI4 | 125–127 |
| MI5 | 8-OMe | 5-Cl | phenyl | RB22 | 10.5 | 5 | 8.9 | 100 | 1 | MI5 | 132–135 |
| MI6 | 7-OMe | 6-Ph | 2-chlorophenyl | RC22 | 7.5 | 2.3 | 5.1 | 215 | 4 | MI6 | ND |

EXAMPLES MF

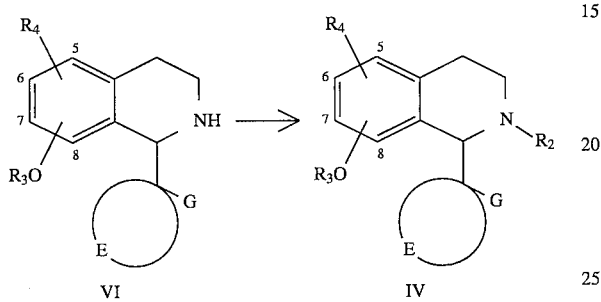

A mixture of a compound of formula VI in which OR₃, R₄ and G are as identified in Table MF and E is —(CH₂)₃— (a g), 37–40% aqueous formaldehyde solution (b ml), sodium cyanoborohydride (c g) and acetonitrile (d ml) was stirred for 15 minutes. Glacial acetic acid was added to neutralise the solution and stirring was continued for a further 45 minutes. The mixture was concentrated by evaporation and basified with 2N aqueous potassium hydroxide solution. The resulting mixture was extracted with ether and the ether extracts washed with aqueous potassium hydroxide solution. The product was extracted into aqueous hydrochloric acid. The acid extract was basified and extracted with ether. The ether extract yielded a residue which was a compound of formula IV in which OR₃, R₄ and G are as identified in Table MF, E is —(CH₂)₃— and R₂ is methyl.

NOTES TO TABLE MF

MF1 The residue was used without further treatment. Its melting point is given in the last column of Table MF.

MF2 The residue was characterised by converting a small sample into its hydrochloride salt. The melting point of this hydrochloride salt is given in the last column of Table MF.

MF3 The residue was converted into its hydrochloride salt which was recrystallised from propan-2-ol. The melting point of this salt is given in the last column of Table MF.

MF4 The product of Example RB5 was converted to its free base which was used as the starting material. The product in the form of its free base was obtained as a gum. The nmr spectrum was consistent with the required structure.

TABLE MF

| Ex | OR₃ | R₄ | G | SM | a | b | c | d | Note | mp |
|---|---|---|---|---|---|---|---|---|---|---|
| MF1 | 7-OMe | 6-OMe | 2-bromophenyl | RB1 | 3 | 2.9 | 0.74 | 90 | MF1 | 92–93 |
| MF2 | 7-OMe | 6-OMe | 2-chlorophenyl | RB2 | 7.2 | 7.92 | 2 | 160 | MF1 | 94–96 |
| MF3 | 7-OMe | 6-OMe | 4-fluorophenyl | RB3 | 7 | 8.2 | 2.1 | 165 | MF2 | 189–190 (dec) |
| MF4 | 7-OMe | 6-OMe | 2-methylphenyl | RB4 | 8.3 | 9.4 | 2.4 | 190 | MF3 | 195 (dec) |
| MF5 | 7-OMe | 6-OMe | 2-fluorophenyl | RB5 | 13.7 | 16 | 3 | 320 | MF4 | |

EXAMPLE MF6

A mixture of the oxalate salt of 1-[1-(2-chlorophenyl)cyclobutyl]-7-methoxy-6-methyl-1,2,3,4-tetrahydroisoquinoline (4.42 g prepared as described in Example RC12), methanol (87 ml) and 37–40% aqueous formaldehyde solution (5.1 ml) was cooled to 10° C. and sodium cyanoborohydride (2.64 g) was added. After 10 minutes the mixture was allowed to warm to ambient temperature and was stirred for 24 hours. The reaction mixture was concentrated and the residue partitioned between ethyl acetate and dilute aqueous sodium hydroxide solution. The organic phase was washed with aqueous ammonia solution, then dried and concentrated to yield 1-[1-(2-chlorophenyl)cyclobutyl]-7-methoxy-2,6

-dimethyl-1,2,3,4-tetrahydroisoquinoline (3.3 g).

EXAMPLE MF7

A mixture of 1-[1-(2-chlorophenyl)cyclopropyl]-7-methoxy-1,2,3,4-tetrahydroisoquinoline (2.5 g, prepared as described in Example RC10), 37–40% aqueous formaldehyde solution (2.9 ml), sodium cyanoborohydride (0.75 g) and acetonitrile (100 ml) was stirred for 15 minutes. Glacial acetic acid was added to neutralise the solution and stirring was continued for a further 45 minutes. The mixture was basified with aqueous sodium hydroxide solution, then extracted with ethyl acetate. The extracts yielded 1-[1-(2-chlorophenyl)cyclopropyl]-7-methoxy-2-methyl-1,2,3,4-tetrahydroisoquinoline.

EXAMPLES RB

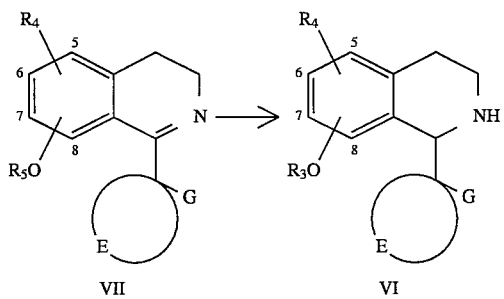

A compound of formula VII in which $OR_5$ is the group $OR_3$ as identified in Table RB and $R_4$, E and G are as identified in Table RB (a g) in methanol (b ml) was treated with sodium borohydride (c g) added portionwise with stirring. When thin layer chromatography showed that the reduction was substantially complete, the reaction mixture was concentrated, water was added and the resulting mixture extracted with the solvent shown in column d (a=ethyl acetate, b=ether or c= dichloromethane). The extracts were dried and the solvent removed by evaporation to give a residue which was treated as shown by the Notes to Table RB to give a compound of formula VI in which $OR_3$, $R_4$, E and G are as identified in Table RB.

NOTES TO TABLE RB

The abbreviation "OBz" represents benzyloxy. In column E of Table RB, W represents $-CH_2.CMe_2.CH_2-$.

RB1 The residue was recrystallised from an ethyl acetate/petroleum ether mixture to give the desired product as the free base, the melting point of which is given in the last column of Table RB.

RB2 The residue was characterised by converting a portion of it into its oxalate salt, the melting point of which is given in the last column of Table RB.

RB3 The residue was purified by hydrochloride salt formation. The melting point of this salt is given in the last column of Table RB.

RB4 The residue was used as the starting material for the next stage without being characterised.

RB5 The residue was characterised by converting a portion of it into its hydrochloride salt the melting point of which is given in the last column of Table RB.

RB6 The reaction mixture was filtered and the volume reduced to half. The desired product precipitated and was collected by filtration. The melting point is given in the last column of Table RB.

RB7 The residue was purified by flash chromatography to give the desired product which was used without being further characterised.

RB8 The product was recrystallised from petroleum ether (b.p. 60°–80° C.).

RB9 The residue from the reaction mixture was freed of trimethylborate by azeotropic distillation with methanol and partitioned between water and dichloromethane. The extract yielded the desired product which was used without further purification.

RB10 The desired product precipitated from the reaction mixture on cooling. The product was washed with methanol and air dried. Its melting point is given in Table RB.

RB11 Water was added to the reaction mixture and the desired product precipitated on cooling. Its melting point is given in Table RB.

RB12 The reaction mixture was acidified with 5N hydrochloric acid and the resulting solid collected by filtration. The solid was basified with aqueous sodium hydroxide solution and the resulting mixture extracted with ether. The ether extract yielded the desired product which was used without further purification.

TABLE RB

| Ex | $OR_3$ | $R_4$ | E | G | SM | a | b | c | d | Note | mp |
|---|---|---|---|---|---|---|---|---|---|---|---|
| RB1 | 7-OMe | 6-OMe | $(CH_2)_3$ | 2-bromo-phenyl | CA1 | 5.8 | 250 | 1.6 | (a) | RB1 | 112–114 |
| RB2 | 7-OMe | 6-OMe | $(CH_2)_3$ | 2-chloro-phenyl | CA2 | 8.7 | 300 | 2.9 | (a) | RB2 | 191 (dec) |
| RB3 | 7-OMe | 6-OMe | $(CH_2)_3$ | 4-fluoro-phenyl | CA3 | 7.9 | 30 | 2.6 | (a) | RB2 | 193–194 (dec) |
| RB4 | 7-OMe | 6-OMe | $(CH_2)_3$ | 2-methyl-phenyl | CA4 | 9.3 | 180 | 3.2 | (a) | RB5 | 227–228 |
| RB5 | 7-OMe | 6-OMe | $(CH_2)_3$ | 2-fluoro-phenyl | CA7 | 16 | 128 | 5.6 | (b) | RB3 | 251 (dec) |
| RB6 | 7-OMe | 6-OMe | $(CH_2)_3$ | 3-tri-fluoro-methyl-phenyl | CT1 | 15 | 100 | 1.5 | (c) | RB5 | 198–201 |
| RB7 | 7-OMe | 6-OMe | $(CH_2)_2$ | 4-chloro-phenyl | CT2 | 10 | 200 | 1.8 | | RB6 | 132–133 |

TABLE RB-continued

| Ex | OR₃ | R₄ | E | G | SM | a | b | c | d | Note | mp |
|---|---|---|---|---|---|---|---|---|---|---|---|
| RB8 | 7-OMe | 6-OMe | $(CH_2)_4$ | phenyl | CT4 | 3.4 | 75 | 0.8 | (c) | RB3 | 238–240 |
| RB9 | 7-OMe | 6-OMe | $(CH_2)_5$ | 4-chloro-phenyl | CT5 | 10.5 | 250 | 5 | (c) | RB7 | |
| RB10 | 7-OMe | 6-OMe | W | phenyl | CT8 | 28 | 200 | 3.7 | (c) | RB8 | 89–91 |
| RB11 | 7-OMe | 6-Br | $(CH_2)_3$ | phenyl | CA12 | 4.2 | 100 | 2 | (c) | RB4 | |
| RB12 | 7-OMe | 6-OMe | $(CH_2)_4$ | 4-methoxy phenyl | CT7 | 7.0 | 100 | 1 | (c) | RB3 | 208–212 |
| RB13 | 7-OMe | 6-OMe | $(CH_2)_3$ | 3,4-di-chloro-phenyl | CT6 | 10 | 200 | 4.8 | | RB10 | 101–103 |
| RB14 | 7-OMe | 6-F | $(CH_2)_3$ | phenyl | CA16 | 8.6 | 100 | 1.1 | (c) | RB4 | |
| RB15 | 5-OMe | H | $(CH_2)_3$ | 4-chloro-phenyl | CT9 | 4.3 | 75 | 0.5 | | RB4 | |
| RB16 | 7-OMe | 6-OMe | $(CH_2)_2$ | phenyl | CT10 | 2.1 | 30 | 0.35 | | RB11 | 97–99 |
| RB17 | 7-OMe | 6-OMe | $(CH_2)_4$ | 4-chloro-phenyl | CT3 | 4.2 | 100 | 2.85 | | RB9 | |
| RB18 | 7-OMe | 6-Cl | $(CH_2)_3$ | phenyl | CA9 | 5.8 | 100 | 0.7 | | RB9 | |
| RB19 | 7-OMe | 6-OMe | $(CH_2)_5$ | phenyl | CT11 | 11 | 500 | 22.5 | | RB9 | |
| RB20 | 7-OMe | 6-OMe | $(CH_2)_3$ | 2-naphthyl | CA17 | 6.2 | 25 | 1.9 | (a) | RB4 | |
| RB21 | 7-OMe | 6-Cl | W | phenyl | CA18 | 8 | 100 | 2.0 | (b) | RB5 | 240 (dec) |
| RB22 | 8-OMe | 5-Cl | $(CH_2)_3$ | phenyl | CA19 | 10 | 100 | 1.5 | | RB9 | |
| RB23 | 6-OMe | 7-Cl | $(CH_2)_3$ | phenyl | CT12 | 23.6 | 400 | 17 | | RB12 | |
| RB24 | 7-OMe | 5-Cl 6-OMe | $(CH_2)_3$ | phenyl | CT14 | 10.5 | 150 | 1.5 | | RB9 | |
| RB25 | 7-OBz | 6-OMe | $(CH_2)_3$ | 2-chloro-phenyl | CA27 | 5 | 30 | 1.8 | (c) | RB4 | |
| RB26 | 7-OBz | 6-OMe | $(CH_2)_5$ | phenyl | CA33 | 5.5 | 50 | 4 | | RB9 | |

EXAMPLES RC

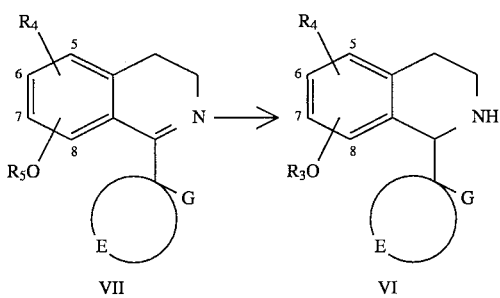

A solution of a compound of formula VII in which $OR_5$ is the group $OR_3$ as identified in Table RC and $R_4$, E and G are as identified in Table RC (a g, prepared as described in the Example identified in column SM of Table RC) in glacial acetic acid (b ml) and methanol (c ml) at 0° C. was treated with sodium cyanoborohydride (d g). The mixture was stirred at ambient temperature for e hours to give a compound of formula VI in which $OR_3$, $R_4$, E and G are as identified in Table RC. The reaction mixture was then treated as described in the Notes to Table RC.

NOTES TO TABLE RC

The abbreviation "OBz" represents benzyloxy and W represents —$CH_2CMe_2CH_2$—.

RC1 The volume of the reaction mixture was reduced by evaporation and the residue partitioned between water and dichloromethane. The organic layer was washed with concentrated aqueous ammonia solution and brine and then dried. Removal of the solvent gave a residue which was used without further purification.

RC2 The reaction mixture was poured into water and the resulting mixture extracted with dichloromethane. The extract was washed with brine and dried. Removal of the solvent gave a solid which was triturated with petroleum ether (bp 60°–80° C.), recrystallised from ethanol and then dissolved in dichloromethane. The solution was washed with concentrated aqueous ammonia solution and dried. Removal of the solvent gave the desired product.

RC3 The volume of the reaction mixture was reduced by evaporation and the residue partitioned between water and dichloromethane. The organic layer was washed with concentrated aqueous ammonia solution and brine and then dried. Removal of the solvent gave a residue which was triturated with a mixture of light petroleum ether and ether to give the desired product, the melting point of which was 100°–102° C.

RC4 The volume of the reaction mixture was reduced by evaporation and the residue partitioned between water and dichloromethane. The organic layer was washed with concentrated aqueous ammonia solution and brine, dried, decolourised and then the solvent was removed to give a syrup which crystallised on standing. The product was washed with ether and dried (mp 109°–111° C.).

RC5 The reaction mixture was diluted with dichloromethane and the resulting organic layer was washed with concentrated aqueous ammonia solution and dried. Evaporation yielded the desired product as a syrup which was used in the next stage without further purification.

RC6 The reaction mixture was poured into water and extracted with dichloromethane. The organic layer was washed with concentrated aqueous ammonia solution and brine and then dried. The dried organic layer yielded the desired product on evaporation which was used in the next stage without further purification.

RC7 Water was added to the reaction mixture and the mixture basified with aqueous ammonia solution and extracted with ether. The extract yielded the desired product which was used without further purification.

RC8 The reaction mixture was added to ice/water, basified with aqueous ammonia solution and extracted with ether.

Ethereal oxalic acid solvent was added to give the desired product as an oxalate salt which was dried at 55° C. in vacuo.

RC9 After 24 hours unreacted starting material was detected. A further portion of sodium cyanoborohydride (0.2 g) was added and the mixture stirred for 2 hours. The reaction mixture was partitioned between dichloromethane and water. The organic layer was washed with concentrated aqueous ammonia solution and yielded the desired product which was used without further purification.

RC10 After 24 hours unreacted starting material was detected. A further portion of sodium cyanoborohydride (0.2 g) was added and the mixture stirred for 24 hours. The reaction mixture was partitioned between dichloromethane and concentrated aqueous ammonia solution. The organic layer yielded the desired product which was used without further purification.

RC11 The reaction mixture was initially stirred at 0°–5° C. for 2 hours and then stirred at ambient temperature for 24 hours. The reaction mixture was poured onto a mixture of ice and water, basified by the addition of concentrated aqueous ammonia solution and extracted with dichloromethane. The extract yielded the desired product which was used without further purification.

RC12 The reaction mixture was poured into water, basified with aqueous ammonia solution and extracted with ethyl acetate. The extract yielded a gum which was dissolved in ether and treated with ethereal oxalic acid to give the desired product as an oxalate salt which was dried in vacuo.

RC13 The reaction mixture was poured into aqueous ammonia solution and extracted with ethyl acetate. The extracts were washed with aqueous ammonia solution and brine, then dried and concentrated to give the desired product which was used without further purification.

RC14 The volume of the reaction mixture was reduced by evaporation and the residue partitioned between dichloromethane and concentrated aqueous ammonia solution. The organic layer was dried, filtered and evaporated in vacuo to yield an oil which was dissolved in propan-2-ol and treated with 48% aqueous hydrobromic acid. Evaporation yielded a solid hydrobromide salt which was recrystallised from ether.

RC15 The reaction mixture was initially stirred at 0°–5° C. for 2 hours and then stirred at ambient temperature for 24 hours. The reaction mixture was poured onto a mixture of ice and water, basified by the addition of concentrated aqueous ammonia solution and extracted with dichloromethane. The extracts yielded a residue which was dissolved in propan-2-ol (50 ml). 48% Aqueous hydrobromic acid (25 ml) was added. The mixture was dried by azeotropic distillation with propan-2-ol and crystallised from ether to give the desired product as a hydrobromide salt (m.p. 227°–233° C.).

RC16 The reaction mixture was treated in a manner similar to that described in Note RC6, but the product was then dissolved in propan-2-ol and treated with 48% aqueous hydrobromic acid solution. The solution was cooled and scratched to yield a solid which was filtered and dried to yield the hydrobromide salt.

RC17 The reaction mixture was poured onto water and extracted with dichloromethane. The organic layer was washed with dilute aqueous ammonia solution, then with water, then was dried over magnesium sulphate, filtered and concentrated in vacuo. The residue was dissolved in ether and hydrogen chloride was bubbled through. The resulting precipitate was collected by filtration, washed with ether and dried in vacuo, yielding the desired product as a hydrochloride salt.

TABLE RC

| Ex | $OR_3$ | $R_4$ | E | G | SM | a | b | c | d | e | Notes |
|---|---|---|---|---|---|---|---|---|---|---|---|
| RC1 | 7-OMe | 6-F | $(CH_2)_3$ | 4-chlorophenyl | CA5 | 6 | 50 | 25 | 2.2 | 24 | RC1 |
| RC2 | 7-OMe | 6-F | $(CH_2)_3$ | 4-bromophenyl | CA6 | 8.3 | 50 | 25 | 2.7 | 16 | RC2 |
| RC3 | 7-OMe | 6-F | $(CH_2)_3$ | 2,4-dichlorophenyl | CA8 | 4.8 | 40 | 20 | 1.6 | 24 | RC3 |
| RC4 | 7-OMe | 6-F | $(CH_2)_2$ | 2,4-dichlorophenyl | CQ | 9.7 | 100 | 50 | 3.4 | 16 | RC16 |
| RC5 | 7-OMe | 6-OMe | $(CH_2)_3$ | 4-bromophenyl | CA10 | 13 | 100 | 50 | 4.1 | 72 | RC4 |
| RC6 | 7-OMe | 6-Cl | $(CH_2)_3$ | 2-chlorophenyl | CA13 | 4.3 | 30 | 15 | 1.5 | 24 | RC5 |
| RC7 | 7-OMe | 6-OMe | $(CH_2)_3$ | 2-trifluoromethylphenyl | CA14 | 5 | 40 | 20 | 3.2 | 16 | RC6 |
| RC8 | 7-OMe | 6-F | $(CH_2)_3$ | 2-chlorophenyl | CA15 | 9.4 | 50 | 25 | 3.4 | 20 | RC6 |
| RC9 | 7-OMe | 6-OMe | $(CH_2)_3$ | 2,4-dichlorophenyl | CA21 | 4 | 28 | 14 | 2 | 2 | RC7 |
| RC10 | 7-OMe | H | $(CH_2)_2$ | 2-chlorophenyl | CP | 2.4 | 20 | 10 | 0.9 | 16 | RC13 |
| RC11 | 7-OMe | H | $(CH_2)_3$ | 2-chlorophenyl | CA22 | 5.2 | 42 | 21 | 2.4 | 3 | RC8 |
| RC12 | 7-OMe | 6-Me | $(CH_2)_3$ | 2-chlorophenyl | CA23 | 5.78 | 55 | 27.5 | 2.1 | 1 | RC12 |
| RC13 | 7-OBz | 6-OMe | $(CH_2)_3$ | 2,4-dichlorophenyl | CA30 | 4.4 | 20 | 10 | 1.2 | 24 | RC9 |
| RC14 | 7-OBz | 6-OMe | $(CH_2)_2$ | 2-chlorophenyl | CA28 | 6.3 | 40 | 20 | 1.9 | 24 | RC14 |

TABLE RC-continued

| Ex | OR₃ | R₄ | E | G | SM | a | b | c | d | e | Notes |
|---|---|---|---|---|---|---|---|---|---|---|---|
| RC15 | 7-OBz | 6-OMe | (CH₂)₂ | 1-naphthyl | CA29 | 11 | 64 | 32 | 3.2 | 120 | RC7 |
| RC16 | 7-OBz | 6-OMe | (CH₂)₃ | 2-methoxyphenyl | CA25 | 6 | 40 | 20 | 1.8 | 24 | RC10 |
| RC17 | 7-OBz | 6-OMe | (CH₂)₃ | 3-methoxyphenyl | CA26 | 6.65 | 50 | 25 | 2.65 |  | RC11 |
| RC18 | 7-OBz | 6-OMe | (CH₂)₃ | 4-trifluoromethoxyphenyl | CA31 | 4.1 | 30 | 15 | 1.1 | 1 | RC13 |
| RC19 | 7-OMe | 6-F | (CH₂)₃ | 2-bromophenyl | CA35 | 5 | 30 | 15 | 1.7 | 16 | RC6 |
| RC20 | 7-OMe | 6-OMe | (CH₂)₃ | 4-biphenylyl | CA11 | 4.7 | 30 | 15 | 1.49 | 24 | RC17 |
| RC21 | 7-OMe | 6-OMe | (CH₂)₃ | 3-chlorophenyl | CA24 | 8.6 | 50 | 25 | 3.5 | 5 | RC7 |
| RC22 | 7-OMe | 6-Ph | (CH₂)₃ | 2-chlorophenyl | CA37 | 7.8 | 53 | 26 | 2.94 | 2 | RC15 |
| RC23 | 7-OBz | 6-OMe | W | 2-chlorophenyl | CA36 | 9.2 | 100 | 50 | 2.6 | 16 | RC6 |

EXAMPLES CA

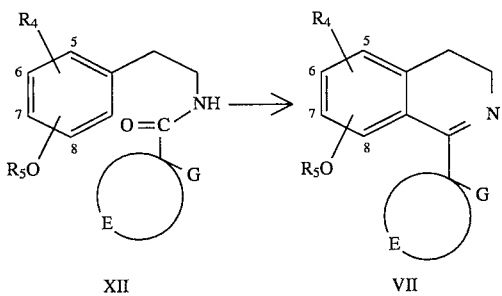

A mixture of a compound of formula XII in which $OR_5$, $R_4$, E and G are as identified in Table CA (a g, prepared as described in the Example identified in column SM of Table CA), phosphorus oxychloride (b ml) and acetonitrile (c ml) was heated under reflux. After heating for d hours the mixture was basified with aqueous ammonia solution and extracted with the solvent identified in column f of Table CA (a=ethyl acetate, b=dichloromethane, c=ether). The extract yielded a residue which was treated as described in the Notes to Table CA to give a compound of formula VII in which $OR_5$, $R_4$, E and G are as identified in Table CA.

NOTES TO TABLE CA

The abbreviation "OBz" represents benzyloxy. In column E of Table CA, W represents —CH₂.CMe₂.CH₂—.

CA1 The residue was used as the starting material for the next stage without further purification. The melting point of the residue is given in the last column of Table CA.

CA2 The residue was recrystallised from petroleum ether (b.p. 60°–80° C.) to give the desired product, the melting point of which is given in the last column of Table CA.

CA3 The residue was recrystallised from propan-2-ol to give the desired product, the melting point of which is given in the last column of Table CA.

CA4 The residue was used without being characterised.

CA5 The residue was treated with a 2:1 mixture of propan-2-ol and ether to yield the product as a pale yellow solid, the melting point of which is given in the last column of Table CA.

CA6 The reaction mixture was poured into ice/water, basified with aqueous sodium hydroxide solution and extracted with ether. The extract yielded a residue was taken up in a hot mixture of ether and cyclohexane. A solid precipitated on cooling which was recrystallised from propan-2-ol to give the desired product, the melting point of which is given in the last column of Table CA.

CA7 The residue was treated with cold propan-2-ol. The desired product was collected by filtration. The melting point is given in the last column of Table CA.

CA8 The residue was crystallised from methanol. The melting point of the desired product is given in the last column of Table CA.

CA9 The residue was treated with ether and the resulting mixture filtered. The desired product was obtained from the filtrate and used without further purification.

CA10 The residue was triturated with petroleum ether (b.p. 40°–60° C.) to give the desired product, the melting point of which is given in the last column of Table CA.

CA11 The residue was treated with acetonitrile. A solid was separated by filtration and the filtrate concentrated to give a gum which was purified by flash chromatography. A sample of the resulting product was recrystallised from propan-2-ol to give the desired product, the melting point of which is given in Table CA.

CA12 The residue was triturated with petroleum ether (b.p. 60°–80° C.) to give the desired product, the melting point of which is given in the last column of Table CA.

CA13 The residue was triturated with petroleum ether (b.p. 60°–80° C.) and recrystallised from propan-2-ol.

CA14 The residue was purified by flash chromatography to yield the solid product, the melting point of which is given in Table CA.

CA15 The residue was extracted with boiling petroleum ether (b.p. 60°–80° C.). The extract gave a residue which was recrystallised from propan-2-ol to give the desired product, the melting point of which is given in the last column of Table CA.

CA16 The residue was treated with a 1:3 mixture of ether and propan-2-ol to give the desired product as a solid, the melting point of which is given in Table CA.

CA17 The residue was crystallised from ethanol. A sample (1 g) was recrystallised from ethanol to give a solid, the melting point of which is given in the last column of Table CA.

CA18 The extract was washed with dilute aqueous hydrochloric acid. The washings were basified and extracted with ethyl acetate. The extract yielded the desired product which was used without further purification.

CA19 The extract was washed with brine, dried over magnesium sulphate, decolourised with charcoal, filtered and the solvent removed by evaporation to yield a solid. The solid was recrystallised from propan-2-ol to yield 7-benzyloxy-6-methoxy-[1-(2-methylthiophenyl)cyclobutyl]dihydroisoquinoline.

CA20 After heating for 2 hours, the reaction mixture was poured onto ice/water and basified with concentrated aqueous ammonia solution. The basic solution was extracted with ethyl acetate and the extracts washed with brine, dried over magnesium sulphate and filtered. The solvent was removed in vacuo to yield a gum which was used without further purification.

CA21 After heating for d hours, the solvent was removed in vacuo and the residue dissolved in ethyl acetate. A slight excess of aqueous ammonia solution was added. The organic layer yielded a gum which was used without further purification.

CA22 The extract was washed with dilute aqueous sodium hydroxide solution and brine. The extract yielded a residue which was used without further purification.

TABLE CA

| Ex | $OR_5$ | $R_4$ | E | G | SM | a | b | c | d | f | Note | mp |
|---|---|---|---|---|---|---|---|---|---|---|---|---|
| CA1 | 7-OMe | 6-OMe | $(CH_2)_3$ | 2-bromophenyl | D1 | 7.7 | 11.3 | 80 | 2.5 | (a) | CA1 | 125–127 |
| CA2 | 7-OMe | 6-OMe | $(CH_2)_3$ | 2-chlorophenyl | D2 | 12 | 20 | 200 | 2.5 | (b) | CA1 | 135–138 |
| CA3 | 7-OMe | 6-OMe | $(CH_2)_3$ | 4-fluorophenyl | D3 | 12 | 21 | 145 | 2.5 | (a) | CA1 | 100–101 |
| CA4 | 7-OMe | 6-OMe | $(CH_2)_3$ | 2-methylphenyl | D4 | 15.1 | 26.5 | 185 | 2.5 | (a) | CA2 | 105–106 |
| CA5 | 7-OMe | 6-F | $(CH_2)_3$ | 4-chlorophenyl | E1 | 16 | 13 | 150 | 40 | (a) | CA3 | 84–86 |
| CA6 | 7-OMe | 6-F | $(CH_2)_3$ | 4-bromophenyl | E2 | 9.5 | 6.5 | 100 | 48 | (a) | CA4 | |
| CA7 | 7-OMe | 6-OMe | $(CH_2)_3$ | 2-fluorophenyl | D5 | 25 | 43.7 | 300 | 2.5 | (a) | CA1 | 104–106 |
| CA8 | 7-OMe | 6-F | $(CH_2)_3$ | 2,4-dichlorophenyl | E5 | 8.3 | 6 | 75 | 40 | (a) | CA3 | 117–119 |
| CA9 | 7-OMe | 6-Cl | $(CH_2)_3$ | phenyl | E6 | 64.3 | 52 | 300 | 48 | (a) | CA5 | 97–99 |
| CA10 | 7-OMe | 6-OMe | $(CH_2)_3$ | 4-bromophenyl | E11 | 17.5 | 8 | 100 | 20 | (a) | CA4 | |
| CA11 | 7-OMe | 6-OMe | $(CH_2)_3$ | 4-biphenylyl | E39 | 12.5 | 8.5 | 100 | 18 | (a) | CA20 | |
| CA12 | 7-OMe | 6-Br | $(CH_2)_3$ | phenyl | E14 | 10 | 50 | 100 | 42 | | CA6 | 119–120 |
| CA13 | 7-OMe | 6-Cl | $(CH_2)_3$ | 2-chlorophenyl | E16 | 18 | 13 | 100 | 48 | (a) | CA7 | 141–143 |
| CA14 | 7-OMe | 6-OMe | $(CH_2)_3$ | 2-trifluoromethylphenyl | E17 | 15 | 10.5 | 150 | 40 | (a) | CA3 | 141–143 |
| CA15 | 7-OMe | 6-F | $(CH_2)_3$ | 2-chlorophenyl | E18 | 24 | 18.5 | 150 | 36 | (a) | CA3 | 125–127 |
| CA16 | 7-OMe | 6-F | $(CH_2)_3$ | phenyl | E19 | 18 | 15.5 | 150 | 36 | (a) | CA4 | |
| CA17 | 7-OMe | 6-OMe | $(CH_2)_3$ | 2-naphthyl | E23 | 6 | 9.5 | 65 | 2.5 | (a) | CA8 | 128–129 |
| CA18 | 7-OMe | 6-Cl | W | phenyl | E24 | 15 | 7.9 | 100 | 24 | (c) | CA9 | |
| CA19 | 8-OMe | 5-Cl | $(CH_2)_3$ | phenyl | E27 | 20.6 | 16.8 | 150 | 5 | (a) | CA10 | 129–132 |
| CA20 | 7-OMe | 6-Cl | $(CH_2)_3$ | 2-bromophenyl | D6 | 10.5 | 15.1 | 250 | 48 | (a) | CA11 | |
| CA21 | 7-OMe | 6-OMe | $(CH_2)_3$ | 2,4-dichlorophenyl | E28 | 12.7 | 11 | 50 | 8 | (a) | CA12 | 115–117 |
| CA22 | 7-OMe | H | $(CH_2)_3$ | 2-chlorophenyl | E29 | 34.2 | 29 | 200 | 23 | (c) | CA4 | |
| CA23 | 7-OMe | 6-Me | $(CH_2)_3$ | 2-chlorophenyl | D7 | 19 | 30.8 | 185 | 5 | (a) | CA17 | 126–128 |
| CA24 | 7-OMe | 6-OMe | $(CH_2)_3$ | 3-chlorophenyl | E31 | 12.9 | 11 | 50 | 24 | (c) | CA13 | 103–104 |
| CA25 | 7-OBz | 6-OMe | $(CH_2)_3$ | 2-methoxyphenyl | E33 | 16.2 | 10 | 100 | 2 | (a) | CA14 | 107–108 |
| CA26 | 7-OBz | 6-OMe | $(CH_2)_3$ | 3-methoxyphenyl | E34 | 17 | 20 | 150 | 5 | (b) | CA15 | 107–109 |
| CA27 | 7-OBz | 6-OMe | $(CH_2)_3$ | 2-chlorophenyl | E36 | 21 | 25 | 150 | 6 | (a) | CA14 | 112–114 |
| CA28 | 7-OBz | 6-OMe | $(CH_2)_2$ | 2-chloro- | E35 | 15.5 | 10 | 75 | 18 | (a) | CA17 | 121–123 |

TABLE CA-continued

| Ex | OR$_5$ | R$_4$ | E | G | SM | a | b | c | d | f | Note | mp |
|---|---|---|---|---|---|---|---|---|---|---|---|---|
| CA29 | 7-OBz | 6-OMe | (CH$_2$)$_2$ | phenyl 1-naphthyl | E45 | 14.1 | 25 | 200 | 1.5 | (a) | CA21 | ND |
| CA30 | 7-OBz | 6-OMe | (CH$_2$)$_3$ | 2,4-dichlorophenyl | E37 | 23 | 13.5 | 150 | 4 | (a) | CA16 | 118–119 |
| CA31 | 7-OBz | 6-OMe | (CH$_2$)$_3$ | 4-trifluoromethoxyphenyl | D9 | 7.9 | 9.2 | 55 | 5 | (a) | CA1 | 158–161 |
| CA32 | 7-OBz | 6-OMe | (CH$_2$)$_3$ | 2-methylthio phenyl | E38 | 4.7 | 3 | 30 | 3 | (a) | CA19 | ND |
| CA33 | 7-OBz | 6-OMe | (CH$_2$)$_5$ | phenyl | E40 | 26.7 | 17 | 100 | 2.5 | (a) | CA14 | 96–98 |
| CA34 | 7-OBz | 6-OMe | (CH$_2$)$_4$ | 2-chlorophenyl | E41 | 12.7 | 7.7 | 100 | 16 | (a) | CA4 | ND |
| CA35 | 7-OMe | 6-F | (CH$_2$)$_3$ | 2-bromophenyl | E42 | 10 | 7 | 100 | 48 | (a) | CA3 | 129–130 |
| CA36 | 7-OBz | 6-OMe | W | 2-chlorophenyl | E43 | 14.6 | 8.5 | 100 | 20 | (a) | CA22 | ND |

EXAMPLE CA37

A mixture of N-[2-(2-methoxy-5-biphenylyl)ethyl] -1-(2-chlorophenyl)cyclobutane carboxamide (12.5 g, prepared as described in Example E30), phosphorus oxychloride (25 ml) and acetonitrile (150 ml) was heated under reflux for 6 hours. The solvent was removed by distillation and the residue added to a mixture of ice and water. The mixture was extracted with dichloromethane to yield a solid which was recrystallised from propan-2-ol to give 1-[1-(2-chlorophenyl)cyclobutyl] -7-methoxy-6-phenyl-3,4-dihydroisoquinoline, m.p. 149°–152° C.

EXAMPLE CP

A mixture of N-[2-(4-methoxyphenyl)ethyl]-1-(2-chlorophenyl)cyclopropanecarboxamide (2 g, prepared in a similar manner to that described in Example D8) and polyphosphate ester (20 ml) was gently heated for 12 hours. The mixture was poured into water and washed with ether, then ethyl acetate. The aqueous phase was basified with aqueous ammonia solution and extracted with ethyl acetate. The extract yielded a solid which was recrystallised from cyclohexane to give 1-[1-(2-chlorophenyl)cyclopropyl] -7-methoxy-3,4-dihydroisoquinoline.

EXAMPLE CO

A mixture of N-[2-(3-fluoro-4-methoxyphenyl)ethyl] -1-(2,4-dichlorophenyl)cyclopropanecarboxamide (19.7 g, prepared in a similar manner to that described in Example E4), 52% polyphosphate ester in chloroform (200 g) was heated under reflux for 52 hours, then cooled and poured onto ice. The organic layer was separated, the aqueous layer extracted with dichloromethane and the combined organic layers were basified by addition of aqueous ammonia solution, washed with brine, dried over magnesium sulphate and filtered. The solvent was removed in vacuo to yield a solid which was triturated with petroleum ether (b.p. 40°–60° C.) and propan-2-ol. The solid was collected by filtration and dried to yield 1-[1-(2,4-dichlorophenyl)cyclopropyl]-6-fluoro-7-methoxy-3,4-dihydroisoquinoline (10.3 g), m.p. 151°–154° C.

EXAMPLES CT

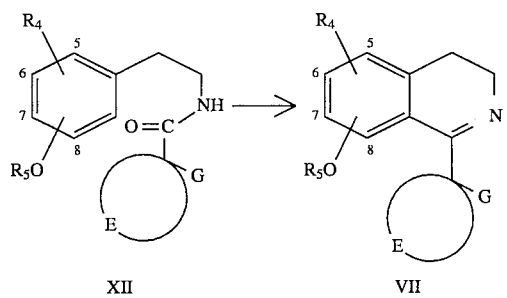

A mixture of a compound of formula XII in which OR$_5$, R$_4$, E and G are as identified in Table CT (a g, prepared as described in the Example identified in column SM of Table CT), phosphorus oxychloride (b ml) and toluene (c ml) was heated on a steam bath for d hours. The mixture was poured into ice/water, basified with concentrated aqueous ammonia solution and extracted with the solvent identified in column e of Table CT (a= ethyl acetate, b=ether). The extract yielded a residue which was treated as described in the Notes to Table CT to give a compound of formula VII in which OR$_5$, R$_4$, E and G are as identified in Table CT.

NOTES TO TABLE CT

The abbreviation "OBz" represents benzyloxy. In column E of Table CT, W represents —CH$_2$.CMe$_2$.CH$_2$—.

CT1 The residue was treated with a mixture of ether and petroleum ether. The resulting solid was collected by filtration. Its melting point is given in the last column of Table CT.

CT2 The residue was crystallised from a 4:1:2 mixture of ether, ethyl acetate and petroleum ether to give the desired product, the melting point is given in the last column of Table CT.

CT3 The residue was used in the next stage without further purification. The melting point is given in the last column of Table CT.

CT4 The toluene was removed from the reaction mixture by evaporation and the residue poured into ice/water. The solution was basified with aqueous ammonia solution and extracted with ether. The extract yielded the desired product, the melting point of which is given in the last column of Table CT.

CT5 The residue was crystallised from ether to give the desired product. The melting point is given in the last column of Table CT.

CT6 The residue was crystallised from a mixture of ether and petroleum ether. The resulting solid was collected by filtration. Its melting point is given in the last column of Table CT.

CT7 The residue was used in the next stage without further purification.

CT8 The residue was purified by flash chromatography to give the desired product. The melting point is given in the last column of Table CT.

CT9 The residue was treated with a mixture of ether and petroleum ether. The resulting solid was collected by filtration. The product was used without further treatment.

CT10 The residue was taken up in ether and the solution dried. An ethereal solution of oxalic acid was added to give the oxalate salt which was washed with ether and partitioned between aqueous ammonia solution and ether. The ether layer gave the desired product in the form of its free base as an oil which was used without further purification.

CT11 The residue was taken up in ether and an ethereal solution of oxalic acid added to give the oxalate salt which was washed with ether, basified with 30% aqueous potassium hydroxide solution and extracted with ether. The extract yielded an oil which was used without further purification.

TABLE CT

| Ex | OR$_5$ | R$_4$ | E | G | SM | a | b | c | d | e | Note | mp |
|---|---|---|---|---|---|---|---|---|---|---|---|---|
| CT1 | 7-OMe | 6-OMe | (CH$_2$)$_3$ | 3-trifluoromethyl phenyl | E3 | 35 | 23.8 | 200 | 16 | (a) | CT1 | 98–100 |
| CT2 | 7-OMe | 6-OMe | (CH$_2$)$_2$ | 4-chloro phenyl | E7 | 30 | 16.6 | 200 | 8 | (b) | CT2 | 91–92 |
| CT3 | 7-OMe | 6-OMe | (CH$_2$)$_4$ | 4-chloro phenyl | E8 | 34 | 23.8 | 200 | 8 | (b) | CT3 | 106–107 |
| CT4 | 7-OMe | 6-OMe | (CH$_2$)$_4$ | phenyl | E9 | 36 | 27.9 | 200 | 1 | | CT4 | 112–114 |
| CT5 | 7-OMe | 6-OMe | (CH$_2$)$_5$ | 4-chloro phenyl | E10 | 17 | 11.3 | 100 | 8 | (b) | CT5 | 135–136 |
| CT6 | 7-OMe | 6-OMe | (CH$_2$)$_3$ | 3,4-dichloro phenyl | E12 | 39 | 26.1 | 200 | 8 | (b) | CT6 | 111–112 |
| CT7 | 7-OMe | 6-OMe | (CH$_2$)$_4$ | 4-methoxy phenyl | E13 | 14 | 9.5 | 100 | 2 | (b) | CT5 | 88–89 |
| CT8 | 7-OMe | 6-OMe | W | phenyl | E15 | 30 | 14.9 | 200 | 6 | (a) | CT7 | |
| CT9 | 5-OMe | H | (CH$_2$)$_3$ | 4-chloro phenyl | E20 | 13 | 35 | 100 | 30 | (a) | CT8 | 111–112 |
| CT10 | 7-OMe | 6-OMe | (CH$_2$)$_2$ | phenyl | E21 | 26 | 22 | 100 | 1 | (a) | CT3 | 141–144 |
| CT11 | 7-OMe | 6-OMe | (CH$_2$)$_5$ | phenyl | E22 | 29 | 14.8 | 200 | 20 | (a) | CT9 | |
| CT12 | 6-OMe | 7-Cl | (CH$_2$)$_3$ | phenyl | E25 | 25.7 | 207 | 300 | 5 | (b) | CT7 | |
| CT13 | 7-OMe | H | (CH$_2$)$_3$ | phenyl | E44 | 24 | 22 | 200 | 72 | (b) | CT10 | |
| CT14 | 7-OMe | 5-Cl 6-OMe | (CH$_2$)$_3$ | phenyl | E26 | 12.5 | 9.6 | 75 | 2.5 | (a) | CT7 | |
| CT15 | 7-OBz | 6-OMe | (CH$_2$)$_3$ | phenyl | E32 | 32.9 | 22 | 200 | 3.5 | (b) | CT11 | |

EXAMPLES D

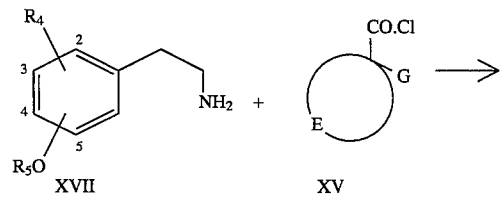

XVII    XV

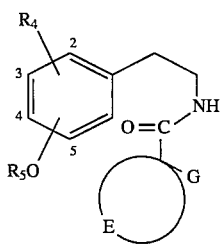

XII

A 1-arylcycloalkanecarbonyl chloride of formula XV in which E and G are as identified in Table D, (a g prepared as described in the Example identified in column SM of Table D) was added dropwise at 0° C. to a stirred solution of a phenethylamine of formula XVII in which $OR_5$ and $R_4$ are as identified in Table D, (b g) and triethylamine (c ml) in ether (d ml) to form a compound of formula XII. After 16 hours the reaction mixture was poured into water and extracted with the solvent identified in column e of Table D (a=ethyl acetate, b=ether, c=dichloromethane). The extract yielded a residue which was treated as described in the Notes (Nb) to Table D.

NOTES (Nb) TO TABLE D

D1 The residue was used without further purification Its melting point is given in the last column of Table D.

D2 The residue was washed with petroleum ether (b.p 60°–80° C.). Its melting point is given in the last column of Table D.

D3 The residue was a glass, the melting point of which was not determined.

D4 The ether in the reaction mixture was replaced by dichloromethane and the reaction mixture poured into water and acidified with concentrated hydrochloric acid. Evaporation of the dichloromethane layer gave a residue which was washed with ethanol and dried in vacuo. It was used without further purification. Its melting point is given in Table D.

D5 The reaction mixture was stirred for two days and then poured into water. The mixture was basified, stirred for 30 minutes, acidified, washed with ether, basified and extracted with ethyl acetate. The extract yielded the desired product which was used without further purification.

EXAMPLES E

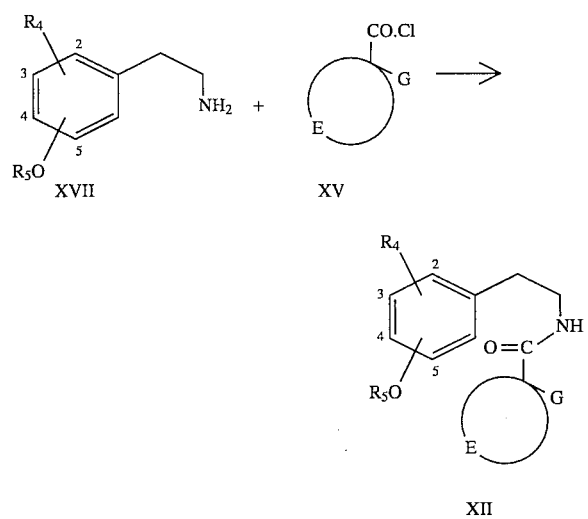

A solution of a 1-arylcycloalkane carbonyl chloride of formula XV in which E and G are as identified in Table E (a g prepared as described in the Example identified in column SM of Table E) in ether (b ml) was added dropwise to a stirred solution of a phenethylamine of formula XVII in which $OR_5$ and $R_4$ are as identified in Table E (c g) and triethylamine (d ml) in ether (e ml) to form a compound of formula XII. When the reaction was complete water was added and the product was isolated and treated as described in the Notes to Table E.

TABLE D

| Ex | $OR_5$ | $R_4$ | E | G | SM | a | b | c | d | e | Nb | mp |
|---|---|---|---|---|---|---|---|---|---|---|---|---|
| D1 | 4-OMe | 3-OMe | $(CH_2)_3$ | 2-bromo-phenyl | CL1 | 5.5 | 3.3 | 2.8 | 150 | a | D1 | 111–112 |
| D2 | 4-OMe | 3-OMe | $(CH_2)_3$ | 2-chloro-phenyl | CL2 | 9 | 6.5 | 5.5 | 150 | b | D1 | 119–120 |
| D3 | 4-OMe | 3-OMe | $(CH_2)_3$ | 4-fluoro-phenyl | CL3 | 15 | 11.6 | 9.8 | 150 | b | D2 | 83–84 |
| D4 | 4-OMe | 3-OMe | $(CH_2)_3$ | 2-methyl-phenyl | CL4 | 11 | 8.7 | 7.4 | 150 | a | D3 | |
| D5 | 4-OMe | 3-OMe | $(CH_2)_3$ | 2-fluoro-phenyl | CL5 | 16 | 15 | 11.6 | 250 | a | D1 | 119–120 |
| D6 | 4-OMe | 3-Cl | $(CH_2)_3$ | 2-bromo-phenyl | CL1 | 11 | 7.2 | 5.6 | 120 | c | D4 | 116–119 |
| D7 | 4-OMe | 3-Me | $(CH_2)_3$ | 2-chloro-phenyl | CL2 | 12.4 | 9.45 | 10.96 | 140 | a | D5 | ND |
| D8 | 4-OMe | H | $(CH_2)_2$ | 2-chloro-phenyl | CL11 | 10 | 7 | 7.2 | 130 | b | D2 | 84–85 |
| D9 | 4-OBz | 3-OMe | $(CH_2)_3$ | 4-tri-fluoro methoxy phenyl | CL20 | 5.26 | 5.55 | 5.8 | 50 | b | D1 | ND |

NOTES TO TABLE E

The abbreviation "OBz" represents benzyloxy. In column E of Table E, W represents —$CH_2.CMe_2.CH_2$—.

E1 The residue obtained by evaporation of the organic layer of the reaction mixture was triturated with petroleum ether and then used as the starting material for the next stage without further purification.

E2 The residue obtained by evaporation of the organic layer of the reaction mixture was used without further purification.

E3 The residue obtained by evaporation of the organic layer of the reaction mixture was recrystallised from propan-2-ol.

E4 The residue obtained by evaporation of the organic layer of the reaction mixture was treated with a mixture of ether and petroleum ether and collected by filtration. The melting point is given in the last column of Table E.

E5 The solution of the phenethylamine was added to the solution of the carbonyl chloride. The reaction mixture gave a precipitate which was collected by filtration, washed with ether and water and dried in vacuo to give the desired product.

E6 The solution of the phenethylamine was added to the solution of the carbonyl chloride. The product was isolated from the organic phase and used without further purification.

E7 The melting point of the product is given in the last column of Table E.

E8 The residue obtained by evaporation of the organic layer of the reaction mixture was triturated with petroleum ether to give the desired product the melting point of which is given in the last column of Table E.

E9 The solution of the phenethylamine was added to the solution of the carbonyl chloride. The product was isolated from the organic phase and its melting point is given is the last column of Table E.

E10 The reaction was conducted under nitrogen. After the addition of the water, the reaction mixture was extracted with ethyl acetate and the desired product isolated from the organic layer and recrystallised from a mixture of ethyl acetate and petroleum ether. Its melting point is given in the last column of Table E.

E11 The product precipitated after the addition of the water and was collected, washed with water and dried in vacuo. Its melting point is given in the last column of Table E.

E12 The preparation of the phenethylamine starting material is given in Example P.

E13 After the addition of the water the reaction mixture was extracted with ethyl acetate and the desired product isolated from the organic layer and was used without further purification.

E14 The preparation of the phenethylamine starting material is given in Example Q. The aqueous mixture was extracted with ethyl acetate. The organic phase was washed with water, 2N hydrochloric acid, water and 2N aqueous sodium hydroxide solution. The extract yielded a residue which was recrystallised twice from propan-2-ol to give the desired product, the melting point of which is given in the last column of Table E.

E15 Ethyl acetate was added after the water and the desired product was obtained from the organic layer and treated with a mixture of ether and petroleum ether. The product was used without further purification.

E16 After the addition of the water, the reaction mixture was extracted with ethyl acetate and the organic phase was washed with 1N hydrocloric acid, water, then 1N aqueous sodium hydroxide solution, dried over magnesium sulphate and the solvent removed to give the desired product which was used without further purification.

E17 After the addition of water, the mixture was stirred for 30 minutes, then the organic layer separated, washed with dilute aqueous sodium hydroxide solution, dilute aqueous hydrochloric acid and then brine, dried and filtered. The filtrate yielded a gum which was purified by column chromatography, using a 1:3 mixture of ethyl acetate and petroleum ether as eluant, to yield the desired product.

E18 After the addition of water, the mixture was stirred for 1 hour, then the organic layer was separated and the aqueous layer was extracted with ether. The combined organic layers were washed with dilute hydrochloric acid, dilute sodium hydroxide, and brine, and were then dried over magnesium sulphate and filtered. The solvent was removed from the filtrate in vacuo to yield a solid which was triturated with petroleum ether (b.p. 60°–80° C.) and collected by filtration to yield the desired product.

E19 After the addition of water, the organic layer was separated and the aqueous layer was extracted with ether. The combined organic layers were washed with dilute hydrochloric acid, dilute sodium hydroxide, and brine, and were then dried over magnesium sulphate and filtered. The solvent was removed from the filtrate in vacuo to yield a gum which was used without further purification.

TABLE E

| Ex | OR$_5$ | R$_4$ | E | G | SM | a | b | c | d | e | Note | mp |
|---|---|---|---|---|---|---|---|---|---|---|---|---|
| E1 | 4-OMe | 3-F | (CH$_2$)$_3$ | 4-chlorophenyl | K | 15 | 150 | 12 | 10 | 500 | E1 | |
| E2 | 4-OMe | 3-F | (CH$_2$)$_3$ | 4-bromophenyl | CL6 | 16 | 150 | 10.3 | 10 | 500 | E2 | |
| E3 | 4-OMe | 3-OMe | (CH$_2$)$_3$ | 3-trifluoromethylphenyl | CL7 | 22.8 | 200 | 15.7 | 15.7 | 300 | E2 | |
| E4 | 4-OMe | 3-F | (CH$_2$)$_2$ | 2,4-dichlorophenyl | CL8 | 16 | 100 | 17.6 | 25 | 400 | E2 | 88–90 |
| E5 | 4-OMe | 3-F | (CH$_2$)$_3$ | 2,4-dichlorophenyl | CL9 | 13.4 | 150 | 9 | 10 | 500 | E3 | |
| E6 | 4-OMe | 3-Cl | (CH$_2$)$_3$ | phenyl | CL10 | 41.8 | 300 | 44.6 | 38 | 1000 | E4 | 72.5–73.5 |
| E7 | 4-OMe | 3-OMe | (CH$_2$)$_2$ | 4-chlorophenyl | CL12 | 25 | 50 | 20.9 | 18 | 25 | E5 | |
| E8 | 4-OMe | 3-OMe | (CH$_2$)$_4$ | 4-chlorophenyl | CL13 | 23.7 | 100 | 17.6 | 17.5 | 100 | E6 | |

TABLE E-continued

| Ex | OR₅ | R₄ | E | G | SM | a | b | c | d | e | Note | mp |
|---|---|---|---|---|---|---|---|---|---|---|---|---|
| E9 | 4-OMe | 3-OMe | (CH₂)₄ | phenyl | CL14 | 25.2 | 200 | 21.7 | 21.8 | 100 | E6 | |
| E10 | 4-OMe | 3-OMe | (CH₂)₅ | 4-chloro-phenyl | CL15 | 11 | 50 | 7.7 | 7.7 | 50 | E6 | |
| E11 | 4-OMe | 3-OMe | (CH₂)₃ | 4-bromo-phenyl | CL6 | 15 | 100 | 10 | 10 | 250 | E4 | 83–84 |
| E12 | 4-OMe | 3-OMe | (CH₂)₃ | 3,4-di-chloro-phenyl | CL16 | 30 | 200 | 20.5 | 20.6 | 100 | E6 | |
| E13 | 4-OMe | 3-OMe | (CH₂)₄ | 4-methoxy-phenyl | CL17 | 15.3 | 200 | 11.5 | 11.5 | 100 | E5 | |
| E14 | 4-OMe | 3-Br | (CH₂)₃ | phenyl | CL10 | 25.4 | 100 | 30 | 23.4 | 400 | E4 | 81–82 |
| E15 | 4-OMe | 3-OMe | W | phenyl | CL18 | 20 | 150 | 16.2 | 14.7 | 450 | E7 | 117–119 |
| E16 | 4-OMe | 3-Cl | (CH₂)₃ | 2-chloro-phenyl | CL2 | 12.4 | 100 | 10 | 9.7 | 150 | E4 | 92–93 |
| E17 | 4-OMe | 3-OMe | (CH₂)₃ | 2-tri-fluoro-methyl-phenyl | CL19 | 14 | 100 | 10 | 10 | 500 | E8 | 102–104 |
| E18 | 4-OMe | 3-F | (CH₂)₃ | 2-chloro-phenyl | CL2 | 19.2 | 150 | 14 | 11.5 | 500 | E2 | |
| E19 | 4-OMe | 3-F | (CH₂)₃ | phenyl | CL10 | 16.5 | 150 | 14 | 11.5 | 500 | E2 | |
| E20 | 2-OMe | H | (CH₂)₃ | 4-chloro-phenyl | K | 12.1 | 100 | 8 | 9.5 | 50 | E9 | 103–105 |
| E21 | 4-OMe | 3-OMe | (CH₂)₂ | phenyl | CL21 | 16 | 100 | 16 | 15.9 | 50 | E6 | |
| E22 | 4-OMe | 3-OMe | (CH₂)₅ | phenyl | CL22 | 20 | 100 | 15.7 | 18.2 | 200 | E2 | |
| E23 | 4-OMe | 3-OMe | (CH₂)₃ | 2-naphthyl | CL24 | 6 | 100 | 4 | 3.5 | 60 | E10 | 95–96 |
| E24 | 4-OMe | 3-Cl | W | phenyl | CL18 | 13 | 100 | 10.8 | 10.6 | 500 | E11 | 129–131 |
| E25 | 3-OMe | 4-Cl | (CH₂)₃ | phenyl | CL10 | 14.2 | 50 | 13.6 | 25 | 150 | E12 | |
| E26 | 4-OMe | 2-Cl 3-OMe | (CH₂)₃ | phenyl | CL10 | 7.5 | 100 | 8.3 | 7 | 100 | E2 E12 | |
| E27 | 5-OMe | 2-Cl | (CH₂)₃ | phenyl | CL10 | 14.2 | 150 | 14 | 11.5 | 500 | E1 | |
| E28 | 4-OMe | 3-OMe | (CH₂)₃ | 2,4-di-chloro-phenyl | CL9 | 9 | 75 | 7.3 | 9 | 75 | E13 | |
| E29 | 4-OMe | H | (CH₂)₃ | 2-chloro-phenyl | CL2 | 23 | 80 | 15.1 | 15 | 100 | E13 | |
| E30 | 4-OMe | 3-Ph | (CH₂)₃ | 2-chloro-phenyl | CL2 | 9.1 | 50 | 10 | 9 | 170 | E14 | 110–113 |
| E31 | 4-OMe | 3-OMe | (CH₂)₃ | 3-chloro-phenyl | CL25 | 6 | 50 | 5.7 | 6 | 50 | E13 | |
| E32 | 4-OBz | 3-OMe | (CH₂)₃ | phenyl | CL10 | 15.2 | 250 | 20 | 26 | 500 | E2 | |
| E33 | 4-OBz | 3-OMe | (CH₂)₃ | 2-methoxy-phenyl | CL26 | 11.4 | 100 | 13.2 | 9.2 | 200 | E15 | |
| E34 | 4-OBz | 3-OMe | (CH₂)₃ | 3-methoxy-phenyl | CL27 | 8.75 | 150 | 10.4 | 9 | 175 | E16 | |
| E35 | 4-OBz | 3-OMe | (CH₂)₂ | 2-chloro-phenyl | CL11 | 8.64 | 50 | 11.8 | 30 | 100 | E2 | |
| E36 | 4-OBz | 3-OMe | (CH₂)₃ | 2-chloro-phenyl | CL2 | 15 | 100 | 22 | 83 | 300 | E2 | |
| E37 | 4-OBz | 3-OMe | (CH₂)₃ | 2,4-di-chloro-phenyl | CL9 | 15 | 100 | 16.8 | 11.8 | 500 | E2 | |
| E38 | 4-OBz | 3-OMe | (CH₂)₃ | 2-methyl-thio-phenyl | CL31 | 7.2 | 20 | 7.7 | 8 | 100 | E17 | |
| E39 | 4-OMe | 3-OMe | (CH₂)₃ | 4-bi-phenylyl | CL29 | 8.9 | 100 | 9.1 | 9 | 400 | E18 | |
| E40 | 4-OBz | 3-OMe | (CH₂)₅ | phenyl | CL22 | 14.5 | 100 | 18.4 | 12.9 | 400 | E2 | |
| E41 | 4-OBz | 3-OMe | (CH₂)₄ | 2-chloro phenyl | CL23 | 6.9 | 100 | 10.8 | 13 | 400 | E19 | |
| E42 | 4-OMe | 3-F | (CH₂)₃ | 2-bromo-phenyl | CL1 | 14 | 100 | 9 | 10 | 500 | E3 | 112–114 |
| E43 | 4-OBz | 3-OMe | W | 2-chloro-phenyl | CL30 | 12.9 | 400 | 8.7 | 20 | 100 | E2 | |

EXAMPLE E44

A solution of 1-phenylcyclobutanecarbonyl chloride (129 g) in dichloromethane (500 ml) was added under nitrogen over 1.5 hours to a stirred mixture of 4-methoxyphenethylamine (99.5 g), dichloromethane (500 ml) and triethylamine (110 ml). The mixture was stirred at 20°–25° C. for one hour and allowed to stand for 16 hours. The reaction mixture was washed with 2N hydrochloric acid, water and 2N aqueous sodium hydroxide solution, dried and evaporated to give N-[2-(4-methoxyphenyl)ethy] -1-phenylcyclobutane carboxamide.

EXAMPLE E45

A solution of 1-(1-naphthyl)cyclopropane carbonyl chloride (7.1 g, prepared as described in Example CL32) in ethyl acetate (50 ml) was added to a stirred mixture of 4-benzyloxy-3-methoxyphenethylamine hydrochloride (9.29 g) in ethyl acetate (150 ml). Triethylamine (25 ml) was added and the mixture stirred for a further 64 hours. The organic layer was washed with dilute hydrochloric acid, dried over sodium sulphate and the solvent removed in vacuo to yield N-[2-(4-benzyloxy-3-methoxyphenyl)-ethyl]-1-(1-naphthyl)cyclopropane carboxamide (14.1 g).

1-arylcyclobutane carboxylic acid is a known compound or is commercially available, this is shown by a K in column SM.

In Table CL W represents —CH$_2$.CMe$_2$.CH$_2$—.

TABLE CL

| Ex | E | G | SM | a | b | c | bp |
|---|---|---|---|---|---|---|---|
| CL1 | (CH$_2$)$_3$ | 2-bromophenyl | H1 | 12 | 8.4 | 2 | 140°/3 mbar |
| CL2 | (CH$_2$)$_3$ | 2-chlorophenyl | H2 | 13 | 11 | 2.5 | 170–172°/20 mbar |
| CL3 | (CH$_2$)$_3$ | 4-fluorophenyl | H3 | 25 | 23 | 2 | 141–146°/20 mbar |
| CL4 | (CH$_2$)$_3$ | 2-methylphenyl | H4 | 15 | 14 | 2 | 180°/30 mbar |
| CL5 | (CH$_2$)$_3$ | 2-fluorophenyl | H5 | 25 | 41 | 2–3 | 115–120°/10 mbar |
| CL6 | (CH$_2$)$_3$ | 4-bromophenyl | H6 | 34 | 49 | 4 | 120–122°/3 mbar |
| CL7 | (CH$_2$)$_3$ | 3-trifluoromethyl-phenyl | H19 | 25 | 123 | 2 | 95–99°/0.6 mbar |
| CL8 | (CH$_2$)$_2$ | 2,4-dichlorophenyl | K | 20 | 30 | 2 | 128–130°/1 mbar |
| CL9 | (CH$_2$)$_3$ | 2,4-dichlorophenyl | H7 | 55 | 58 | 3 | 126–132°/1.5 mbar |
| CL10 | (CH$_2$)$_3$ | phenyl | K | 75 | 245 | 2 | 64°/0.1 mbar–80°/0.1 mbar |
| CL11 | (CH$_2$)$_2$ | 2-chlorophenyl | K | 146.5 | 177.3 | 3 | 93°/0.5 mbar |
| CL12 | (CH$_2$)$_2$ | 4-chlorophenyl | K | 50 | 66 | 1.5 | 106–108°/1 mbar |
| CL13 | (CH$_2$)$_4$ | 4-chlorophenyl | K | 25 | 30 | 1 | 122–124°/1 mbar |
| CL14 | (CH$_2$)$_4$ | phenyl | K | 25 | 34 | 2 | 180–182°/30 mbar |
| CL15 | (CH$_2$)$_5$ | 4-chlorophenyl | K | 13 | 14 | 1 | 112°/0.5 mbar |
| CL16 | (CH$_2$)$_3$ | 3,4-dichlorophenyl | K | 58 | 62 | 2 | 134°/2 mbar |
| CL17 | (CH$_2$)$_4$ | 4-methoxyphenyl | K | 25 | 30 | 2 | 204–206°/3 mbar |
| CL18 | W | phenyl | H8 | 49 | 74 | 2 | 70–74°/0.4 mbar |
| CL19 | (CH$_2$)$_3$ | 2-trifluoromethyl-phenyl | H9 | 36 | 52.5 | 1.5 | 78–82°/1 mbar |
| CL20 | (CH$_2$)$_3$ | 4-trifluoromethoxy-phenyl | H10 | 6.6 | 3.9 | 3 | 120–125°/0.26 mbar |
| CL21 | (CH$_2$)$_2$ | phenyl | K | 20 | 20 | 2 | 154–156°/30 mbar |
| CL22 | (CH$_2$)$_5$ | phenyl | K | 47 | 65.5 | 2 | 98–102°/1.5 mbar |
| CL23 | (CH$_2$)$_4$ | 2-chlorophenyl | H17 | 6.8 | 11.5 | 2 | 120–122°/2 mbar |
| CL24 | (CH$_2$)$_3$ | 2-naphthyl | H11 | 12 | 9.5 | 2.5 | 230°/30 mbar |
| CL25 | (CH$_2$)$_3$ | 3-chlorophenyl | H12 | 88 | 110 | 2.5 | 120–124°/3 mbar |
| CL26 | (CH$_2$)$_3$ | 2-methoxyphenyl | H13 | 20 | 49 | 2 | 98–102°/0.6 mbar |
| CL27 | (CH$_2$)$_3$ | 3-methoxyphenyl | H14 | 56.7 | 120 | 2 | 126–132°/2 mbar |
| CL28 | (CH$_2$)$_3$ | 4-methoxyphenyl | H18 | 21 | 164 | 2 | 130°/–1/mbar |
| CL29 | (CH$_2$)$_3$ | 4-biphenylyl | K | 17 | 49 | 4 | ND |
| CL30 | W | 2-chlorophenyl | H16 | 9.1 | 16.4 | 2 | 64–68°/0.1 mbar |

EXAMPLE E46

Cyclobutanecarbonyl chloride (19 g) was added dropwise at ambient temperature to a stirred solution of 3,4-dimethoxyphenethylamine (30.5 g) and triethylamine (23.5 ml) in tetrahydrofuran (1 l). After 1.5 hours the mixture was poured onto dilute hydrochloric acid (1 l) and the product was extracted into ethyl acetate. The extracts yielded N-[2-(3,4-dimethoxyphenyl)ethyl]cyclobutanecarboxamide (44 g) which was used without further purification.

EXAMPLES CL

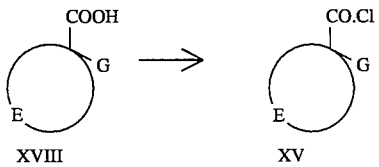

XVIII    XV

1-Arylcycloalkanecarbonyl chlorides of formula XV were prepared by heating 1-arylcycloalkane carboxylic acids of formula XVIII (a g prepared as described in the Example identified in column SM of Table CL) and thionyl chloride (b g) under reflux for c hours. The required product was obtained by distillation under reduced pressure. The boiling point is given in the last column of Table CL. Where the

EXAMPLE CL31

1-(2-Methylthiophenyl)cyclobutane carboxylic acid (12.1 g, prepared as described in Example H15) was heated under reflux for 1 hour with thionyl chloride (12 ml). Excess thionyl chloride was removed by distillation and the residue was used without further purification.

EXAMPLE CL32

1-(1-Naphthyl)cyclopropane carboxylic acid (6.7 g, prepared in a similar manner to that described in Example H20), was added to thionyl chloride (25 ml) and the mixture heated at 90°–95° C. for 1 hour. Excess thionyl chloride was removed in vacuo to yield 1-(1-naphthyl)cyclopropanecarbonyl chloride (7.1 g) which was used without further purification.

EXAMPLES H

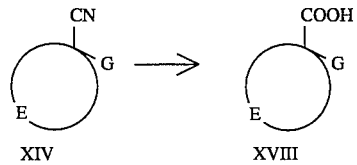

XIV    XVIII

A mixture of a 1-arylcycloalkane carbonitrile of formula XIV (a g prepared as described in the Example identified in column SM of Table H), a solution of potassium hydroxide (b g) in either water (c ml) or ethylene glycol (d ml) was heated under reflux until the reaction was complete. Acidification of the reaction mixture gave the required 1-arylcycloalkane carboxylic acid of formula XVIII, the melting point of which is given in the last column of Table H.

Notes to Table H

Where the starting carbonitrile is known, this is indicated by K in column SM.

W represents —$CH_2.CMe_2.CH_2$—

ND indicates that the melting point was not determined.

H1 The product was recrystallised from a mixture of ethyl acetate and petroleum ether (b.p. 60°–80° C.).

H2 The cooled reaction solution was washed with ethyl acetate and filtered. The filtrate was acidified and extracted with ethyl acetate. The extract yielded a solid which was recrystallised from petroleum ether (b.p. 60°–80° C.).

H3 The acidified reaction mixture was extracted with ether, the extracts washed with water and brine, then dried over magnesium sulphate and concentrated. The residue was recrystallised from petroleum ether (b.p. 60°–80° C.).

H4 The reaction mixture was poured onto water, acidified and extracted with ethyl acetate to yield the desired product.

H5 The reaction mixture was poured onto water, acidified and extracted with ethyl acetate to yield a gum which solidified on standing. This solid was dissolved in 5N aqueous sodium hydroxide solution, stirred for 30 minutes then washed with ethyl acetate. The aqueous phase was reacidified and the resulting solid collected by filtration and dried in air.

TABLE H

| Ex | E | G | SM | a | b | c | d | Note | mp |
|---|---|---|---|---|---|---|---|---|---|
| H1 | $(CH_2)_3$ | 2-bromophenyl | K | 20 | 40 | 500 | | | 122–124 |
| H2 | $(CH_2)_3$ | 2-chlorophenyl | N1 | 15 | 10.7 | | 44 | | 112–114 |
| H3 | $(CH_2)_3$ | 4-fluorophenyl | K | 40 | 32 | | 130 | H1 | 102–104 |
| H4 | $(CH_2)_3$ | 2-methylphenyl | N2 | 38 | 30 | | 125 | | 78–80 |
| H5 | $(CH_2)_3$ | 2-fluorophenyl | K | 30 | 80 | 500 | | H2 | 88–89 |
| H6 | $(CH_2)_3$ | 4-bromophenyl | K | 34 | 16 | | 150 | | 108–110 |
| H7 | $(CH_2)_3$ | 2,4-dichlorophenyl | N3 | 52 | 26 | | 200 | | 149–154 |
| H8 | W | phenyl | N8 | 53 | 33 | | 300 | | 93–95 |
| H9 | $(CH_2)_3$ | 2-trifluoromethyl-phenyl | N4 | 37 | 18 | | 150 | | 125–127 |
| H10 | $(CH_2)_3$ | 4-trifluoromethoxy-phenyl | N10 | 5 | 2.9 | | 12 | H3 | 55–58 |
| H11 | $(CH_2)_3$ | 2-naphthyl | K | 14 | 9.2 | | 37 | | 127–129 |
| H12 | $(CH_2)_3$ | 3-chlorophenyl | K | 85 | 50 | | 243 | | 100–104 |
| H13 | $(CH_2)_3$ | 2-methoxyphenyl | N5 | 25 | 15 | | 150 | | ND |
| H14 | $(CH_2)_3$ | 3-methoxyphenyl | N6 | 55 | 33 | | 250 | | ND |
| H15 | $(CH_2)_3$ | 2-methylthiophenyl | N7 | 13.6 | 9 | | 10 | H4 | ND |
| H16 | W | 2-chlorophenyl | N11 | 8.6 | 5 | | 50 | | ND |
| H17 | $(CH_2)_4$ | 2-chlorophenyl | N12 | 16.7 | 10.6 | | 50 | H5 | ND |

EXAMPLE H18

A mixture of 1-(4-methoxyphenyl)cyclobutane carbonitrile (41 g), potassium hydroxide (20 g) and diethylene glycol (160 ml) was heated under reflux for 3.5 hours. The mixture was added to water, acidified with dilute hydrochloric acid and extracted with ether. The extract yielded 1-(4-methoxyphenyl)cyclobutane carboxylic acid.

EXAMPLE H19

A solution of sodium hydroxide (2.8 g) in water (4 ml) was added to a stirred solution of 1-(3-trifluoromethylphenyl)cyclobutanecarbonitrile (50 g) in industrial methylated spirits (350 ml). To this was added hydrogen peroxide (100 vol. 105 ml) dropwise over 1 hour at a temperature of ~40° C. The mixture was then heated at 50° C. for 1 hour, allowed to cool, acidified with 5% sulphuric acid (~40 ml) and concentrated in vacuo. The residue was partitioned between water and ether. The organic extracts were washed with water, dried ($MgSO_4$), filtered and evaporated in vacuo to yield a colourless oil (63 g) which was dissolved in dioxan (350 ml). Concentrated hydrochloric acid (75 ml) was added and the solution cooled to 5° C. A solution of sodium nitrite (27 g) in water (60 ml) was added dropwise whilst maintaining the temperature at ~10° C. The mixture was then heated at 90°–95° C. overnight. The mixture was cooled and the organic layer isolated. The aqueous layer was extracted with ether and the combined organic layers dried, filtered and concentrated in vacuo to yield 1-(3-trifluoromethylphenyl)cyclobutane carboxylic acid.

EXAMPLE H20

A mixture of 1-(1-naphthyl)cyclopropanecarbonitrile (60.7 g, prepared in a similar manner to that described in Example N9) and 10% aqueous potassium hydroxide solution was stirred and heated under reflux for 16 hours. Ethylene glycol (250 ml) was added and the mixture was heated under reflux for 5 hours. Each time complete solution was achieved, further water was added to cloud point. Water (500 ml) was added and the mixture was allowed to stand for 16 hours. The resulting solid was removed by filtration. The filtrate was diluted with water (800 ml), filtered, and the filtrate acidified by addition of dilute hydrochloric acid. The resulting solid was collected by filtration, washed with water and dried in air, yielding 1-(1-naphthyl)cyclopropane carboxylic acid (25.9 g).

EXAMPLES N

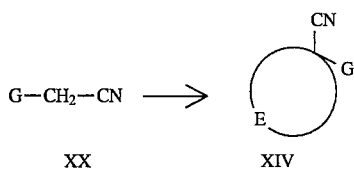

A mixture of an arylacetonitrile of formula XX (a g) and 1,3-dibromopropane (b g) and either ether (c ml) or dimethylsulphoxide (d ml) was added dropwise to a stirred suspension of powdered potassium hydroxide (e g) in dimethylsulphoxide (f ml). The reaction mixture was then treated by method A, B, C, D or E.

Method A

The mixture was heated at 30°–35° C. for 3 hours (2 hours for Example N3) and then poured into a mixture of ice/water and concentrated hydrochloric acid at below 15° C. and filtered. The filtrate was extracted with ether. The extract gave an oil which was distilled to give the desired 1-arylcyclobutanecarbonitrile of formula XIV, the boiling point of which is given in Table N.

Method B

The mixture was stirred at ambient temperature for 16 hours and poured into water. The mixture was extracted with ethyl acetate. The extract yielded an oil which was distilled to give the desired 1-arylcyclobutanecarbonitrile of formula XIV, the boiling point of which is given in Table N.

Method C

The mixture was stirred at ambient temperature for 16 hours and poured into water. The resulting precipitate was collected by filtration and dissolved in ether. The filtrate was extracted with ether. The solution and extracts were combined and yielded an oil which was distilled to give the desired 1-arylcyclobutanecarbonitrile of formula XIV, the boiling point of which is given in Table N.

Method D

The mixture was stirred at ambient temperature for 3 hours, then at 30°–35° C. for 3 hours, then poured into a mixture of ice/water and concentrated hydrochloric acid. The mixture was washed with ether and the organic extracts washed with water, dried, filtered and the solvent evaporated to give the desired 1-arylcyclobutanecarbonitrile of formula XIV, the boiling point of which is given in Table N.

Method E

The starting nitrile was prepared as described in Example R. The mixture was stirred at ambient temperature for 1 hour and poured into water. The mixture was extracted with ethyl acetate. The extract yielded an oil which was distilled. The fraction with a boiling point greater than 160° C. was purified by flash chromatography using a 1:9 mixture of petroleum ether and ethyl acetate as eluant. The solvent was evaporated to give the desired 1-arylcyclobutanecarbonitrile of formula XIV.

TABLE N

| Ex | G | a | b | c | d | e | f | Method | bp |
|---|---|---|---|---|---|---|---|---|---|
| N1 | 2-chlorophenyl | 50 | 71 | 150 | | 79 | 300 | A | 108–112°/1 mbar |
| N2 | 2-methylphenyl | 50 | 77 | | 115 | 87 | 500 | B | 165–175°/20 mbar |
| N3 | 2,4-dichlorophenyl | 100 | 120 | 250 | | 132 | 500 | A | 128–134°/0.7 mbar |
| N4 | 2-trifluoromethylphenyl | 50 | 71 | | 100 | 61 | 500 | B | 92–98°/1 mbar |
| N5 | 2-methoxyphenyl | 150 | 222 | | 200 | 269 | 1400 | C | 142–148°/1.0 mbar |
| N6 | 3-methoxyphenyl | 100 | 165 | 200 | | 181.5 | 375 | D | 114–118°/3.4 mbar |
| N7 | 2-methylthiophenyl | 26.2 | 35.7 | | 100 | 42.4 | 200 | E | ND |

EXAMPLE N8

A mixture of phenylacetonitrile (47.4 g) and 1,3-diiodo-2,2-dimethylpropane (131.2 g) was added dropwise over 2 hours at 25° C. to a stirred solution of powdered potassium hydroxide (90.7 g) in dry dimethylsulphoxide (600 ml) under a nitrogen atmosphere. The mixture was stirred overnight then poured onto water and extracted with ether (1000 ml). The extracts were decolourised with charcoal, filtered and concentrated in vacuo to yield an orange-brown oil which was distilled under vacuum to give 2,2-dimethyl-1-phenylcyclobutane carbonitrile, (b.p. 101°–106° C./0.6mbar) as a pale yellow oil.

EXAMPLE N9

A solution of 1-naphthylacetonitrile (53 g) in 1-bromo-2-chloroethane (35.2 ml) was added over 35 minutes to a vigorously stirred mixture of benzyltriethylammonium chloride (2 g) and 50% w/v aqueous sodium hydroxide solution (190 ml) at approximately 70° C. The mixture was heated at 75°–80° C. for 2 hours, then 1-bromo- 2-chloro-ethane (15 ml) and benzyltriethylammonium chloride (1 g) were added and heating continued for 4.5 hours. After standing for 16 hours, 1-bromo-2-chloroethane (10 ml), benzyltriethylammonium chloride (1 g) and solid sodium hydroxide (20 g) were added. The mixture was stirred and heated at 75°–80° C. for 6 hours. The aqueous layer was washed with ether and the combined organic layers yielded an oil which was distilled (b.p. 135° C./0.07 mbar) to give a distillate which solidified on cooling. The solid, 1-(1-naphthyl)cyclopropanecarbonitrile was used without further purification.

EXAMPLE N10

A solution of 4-trifluoromethoxyphenylacetonitrile (38.9 g) and 1,3-dibromopropane (39.1 g) in tetrahydrofuran (50 ml) was added under argon to a stirred solution of 50% sodium hydride (19.2 g) in tetrahydrofuran (200 ml) and dimethylformamide (25 ml) at 25°–30° C. over 1 hour. The mixture was stirred at 20° C. for 1.5 hours, then at 30°–40° C. for 1 hour, then cooled and water added. The mixture was filtered and washed with ether. The organic layer was washed with water, dried over magnesium sulphate and the solvent removed by evaporation. The residue was distilled (b.p. 111°– 117° C./10 mbar) to give 1-(4-trifluoromethoxyphenyl)cyclobutanecarbonitrile (30.98 g).

EXAMPLE N11

A mixture of 2-chlorophenylacetonitrile (26.5 g), 1,3-diiodo-2,2-dimethylpropane (56 g) and dimethyl sulphoxide (300 ml) was added dropwise to a stirred suspension of powdered potassium hydroxide (40 g) in dry dimethylsulphoxide (300 ml). The mixture was stirred for one hour, then poured onto ice/water and extracted with ethyl acetate. The extracts yielded an oil which was distilled under vacuum to give 2,2-dimethyl-1-(2-chlorophenyl)cyclobutane carbonitrile, (b.p. 116°– 120° C./1 mbar) which was recrystallised from petroleum ether (b.p. 60°–80° C.) m.p. 65°–69° C.

EXAMPLE N12

A mixture of 2-chlorophenylacetonitrile (20 g), 1,4-dibromobutane (28.5 g) and dimethyl sulphoxide (100 ml) was added dropwise to a stirred suspension of powdered potassium hydroxide (26 g) in dry dimethylsulphoxide (300 ml). The mixture was stirred for one hour, then poured onto ice/water and extracted with ethyl acetate. The extracts yielded an oil which was distilled under vacuum (b.p. 112°–116° C./1 mbar) to give 1-(2-chlorophenyl)cyclopentanecarbonitrile (16.7 g).

EXAMPLE P

Methyl iodide (110 g was added dropwise to a stirred solution of 4-chloro-3-methylphenol (100 g) and potassium carbonate (194 g) in acetone (500 ml). The mixture was stirred for 1.5 hours. Methyl iodide (142 g) was added and the mixture stirred for a further hour. Solvent was removed by evaporation and the residue partitioned between water and ethyl acetate. The organic layer yielded an oil which was heated under reflux for 2 hours with N-bromosuccinimide (119 g) and benzoyl peroxide (1 g) in carbon tetrachloride (250 ml). The mixture was cooled, filtered and the filtrate concentrated to give a residue which was distilled under high vacuum. The fractions collected between 88° and 94° C./0.4 mbar were recrystallised from petroleum ether (b.p. 60°–80° C.) to give 2-chloro-5-methoxy benzyl bromide, m.p. 51°–52° C.

Sodium cyanide (10.4 g) was added portionwise to a stirred solution of the above benzyl bromide (25 g) in a 2:1 mixture of ethanol and water (250 ml). The mixture was stirred for one hour at 50° C., poured into water and extracted with ether. The extract gave 2-chloro-5-methoxyphenylacetonitrile (m.p. 62°–65° C.). 10M Boranemethylsulphide complex (11.3 ml) was added dropwise under nitrogen to a refluxing solution of the above phenylacetonitrile (18.6 g) in tetrahydrofuran (150 ml). The mixture was heated under reflux for 2 hours and dilute hydrochloric acid was added dropwise and the acidified mixture heated at 95° C. for one hour. The cooled mixture was washed with ether, basified with dilute sodium hydroxide solution and extracted with ether. The extract yielded 2-chloro-5-methoxyphenethylamine as a yellow oil.

EXAMPLE Q

A mixture of tetrakis triphenylphosphine palladium (7 g), 3-bromo-4-methoxyphenethylamine hydrobromide (62.2 g) and toluene (400 ml) was stirred under nitrogen with 2M aqueous sodium carbonate solution (200 ml) and then a solution of phenyl boric acid (26.8 g) in ethanol (100 ml) was added. The mixture was heated under reflux for 48 hours then cooled and treated with 30% aqueous hydrogen peroxide solution (10 ml). The mixture was stirred at ambient temperature for 1 hour. The aqueous layer was separated and extracted with ether. The ether extracts were combined with the original organic phase. Distillation yielded 4-methoxy-3-phenylphenethylamine which was used without further purification.

EXAMPLE R

Phosphorus tribromide (75 g) in toluene (50 ml) was added to a stirred mixture of 2-methylthiobenzyl alcohol (42.5 g) in toluene (25 ml) over 10 minutes at 5° C. The mixture was then stirred at 40° C. for 1 hour, water (100 ml) was added and stirring continued at ambient temperature for 1 hour. The organic layer was separated and the aqueous layer extracted with ethyl acetate. The combined organic layers yielded an oil. The oil (58.6 g) was dissolved in a 1:2 mixture of water and ethanol and sodium cyanide (26.5 g) was added over 15 minutes. The mixture was stirred at 50° C. for 1.5 hours then poured onto water (500 ml) and extracted with ethyl acetate. The extract yielded 2-methylthiophenylacetonitrile.

EXAMPLE 94

The use of compounds of the present invention in the manufacture of pharmaceutical compositions is illustrated by the following description. In this description the term "active compound" denotes any compound of the invention but particularly any compound which is the final product of one of the preceding Examples.

a) Capsules

In the preparation of capsules, 10 parts by weight of active compound and 240 parts by weight of lactose are de-aggregated and blended. The mixture is filled into hard gelatin capsules, each capsule containing a unit dose of part of a unit dose of active compound.

b) Tablets

Tablets are prepared from the following ingredients.

|  | Parts by weight |
| --- | --- |
| Active compound | 10 |
| Lactose | 190 |
| Maize starch | 22 |
| Polyvinylpyrrolidone | 10 |
| Magnesium stearate | 3 |

The active compound, the lactose and some of the starch are de-aggregated, blended and the resulting mixture is granulated with a solution of the polyvinylpyrrolidone in ethanol. The dry granulate is blended with the magnesium stearate and the rest of the starch. The mixture is then compressed in a tabletting machine to give tablets each containing a unit dose or a part of a unit dose of active compound.

c) Enteric coated tablets

Tablets are prepared by the method described in (b) above. The tablets are enteric coated in a conventional manner using a solution of 20% cellulose acetate phthalate and 3% diethyl phthalate in ethanol:dichloromethane (1:1).

d) Suppositories

In the preparation of suppositories, 100 parts by weight of active compound is incorporated in 1300 parts by weight of triglyceride suppository base and the mixture formed into suppositories each containing a therapeutically effective amount of active ingredient.

We claim:

1. A tetrahydroisoquinoline compound of formula I

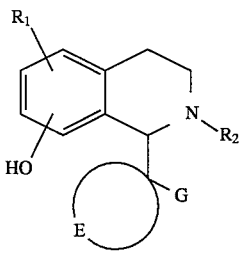

or a pharmaceutically acceptable salt thereof, in which, $R_1$ represents one or more substituents selected from H, halo, hydroxy, alkyl of 1 to 3 carbon atoms (optionally substituted by hydroxy), alkoxy of 1 to 3 carbon atoms, alkylthio of 1 to 3 carbon atoms, alkylsulphinyl of 1 to 3 carbon atoms, alkylsulphonyl of 1 to 3 carbon atoms, nitro, cyano, polyhaloalkyl of 1 to 3 carbon atoms, polyhaloalkoxy of 1 to 3 carbon atoms, phenyl (optionally substituted by one or more substituents selected from halo, alkyl of 1 to 3 carbon atoms or alkoxy of 1 to 3 carbon atoms), or $R_1$ is carbamoyl optionally alkylated by one or two alkyl groups each independently of 1 to 3 carbon atoms;

$R_2$ represents an aliphatic group containing 1 to 3 carbon atoms optionally substituted by hydroxy or alkoxy containing 1 to 3 carbon atoms;

E represents an alkylene chain containing 2 to 5 carbon atoms optionally substituted by one or more alkyl groups containing 1 to 3 carbon atoms, and G represents phenyl or phenyl substituted by one or more substituents which may be the same or different, and which are independently alkyl of 1 to 3 carbon polyhaloalkyl of 1 to 3 carbon atoms, halo, hydroxy, polyhaloalkyl of 1 to 3 carbon atoms, polyhaloalkoxy of atoms, alkylsulphinyl of 1 to 3 carbon atoms, alkylsulphonyl of 1 to 3 carbon atoms, phenyl (optionally substituted by one or more substituents selected from halo, alkyl of 1 to 3 carbon atoms or alkoxy of 1 to 3 carbon atoms), carbamoyl optionally alkylated by one or two alkyl groups each independently of 1 to 3 carbon atoms, or G represents a phenyl ring having fused thereto a heterocyclic or aromatic carbocyctic ring;

and compounds of formula I which are O-acylated in the 5, 6, 7, or 8-position in the tetrahydroisoquinoline ring.

2. A tetrahydroisoquinoline compound of formula I as claimed in claim 1 wherein $R_1$ represents H, halo, hydroxy, alkyl of 1 to 3 carbon atoms, alkoxy of 1 to 3 carbon atoms, alkylthio of 1 to 3 carbon atoms, nitro, polyfluoroalkyl of 1 to 3 carbon atoms, polyfluoroalkoxy of 1 to 3 carbon atoms or phenyl optionally substituted by fluoro, chloro, bromo, methyl or methoxy.

3. A tetrahydroisoquinoline compound of formula I as claimed in claim 1 or a pharmaceutically acceptable salt thereof, wherein $R_1$ represents H, fluoro, chloro, bromo, hydroxy, methyl, methoxy, phenyl or nitro.

4. A tetrahydroisoquinoline compound of formula I as claimed in claim 1 or a pharmaceutically acceptable salt thereof, wherein $R_2$ represents an alkyl group containing 1 to 3 carbon atoms optionally substituted by hydroxy or by methoxy or $R_2$ represents an alkenyl group of 2 or 3 carbon atoms.

5. A tetrahydroisoquinoline compound of formula I as claimed in claim 4 or a pharmaceutically acceptable salt thereof, wherein $R_2$ represents methyl, ethyl, 2-hydroxyethyl or 2-methoxyethyl or $R_2$ represents allyl.

6. A tetrahydroisoquinoline compound of formula I as claimed in claim 1 or a pharmaceutically acceptable salt thereof, wherein the group E represents —$(CH_2)_2$—, —$(CH_2)_3$—, —$(CH_2)_4$—, —$(CH_2)_5$— or —$CH_2CMe_2CH_2$—.

7. A tetrahydroisoquinoline compound of formula I as claimed in claim 1 pharmaceutically acceptable salt thereof, wherein G represents phenyl or phenyl substituted by one or more substituents which are independently alkyl of 1 to 3 carbon atoms, alkoxy of 1 to 3 carbon atoms, halo, hydroxy, polyfluoroalkyl of 1 to 3 carbon atoms, polyfluoroalkoxy of 1 to 3 carbon atoms or phenyl optionally substituted by fluoro, chloro, bromo, methyl or methoxy or G represents naphthyl or dihydrobenzofuran-7-yl.

8. A tetrahydroisoquinoline compound of formula I as claimed in claim 1 or a pharmaceutically acceptable salt thereof, wherein G represents phenyl or phenyl substituted by methyl, hydroxy, methoxy, methylthio, fluoro, chloro, bromo, trifluoromethyl, cyano or trifluoromethoxy or G represents a naphthyl or dihydrobenzo[b]furan-7-yl group.

9. A tetrahydroisoquinoline compound of formula I as claimed in claim 1 or a pharmaceutically acceptable salt thereof, wherein G represents phenyl, 2-chlorophenyl, 4-chlorophenyl, 2,4-dichlorophenyl, 3,4-dichlorophenyl, 4-fluorophenyl, 2-bromophenyl, 2-methylphenyl, 2-methylthiophenyl, 2-methoxyphenyl, 3-methoxyphenyl, 4-methoxyphenyl, 4-hydroxyphenyl, 3-trifluoromethyl-phenyl, 4-trifluoromethoxyphenyl, 2-cyanophenyl, 2-bromo-4,5-dimethoxyphenyl, 1-naphthyl, 2-naphthyl or 2,3-dihydrobenzo[b]furan-7-yl.

10. A tetrahydroisoquinoline compound of formula II

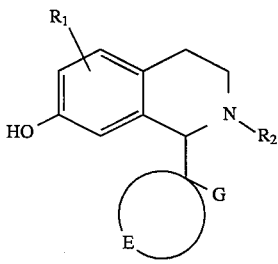

or a pharmaceutically acceptable salt thereof, wherein $R_1$, $R_2$, E and G are as defined in any preceding claim and compounds of formula II which are O-acylated in the 7 position in the tetrahydroisoquinoline ring.

11. A tetrahydroisoquinoline compound of formula I represented by compounds of formula III

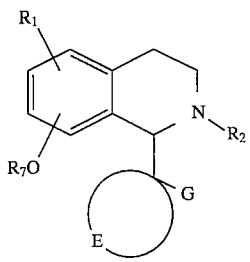

or a pharmaceutically acceptable salt thereof, in which $R_1$, $R_2$, E and G are as defined in claim 1 and $R_7$ represents an acyl group derived from a carboxylic acid having 6 to 20 carbon atoms.

12. A tetrahydroisoquinoline compound of formula III as claimed in claim 11 or a pharmaceutically acceptable salt thereof, wherein $R_7$ represents heptanoyl, decanoyl, dodecanoyl, hexadecanoyl or octadecanoyl.

13. A tetrahydroisoquinoline compound of formula III as claimed in claim 11 or a pharmaceutically acceptable salt thereof, wherein the group $OR_7$ is in the 7-position.

14. A tetrahydroisoquinoline compound of formula I as claimed in claim 1 selected from the group consisting of:

1-[1-(2-chlorophenyl)cyclopropyl]-7-hydroxy-6-methoxy-2-methyl-1,2,3,4-tetrahydroisoquinoline 1-[1-(2-chlorophenyl)cyclopropyl]-7-hydroxy-6-fluoro-2-methyl-1,2,3,4-tetrahydroisoquinoline 1-[1-(2-chlorophenyl)cyclopropyl]-7-hydroxy-2,6-dimethyl-1,2,3,4-tetrahydroisoquinoline 1-[1-(2-chlorophenyl)cyclopropyl]-8-decanoyloxy-6-methoxy-2-methyl-1,2,3,4-tetrahydroisoquinoline 1-[1-(2-chlorophenyl)cyclopropyl]-7-dodecanoyloxy-6-methoxy-2-methyl-1,2,3,4-tetrahydroisoquinoline 1-[1-(2-chlorophenyl)cyclopropyl]-7-hexadecanoyloxy-6-methoxy-2-methyl-1,2,3,4-tetrahydroisoquinoline 1-[1-(2-chlorophenyl)cyclopropyl]-7-octadecanoyloxy-6-methoxy-2-methyl-1,2,3,4-tetrahydroisoquinoline 1-[1-(2-chlorophenyl)cyclopropyl]-7-decanoyloxy-6-fluoro-2-methyl-1,2,3,4-tetrahydroisoquinoline 1-[1-(2-chlorophenyl)cyclobutyl]-7-decanoyloxy-6-fluoro-2-methyl-1,2,3,4-tetrahydroisoquinoline or a pharmaceutically acceptable salt thereof in the form of individual enantiomers, racemates or other mixtures of enantiomers.

15. A pharmaceutical composition comprising a therapeutically effective amount of a compound of formula I, together with a pharmaceutically acceptable diluent or carrier.

16. A method of providing analgesia or of treating psychoses, Parkinson's disease, Lesch-Nyan syndrome, attention deficit disorder or cognitive impairment or in the relief of drug dependence or tardive dyskinesia which comprises the administration of a therapeutically effective amount of a compound of formula I as claimed in claim 1 to a patient in need thereof.

17. A method as claimed in claim 16 for treating schizophrenia.

18. The method of claim 16 for treating psychoses.

* * * * *

UNITED STATES PATENT AND TRADEMARK OFFICE
CERTIFICATE OF CORRECTION

PATENT NO. : 5,519,034
DATED : April 3, 1997
INVENTOR(S) : KOZLIK et al.

Page 1 of 2

It is certified that error appears in the above-indentified patent and that said Letters Patent is hereby corrected as shown below:

On the title page:

Item [57] Please delete "ester" insert therefor --esters--.

Item [57] Please delete "Parinson's" insert therefor --Parkinson's--.

Column 51, line 12 please delete "CA281)" insert therefor --CA28)--.

Column 85, line 46 after "1 to 3 carbon" insert therefor --atoms--.

Line 47 please delete "polyhaloalkyl" insert therefor --alkoxy--.

Line 49 please delete "of atoms" insert therefor --of 1 to 3 carbon atoms, cyano, alkylthio of 1 to 3 carbon atoms--. Line 56 please delete " carbocyctic" insert therefor --carbocyclic--.

Column 86, line 22 after "claim 1" and before "pharmaceutically" insert therefor --or a--.

UNITED STATES PATENT AND TRADEMARK OFFICE
CERTIFICATE OF CORRECTION

PATENT NO. : 5,519,034
DATED : April 3, 1997
INVENTOR(S) : KOZLIK et al.

It is certified that error appears in the above-indentified patent and that said Letters Patent is hereby corrected as shown below:

Column 87, after line 34 a compound has been ommited. Please insert -- 1-[1-(2-chlorophenyl)cyclopropyl]-7-heptanoyloxy-6-methoxy-2-methyl-1,2,3,4-tetrahydroisoquinoline--.

Column 88, line 1 please delete "8-decanoyloxy" insert therefor --7-decanoyloxy--.

Signed and Sealed this

Fifteenth Day of July, 1997

Attest:

BRUCE LEHMAN

Attesting Officer

Commissioner of Patents and Trademarks